United States Patent
Germeroth et al.

(10) Patent No.: US 11,274,278 B2
(45) Date of Patent: Mar. 15, 2022

(54) METHODS, KITS AND APPARATUS FOR EXPANDING A POPULATION OF CELLS

(71) Applicant: Juno Therapeutics GmbH, Munich (DE)

(72) Inventors: Lothar Germeroth, Munich (DE); Christian Stemberger, Holzkirchen (DE)

(73) Assignee: Juno Therapeutics GmbH, Munich (DE)

( * ) Notice: Subject to any disclaimer, the term of this patent is extended or adjusted under 35 U.S.C. 154(b) by 12 days.

(21) Appl. No.: 15/304,045

(22) PCT Filed: Apr. 16, 2015

(86) PCT No.: PCT/EP2015/058339
§ 371 (c)(1),
(2) Date: Oct. 14, 2016

(87) PCT Pub. No.: WO2015/158868
PCT Pub. Date: Oct. 22, 2015

(65) Prior Publication Data
US 2017/0037368 A1 Feb. 9, 2017

Related U.S. Application Data

(60) Provisional application No. 61/980,506, filed on Apr. 16, 2014.

(51) Int. Cl.
*C07K 14/36* (2006.01)
*C07K 14/195* (2006.01)
*C12N 5/0783* (2010.01)
*C12M 1/00* (2006.01)

(52) U.S. Cl.
CPC .......... *C12N 5/0636* (2013.01); *C12M 47/02* (2013.01); *C12M 47/12* (2013.01)

(58) Field of Classification Search
None
See application file for complete search history.

(56) References Cited

U.S. PATENT DOCUMENTS

| | | | |
|---|---|---|---|
| 4,361,549 A | 11/1982 | Kung et al. | |
| 4,851,341 A | 7/1989 | Hopp et al. | |
| 5,506,121 A | 4/1996 | Skerra et al. | |
| 5,985,658 A | 11/1999 | Colinas et al. | |
| 6,022,951 A | 2/2000 | Sano et al. | |
| 6,103,493 A | 8/2000 | Skerra et al. | |
| 6,352,694 B1 | 3/2002 | June et al. | |
| 7,482,000 B2 | 1/2009 | Devaux et al. | |
| 7,572,631 B2 | 8/2009 | Berenson et al. | |
| 7,704,708 B2 * | 4/2010 | Wu .................... | C07K 14/36 435/69.1 |
| 7,776,562 B2 | 8/2010 | Busch et al. | |
| 7,981,632 B2 | 7/2011 | Schmidt | |
| 8,298,782 B2 | 10/2012 | Busch et al. | |
| 8,735,330 B2 | 5/2014 | Geir | |
| 9,023,604 B2 | 5/2015 | Schmidt et al. | |
| 10,228,312 B2 | 3/2019 | Stadler | |
| 2003/0175850 A1 | 9/2003 | Ross et al. | |
| 2004/0082012 A1 | 4/2004 | Busch et al. | |
| 2006/0019319 A1 | 1/2006 | Billadeau et al. | |
| 2006/0106199 A1 | 5/2006 | Erdmann et al. | |
| 2007/0241061 A1 | 10/2007 | Engstrom et al. | |
| 2008/0085532 A1 | 4/2008 | Gorlach et al. | |
| 2008/0131415 A1 | 6/2008 | Riddell et al. | |
| 2008/0255004 A1 | 10/2008 | Neurauter et al. | |
| 2010/0068738 A1 | 3/2010 | Kawamura et al. | |
| 2010/0267057 A1* | 10/2010 | Rakestraw ......... | C12N 15/1037 435/7.21 |
| 2011/0070581 A1 | 3/2011 | Gupta et al. | |
| 2012/0214187 A1* | 8/2012 | Lees .................... | G01N 33/548 435/7.95 |
| 2014/0295458 A1 | 10/2014 | Schmidt et al. | |
| 2014/0314795 A1 | 10/2014 | Riddell et al. | |
| 2015/0024411 A1 | 1/2015 | Stadler | |
| 2015/0283178 A1 | 10/2015 | June et al. | |
| 2015/0306141 A1 | 10/2015 | Jensen | |
| 2016/0164580 A1 | 6/2016 | El-Najjar et al. | |

(Continued)

FOREIGN PATENT DOCUMENTS

| | | |
|---|---|---|
| CN | 101 226 118 A | 7/2008 |
| CN | 101 446 576 | 6/2009 |

(Continued)

OTHER PUBLICATIONS

Ameres et al., "Presentation of an immunodominant immediate-early CD8+ T cell epitope resists human cytomegalovirus immunoevasion," PLoS Pathog. (2013);9(5):e1003383.

Amstutz et al., "In vitro display technologies: novel developments and applications," Curr Opin Biotechnol. Aug. 2001;12(4):400-5.

Arakawa et al., "Cloning and sequencing of the VH and V kappa genes of an anti-CD3 monoclonal antibody, and construction of a mouse/human chimeric antibody," J Biochem. Sep. 1996;120(3):657-62.

Argarana et al., "Molecular cloning and nucleotide sequence of the streptavidin gene," Nucleic Acids Res. Feb. 25, 1986;14(4):1871-82.

Barrett et al., "Chimeric antigen receptor therapy for cancer," Annu Rev Med. (2014) 65:333-47.

(Continued)

*Primary Examiner* — Michail A Belyavskyi
(74) *Attorney, Agent, or Firm* — Morrison & Foerster LLP

(57) ABSTRACT

The present invention relates to in vitro-methods of expanding a population of cells such as lymphocytes, comprising contacting a sample comprising a population of cells with a multimerization reagent. The multimerization reagent has reversibly immobilized thereon (bound thereto) a first agent that provides a primary activation signal to the cells and optionally, a second agent that provides a co-stimulatory signal. The invention also provides multimerization reagents, kits, arrangements and an apparatus for expanding cells.

38 Claims, 39 Drawing Sheets

Specification includes a Sequence Listing.

(56) References Cited

U.S. PATENT DOCUMENTS

| | | | |
|---|---|---|---|
| 2016/0362472 | A1 | 12/2016 | Bitter et al. |
| 2017/0037370 | A1 | 2/2017 | Kaiser et al. |
| 2017/0051252 | A1 | 2/2017 | Morgan et al. |
| 2017/0052176 | A1* | 2/2017 | Carl ..................... G01N 33/566 |
| 2019/0112576 | A1 | 4/2019 | Germeroth et al. |
| 2019/0136186 | A1 | 5/2019 | Germeroth et al. |
| 2019/0226951 | A1 | 7/2019 | Stadler |
| 2019/0234844 | A1 | 8/2019 | Stadler |
| 2020/0017880 | A1 | 1/2020 | Bashour et al. |
| 2021/0032297 | A1 | 2/2021 | Schmidt et al. |

FOREIGN PATENT DOCUMENTS

| | | |
|---|---|---|
| CN | 101622340 | 1/2010 |
| CN | 103 305 464 | 9/2013 |
| CN | 103 502 438 | 1/2014 |
| DE | 19641876 | 4/1998 |
| EP | 0700430 | 3/1996 |
| JP | 2006-516197 | 6/2006 |
| JP | 2006-525013 | 11/2006 |
| JP | 2009-531062 | 9/2009 |
| JP | 2010-075191 | 4/2010 |
| RU | 2249039 | 3/2005 |
| RU | 2469044 | 12/2012 |
| WO | WO-86/02077 | 4/1986 |
| WO | WO-96/23879 | 8/1996 |
| WO | WO-96/24606 | 8/1996 |
| WO | WO-98/40396 | 9/1998 |
| WO | WO 2000/043551 | 7/2000 |
| WO | WO-01/04144 | 1/2001 |
| WO | WO-02/054065 | 7/2002 |
| WO | WO-02/077018 | 10/2002 |
| WO | WO-03/029462 | 4/2003 |
| WO | WO-2003/090781 | 11/2003 |
| WO | WO-2004/029221 | 4/2004 |
| WO | WO-2004/096975 | 11/2004 |
| WO | WO-2004/104185 | 12/2004 |
| WO | WO-2005/050209 | 6/2005 |
| WO | WO-2006/044650 | 4/2006 |
| WO | WO 2006058226 | * 6/2006 |
| WO | WO-2007/112012 | 10/2007 |
| WO | WO-2007/117602 | 10/2007 |
| WO | WO-2008/011486 | 1/2008 |
| WO | WO-2008/140573 | 11/2008 |
| WO | WO-2009/003493 | 1/2009 |
| WO | WO-2009/072003 | 6/2009 |
| WO | WO-2009/097119 | 6/2009 |
| WO | WO-2009/092068 | 7/2009 |
| WO | WO-2010/080032 | 7/2010 |
| WO | WO-2011/107489 | 9/2011 |
| WO | WO-2012/017081 | 2/2012 |
| WO | WO-2012/058627 | 5/2012 |
| WO | WO-2012/129514 | 9/2012 |
| WO | WO-2013/011011 | 1/2013 |
| WO | WO 2013/038272 | 3/2013 |
| WO | WO-2013/124474 | 8/2013 |
| WO | WO-2014/011996 | 1/2014 |
| WO | WO2014011489 | * 1/2014 |
| WO | WO-2014/031687 | 2/2014 |
| WO | WO-2014/076277 | 5/2014 |
| WO | WO-2015/095895 | 7/2015 |
| WO | WO-2015/158868 | 10/2015 |
| WO | WO 2015/158868 | 10/2015 |
| WO | WO-2015/162211 | 10/2015 |
| WO | WO-2015/164675 | 10/2015 |
| WO | WO 2016/166568 | 10/2016 |
| WO | WO-2017/068419 | 4/2017 |
| WO | WO-2017/068421 | 4/2017 |
| WO | WO-2017/068425 | 4/2017 |
| WO | WO-2017/096329 | 6/2017 |
| WO | WO 2018/197949 | 11/2018 |
| WO | WO-2020/033927 | 2/2020 |
| WO | WO-2020/089343 | 5/2020 |

OTHER PUBLICATIONS

Battaglia et al., "Interleukin-21 (IL-21) synergizes with IL-2 to enhance T-cell receptor-induced human T-cell proliferation and counteracts IL-2/transforming growth factor-β-induced regulatory T-cell development," Immunology. May 2013;139(1):109-20.

Bazdar et al., "Interleukin-7 enhances proliferation responses to T-cell receptor stimulation in naïve CD4+ T cells from human immunodeficiency virus-infected persons," J Virol. Nov. 2007;81(22):12670-4.

Beste et al., "Small antibody-like proteins with prescribed ligand specificities derived from the lipocalin fold," Proc Natl Acad Sci U S A. Mar. 2, 1999;96(5):1898-903.

Butler et al., "Ex Vivo Expansion of Human CD8+ T Cells Using Autologous CD4+ T Cell Help," PLoS ONE (2012) 7(1): e30229.

Carpenter et al., "Activation of human B cells by the agonist CD40 antibody CP-870,893 and augmentation with simultaneous toll-like receptor 9 stimulation," J Transl Med. Nov. 11, 2009;7:93.

Cheadle et al., "Chimeric antigen receptors for T-cell based therapy," Methods Mol Biol. (2012) 907:645-66.

Cornish et al., "Differential regulation of T-cell growth by IL-2 and IL-15," Blood. Jul. 15, 2006;108(2):600-8.

Dienz et al., "The induction of antibody production by IL-6 is indirectly mediated by IL-21 produced by CD4+ T cells," J Exp Med. Jan. 16, 2009;206(1):69-78.

Gill et al., "Biopharmaceutical drug discovery using novel protein scaffolds," Curr Opin Biotechnol. Dec. 2006;17(6):653-8.

Holliger et al., ""Diabodies": small bivalent and bispecific antibody fragments," Proc Natl Acad Sci U S A. Jul. 15, 1993;90(14):6444-8.

Holt et al., "Domain antibodies: proteins for therapy," Trends Biotechnol. Nov. 2003;21(11):484-90.

Hoshino et al., "Activation via the CD3 and CD16 pathway mediates interleukin-2-dependent autocrine proliferation of granular lymphocytes in patients with granular lymphocyte proliferative disorders," Blood. Dec. 15, 1991;78(12):3232-40.

Hudecek et al., "Direct tumour recognition and helper function of CD4+ T cells modified to express a CD19-specific CAR in vitro and in a preclinical lymphoma model," Abstract for Presentation, 39th Annual Meeting of the European Group for Blood and Marrow Transplantation, London, UK (Apr. 10, 2013), 1 page.

Hudecek et al., "Receptor affinity and extracellular domain modifications affect tumor recognition by ROR1-specific chimeric antigen receptor T cells," Clin Cancer Res. Jun. 15, 2013;19(12):3153-64.

Iliades et al., "Triabodies: single chain Fv fragments without a linker form trivalent trimers," FEBS Lett. Jun. 16, 1997;409(3):437-41.

Ill et al., "Design and construction of a hybrid immunoglobulin domain with properties of both heavy and light chain variable regions," Protein Eng. Aug. 1997;10(8):949-57.

Juntilla et al., "Single-step Strep-tag purification for the isolation and identification of protein complexes from mammalian cells," Proteomics. Apr. 2005;5(5):1199-203.

Knabel et al., "Reversible MHC multimer staining for functional isolation of T-cell populations and effective adoptive transfer," Nat Med. Jun. 2002;8(6):631-7.

Kwon et al., "Quantitative evaluation of the relative cell permeability of peptoids and peptides," J Am Chem Soc. Feb. 14, 2007;129(6):1508-9.

Li et al., "Comparison of anti-CD3 and anti-CD28-coated beads with soluble anti-CD3 for expanding human T cells: Differing impact on CD8 T cell phenotype and responsiveness to restimulation," J Transl Med. 2010; 8: 104.

Lowman, "Bacteriophage display and discovery of peptide leads for drug development," Annu Rev Biophys Biomol Struct. (1997);26:401-24.

Martin et al., "The affinity-selection of a minibody polypeptide inhibitor of human interleukin-6," EMBO J. Nov. 15, 1994;13(22):5303-9.

Mosavi et al., "The ankyrin repeat as molecular architecture for protein recognition," Protein Sci. Jun. 2004;13(6):1435-48.

(56) References Cited

OTHER PUBLICATIONS

Noguchi et al., "Preparation and properties of the immunoconjugate composed of anti-human colon cancer monoclonal antibody and mitomycin C-dextran conjugate," Bioconjug Chem. Mar.-Apr. 1992;3(2):132-7.
Riddell et al., "Adoptive Therapy with Chimeric Antigen Receptor Modified T; Cells of Defined Subset Composition," cancer J. (2014) 20(2): 141-44.
Rodi et al., "Phage-display technology—finding a needle in a vast molecular haystack," Curr Opin Biotechnol. Feb. 1999;10(1):87-93.
Schmitt et al., "Adoptive transfer and selective reconstitution of streptamer-selected cytomegalovirus-specific CD8+ T cells leads to virus clearance in patients after allogeneic peripheral blood stem cell transplantation," Transfusion. Mar. 2011;51(3):591-9.
Silverman et al., "Multivalent avimer proteins evolved by exon shuffling of a family of human receptor domains," Nat Biotechnol. Dec. 2005;23(12):1556-61.
Skerra, "A general vector, pASK84, for cloning, bacterial production, and single-step purification of antibody Fab fragments," Gene. Apr. 8, 1994;141(1):79-84.
Skerra, "Bacterial expression of immunoglobulin fragments," Curr Opin Immunol. Apr. 1993;5(2):256-62.
Skerra, "Engineered protein scaffolds for molecular recognition," J Mol Recognit. Jul.-Aug. 2000;13(4):167-87.
Smith et al., "Ex vivo expansion of human T cells for adoptive immunotherapy using the novel Xeno-free CTS Immune Cell Serum Replacement," Clinical & Translational Immunology (2015) 4:e31.
Stemberger et al., "Novel serial positive enrichment technology enables clinical multiparameter cell sorting," PLoS One. (2012);7(4):e35798.
Stone et al., "The assembly of single domain antibodies into bispecific decavalent molecules," J Immunol Methods. Jan. 10, 2007;318(1-2):88-94.
Traunecker et al., "Bispecific single chain molecules (Janusins) target cytotoxic lymphocytes on HIV infected cells," EMBO J. Dec. 1991;10(12):3655-9.
Traunecker et al., "Janusin: new molecular design for bispecific reagents," Int J Cancer Suppl. (1992);7:51-2.
Vanhove et al., "Selective blockade of CD28 and not CTLA-4 with a single-chain Fv-alpha1-antitrypsin fusion antibody," Blood. Jul. 15, 2003;102(2):564-70.
Vitale et al., "NK-active cytokines IL-2, IL-12, and IL-15 selectively modulate specific protein kinase C (PKC) isoforms in primary human NK cells," Anat Rec. Feb. 1, 2002;266(2):87-92.
Wang et al., "Phenotypic and functional attributes of lentivirus-modified CD19-specific human CD8+ central memory T cells manufactured at clinical scale," J Immunother. (2012) 35(9):689-701.
Wilson et al., "The use of mRNA display to select high-affinity protein-binding peptides," Proc Natl Acad Sci U S A. Mar. 27, 2001;98(7):3750-5.
Zhang et al., "CD137 promotes proliferation and survival of human B cells," J Immunol. Jan. 15, 2010;184(2):787-95.
"Germeroth ""IBA T-catch cell isolation in pipette tips"" Apr. 23, 2014 Retrieved from the internet: URL:http://x.ymcdn.com/sites/www.celltherapysociety.org/resource/resmgr/2014_AnnualMtgPresentations/T2_L.Germeroth.pdf [Retrieved on Jan. 23, 2017]".
Anonymous, "Cross-linking reagents introduction to cross-linking single-step vs. multi-step reactions," Published on Jan. 1, 2005. Retrieved from http://www.korambiotech.com/upload/bbs/2/Cross-LinkingTechHB.pdf. Retrieved on Nov. 30, 2018.
Anonymous, "SMCC and Sulfo-SMCC," Published Jan. 1, 2018. Retrieved on https://assets.thermofisher.com/TFS-Assets/LSG/manuals/MAN0011295_SMCC_SulfoSMCC_UG.pdf. Retrieved on Dec. 3, 2018.
Anonymous, "Traut's reagent," Published on Jan. 1, 2012. Retrieved from https://assets.thermofisher.com/TFS-Assets/LSG/manuals/MAN0011238_Trauts_Reag_UG.pdf. Retrieved on Dec. 3, 2018.
Dubel et al., "Bifunctional and multimeric complexes of streptavidin fused to single chain antibodies (scFv)," J Immunol Methods (1995) 178(2):201-209.
Skerra et al., "Applications of a peptide ligand for streptavidin: the Strep-tag," Biomolecular Engineer (1999) 16(1-4):79-86.
U.S. Appl. No. 16/231,188, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 16/231,193, filed Dec. 21, 2018, by Stadler et al. (Copy not provided). (Copy not submitted herewith pursuant to the waiver of 37 C.F. R. § 1.98(a)(2)(iii) issued by the Office on Sep. 21, 2004).
U.S. Appl. No. 15/770,177, filed Oct. 20, 2016, by Bashour et al. (Copy not provided). (Copy not submitted herewith pursuant to the waiver of 37 C.F. R. § 1.98(a)(2)(iii) issued by the Office on Sep. 21, 2004).
U.S. Appl. No. 15/770,179, filed Oct. 20, 2016, by Germeroth et al. (Copy not provided). (Copy not submitted herewith pursuant to the waiver of 37 C.F. R. § 1.98(a)(2)(iii) issued by the Office on Sep. 21, 2004).
Barrett et al., "The length and mode of termination of individual muscle fibers in the human Sartorius and posterior femoral muscles," Cell Tissues Organs (1962) 48(3):242-257.
Bashour et al., "Functional Characterization of a T Cell Stimulation Reagent for the Production of Therapeutic Chimeric Antigen Receptor T Cells," Presentation of Poster, presented at American Society of Hematology Annual Meeting, Orlando, FL (Dec. 5, 2015).
Casalegno-Garduño et al., Multimer technologies for detection and adoptive transfer of antigen-specific T cells. Cancer Immunol Immunother. Feb. 2010;59(2):195-202.
Casati et al., "Enrichment, stimulation, and viral transduction of naive and central memory CD8+ T cells under GMP conditions for translational research towards the development of adoptive cell therapy of cancer patients," MACS&more (2013) 15:20-24.
Church et al., "Tumor-specific CD4+ T cells maintain effector and memory tumor-specific CD8+ T cells," Eur J Immunol (2013) 44(1):69-79.
Dainiak et al., Methods in Cell Separations. Adv Biochem Eng Biotechnol. 2007;106:1-18.
Hudson et al., "Engineered Antibodies," Nature Medicine (2003) 9(1):129-133.
Hunziker et al., "Exhaustion of cytotoxic T cells during adoptive immunotherapy of virus carrier mice can be prevented by B cells or CD4+ T cells," Eur J Immunol (2002) 32(2):374-382.
International Search Report and Written Opinion for PCT/EP2013/053650, dated Oct. 11, 2013.
Kumar et al., "Cell separation using cryogel-based affinity chromatography",Nature Protocols, Nature Publishing Group, GB, vol. 5, No. 11, Nov. 1, 2010, pp. 1737-1747.
Kumar et al., Affinity binding of cells to cryogel adsorbents with immobilized specific ligands: effect of ligand coupling and matrix architecture. J Mol Recognit. Jan.-Feb. 2005;18(1):84-93.
Larvor et al., Measurement of the dissociation rate constant of antigen/antibody complexes in solution by enzyme-linked immunosorbent assay. J Immunol Methods. Apr. 15, 1994;170(2):167-175.
Levin et al., "Optimizing the affinity and specificity of proteins with molecular display," Mol BioSyst (2006) 2:49-57.
Li et al., "Comparison of inlet geometry in microfluidic cell affinity chromatography," Analytical chemistry (2011) 83(3):774-781.
Li et al., "Negative enrichment of target cells by microfluidic affinity chromatography," Analytical Chemistry (2011) 83(20):7863-7869.
Li et al., "Multiparameter cell affinity chromatography: Separation and analysis in a single microfluidic channel," Anal Chem (2012) 84(19):8140-8148.
Liu et al., "Characterization of TectoRNA Assembly with Cationic Conjugated Polymers," J Am Chem Soc (2004) 126(13):4076-4077.
Miltenyi et al., High Gradient Magnetic Cell Separation With MACS. Cytometry. 1990;11(2):231-238.

(56) References Cited

OTHER PUBLICATIONS

Morizono et al., "A versatile targeting system with lentiviral vectors bearing the biotin-adaptor peptide," J Gene Med. Aug. 2009;11(8):655-63.
Padmanabhan et al., Purification of Transiently Transfected Cells by Magnetic Affinity Cell Sorting. J Immunogenet. Apr. 1989;16(2):91-102.
Plieva et al., "Characterization of supermacroporous monolithic polyacrylamide based matrices designed for chromatography of bioparticles," Journal of Chromatography (2004) 807(1):129-137.
Pullagurla et al., "Parallel affinity-based isolation of leukocyte subsets using microfluidics: application for stroke diagnosis," Analytical chemistry (2014) 86(8):4058-4065.
Qiagen: "Strep-tagged Protein Purification Handbook for expressing, purifying, and detecting proteins carrying a Strep-tag II or a 6xHis tag and a Strep-tag II Two-step protein purification system His.Strep pQE-TriSystem Vector Set pQE-TriSystem Strep Vector Strep-Tactin Superflow and Superflow Cartridge", Apr. 1, 2007 (Apr. 1, 2007).
Sabatino et al., "Generation of clinical-grade CD19-specific CAR-modified CD8+ memory stem cells for the treatment of human B-cell malignancies," Blood. Jul. 28, 2016;128(4):519-28.
Schmidt and Skerra, The Strep-tag system for one-step purification and high-affinity detection or capturing of proteins. Nat Protoc. 2007;2(6):1528-1535.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37.
ThermoFisher Scientific, Avidin-Biotein Interaction, retrieved from https://www.thermofisher.com/us/en/home/life-science/protein-biology/protein-biology-learning-center/protein-biology-resource-library/pierce-protein-methods/avidin-biotin-interaction.html on Apr. 9, 2019, pp. 1-7.
Tumaini et al., "Simplified process for the production of anti-CD19-CAR-engineered T cells," Cytotherapy. Nov. 2013;15(11):1406-15.
Turtle, C.J. et al, "CD19 CAR-T cells of defined CD4+:CD8+ composition in adult B cell ALL patients," The Journal of Clinical Investigation, vol. 126, No. 6, Jun. 2016 pp. 2123-2138.
Wang et al., Database Biosis. Database accession No. PREV200900325303.Abstract Only Mar. 2009: 1 page.
Wang et al., Generation of leukaemia antigen-specific donor lymphocyte infusions powered by streptamer-based selection. Bone Marw Transplantation Mar. 2009;43(Suppl1):S73.
Wang et al., Open-Tubular Capillary Cell Affinity Chromatography: Single and Tandem Blood Cell Separation. Anal Chem. Mar. 15, 2008;80(6):2118-2124.
Wang et al: "Streptamer-based selection of WT1-specific CD8+ T cells for specific donor lymphocyte infusions", Experimental Hematology, vol. 38, No. 11, Nov. 1, 2010 (Nov. 1, 2010 ), pp. 1066-1073.
Xu et al., Aptamer-Based Microfluidic Device for Enrichment, Sorting, and Detection of Multiple Cancer Cells. Anal Chem. Sep. 1, 2009;81(17):7436-7442.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012] 10 pages (Including English translation).
Trickett et al., "T cell stimulation and expansion using anti-CD3/CD28 beads" J. Immunol. Methods (2003) 275(102):251-255.
Aksoy et al., "Human primary T cells: A practical guide," Published on Jun. 19, 2018. Retrieved on Jan. 7, 2020. Retrieved from https://peerj.com/preprints/26993/.
Anonymous, "Optimization of Human T Cell Expansion Protocol: Effects of Early Cell Dilution," Published Oct. 2018. Retrieved on Jan. 7, 2020. Retrieved on https://cdn.stemcell.com/media/files/techbulletin/TB27143-Optimization_of_Human_T_Cell_Expansion_Protocol.pdf?_ga=2.128430788.931468903.1578439383-852611746.1578439383.

Arndt et al., "Analysis of TCR activation kinetics in primary human T cells upon focal or soluble stimulation," J Immunol Methods. Jan. 31, 2013;387(1-2):276-83.
Berg et al., "Sustained TCRsignaling is required for mitogen-activated protein kinase activation anddegranulation by cytotoxic T lymphocytes." 1998. J. Immunol. 161(6), 2919-2924.
Berger et al., "Adoptive transfer of effector CD8 T cells derived from central memory cells establishes persistent T cell memory in primates." (2008) J Clin Invest 118(1): 294-305.
Birnbaum et al., "Molecular architecture of the αβ T cell receptor-CD3 complex." Proc Natl Acad Sci U S A. Dec. 9, 2014;111(49):17576-81. doi: 10.1073/pnas.1420936111.
Boerman et al., "Pretargeted radioimmunotherapy of cancer: progress step by step." Journal of Nuclear Medicine, (2003) 44(3); 400-411.
Busch et al., "Differing roles of inflammation and antigen in T cell proliferation and memory generation." J Immunol. (2000) 164(8); 4063-4070.
Carpentier et al., 2009. "T-cell artificial focal triggering tools: linking surface interactions with cell response." PLoS One (2009) 4(3), e4784.
Chang et al., "Identification and selective expansion of functionally superior T cells expressing chimeric antigen receptors," J Transl Med (2015) 13(1):161.
Chen et al., "Biotin IgM Antibodies in Human Blood: A Previously Unknown Factor Eliciting False Results in Biotinylation-Based Immunoassays," Plos One (2012); 7(8); e42376, pp. 1-8.
Choudhuri et al., "Signaling microdomains in T cells." FEBS Lett. (2010) 584(24); 4823-4831.
Clement et al., "Analysis of the monocyte Fc receptors and antibody-mediated cellular interactions required for the induction of T cell proliferation by anti-T3 antibodies." J Immunol. (1985) 135(1): 165-71.
Daniels et al., "Thymic Selection Threshold Defined by Compartmentalization of Ras/MAPK Signalling," Nature. Dec. 7, 2006; 444(7120): 724-729.
Davis et al., "The kinetic-segregation model: TCR triggering and beyond." Nat. Immunol. 7, 803-809 (2006).
Fontaine et al., "Long-Term Stabilization of Maleimide-Thiol Conjugates," Bioconjug Chem (2015) 26(1):145-152 (Pub Date: Dec. 2014).
Garlie et al., "T cells coactivated with immobilized anti-CD3 and anti-CD28 as potential immunotherapy for cancer." J. Immunother. (1999) 22(4); 336-345.
Ghassemi S., "Ultra-Short Manufacturing of Quiescent Chimeric Antigen Receptor T Cells for Adoptive Immunotherapy," Molecular Therapy vol. 27 No. 4S1 Apr. 2019, p. 86.
Huppa et al., "T-cell-antigen recognition and the immunological synapse," Nat. Rev. Immunol. (2003) 3(12); 973-983.
Kato et al., "Development of Rous sarcoma Virus-like Particles Displaying hVV49 scFv for specific targeted drug delievery to human colon carcinoma cells," Pharm Res (2015) 32:3699-3707.
Kim et al., "The ABCs of Artificial Antigen Presentation," Nat Biotechnol Apr. 2004;22(4): 403-10.
Kohanski, R.A., Lane, M.D. "Monovalent avidin affinity columns" Methods Enzymol. 1990;184:194-200.
Lada et al., "Quantitation of Integrated HIV Provirus by Pulsed-Field Gel Electrophoresis and Droplet Digital PCR," J Clin Microbiol (2018) 56(12): e01158-18.
Lenschow et al., "CD28/B7 system of T cell costimulation." Annu Rev Immunol. 1996;14:233-58.
Levine et al., 1997. "Effects of CD28 costimulation on long-term proliferation of CD4+ T cells in the absence of exogenous feeder cells." J. Immunol. (1997) 159(12), 5921-5930.
Li, Y. et al., "Comparison of anti-CD3 and anti-CD28-coated Beads With Soluble anti-CD3 for Expanding Human T Cells: Differing Impact on CD8 T Cell Phenotype and Responsiveness to Restimulation," J Transl Med (2010) 8: 104.
Lu et al., "A rapid cell expansion process for production of engineered autologous CAR-T cell therapies," Human Gene Therapy Methods (2016) 27(6):209-218.

(56) References Cited

OTHER PUBLICATIONS

Lyon et al., "Self-hydrolyzing maleimides improve the stability and pharmacological properties of antiody-drug conjugates," Nature Biotechnology, vol. 32, Sep. 7, 2014, p. 1059-1062.
Mehlhop-Williams et al., "Memory CD8+ T cells exhibit increased antigen threshold requirements for recall proliferation." J Exp Med. (2014) 211(2): 345-56. doi: 10.1084/jem.20131271.
Meyer et al., "Biodegradable nanoellipsoidal artificial antigen presenting cells for antigen specific T-cell activation." Small. (2015) 11(13):1519-1525. doi: 10.1002/smll.201402369.
Neeson et al., "Ex Vivo Culture of Chimeric Antigen Receptor T Cells Generates Functional CD8+ T Cells With Effector and Central Memory-Like Phenotype," Gene Ther (2010) 17(9): 1105-16.
Okamoto et al., "A Promising Vector for TCR Gene Therapy: Differential Effect of siRNA, 2A Peptide, and Disulfide Bond on the Introduced TCR Expression," Mol Ther Nucleic Acids. (2012) 1(12): e63. 11 pages.
Palmer et al., "Affinity Threshold for Thymic Selection Through a T-cell Receptor-Co-Receptor Zipper," Nat Rev Immunol (2009) 9(3): 207-213.
Pearce EL. "Metabolism in T cell activation and differentiation," Curr. Opin. Immunol. (2010) 22(3), 314-320.
Poltorak et al., "TCR activation kinetics and feeDynaBeads™ ack regulation in primary human T cells." Cell Commun Signal. Jan. 14, 2013;11:4. doi: 10.1186/1478-811X-11-4.
Pozarowski et al., "Analysis of Cell Cycle by Flow Cytometry," Methods Mol Biol. (2004) 281: 301-311.
Rapoport et al., "Restoration of immunity in lymphopenic individuals with cancer by vaccination and adoptive T-cell transfer." Nat Med. (2005) 11(11):1230-1237.
Riddell et al., "The use of anti-CD3 and anti-CD28 monoclonal antibodies to clone and expand human antigen-specific T cells." J Immunol Methods. (1990) 128(2): 189-201.
Rossy et al., "How Does the Kinase Lck Phosphorylate the T Cell Receptor? Spatial Organization as a Regulatory Mechanism," Front Immunol. (2012) 3:167.
Rudd et al., "CD28 and CTLA-4 coreceptor expression and signal transduction." Immunol Rev. (2009) 229(1); 12-26.
Rybak, J.N., et al. "Purification of biotinylated proteins on streptavidin resin: a protocol for quantitative elution," Proteomics. 2004 4(8): 2296-2299.
Schmidt et al., "Development of the Twin-Strep-tag and its application for purification of recombinant proteins from cell culture supernatants." Protein Expression and Purification (2013) 92(1); 54-61.
Schmidt et al., "Molecular Interaction Between the Strep-tag Affinity Peptide and its Cognate Target, Streptavidin." Mol. Biol. (1996) 255(5); 753-766.
Schmidt et al., "The random peptide library-assisted engineering of a C-terminal affinity peptide, useful for the detection and purification of a functional Ig Fv fragment." Protein Eng. (1993) 6(1); 109-122.
Tumey et al., "Mild Method for Succinimide Hydrolysis on ADCs: Impact on ADC Potency, Stability, Exposure, and Efficacy," Bioconjug Chem. (2014) 25(10):1871-1880.
Turtle et al., "Genetically retargeting CD8+ lymphocyte subsets for cancer immunotherapy." Curr Opin Immunol. (2011) 23(2); 299-305.
van Panhuys et al., "T-cell-receptor-dependent signal intensity dominantly controls CD4(+) T cell polarization In Vivo." Immunity. (2014) 41(1): 63-74. doi: 10.1016/j.immuni.2014.06.003.
van Stipdonk et al., "Naïve CTLs require a single brief period of antigenic stimulation for clonal expansion and differentiation." Nat Immunol. (2001) 2(5): 423-429.
Vormittag et al., "A Guide to Manufacturing CAR T Cell Therapies," Curr Opin Biotechnol (2018) 53: 164-181.
Wang et al., "A transgene-encoded cell surface polypeptide for selection, in vivo tracking, and ablation of engineered cells." Blood. (2011) 118(5):1255-1263.
Wang et al., "Dynamics of proximal signaling events after TCR/CD8-mediated induction of proliferation or apoptosis in mature CD8+ T cells." J. Immunol. (2008) 180(10); 6703-6712.
Wigler, M. et al. (May 1977). "Transfer of Purified Herpes Virus Thymidine Kinase Gene to Cultured Mouse Cells", Cell 2(11):223-232.
Wu, R. et al. (Mar. 2012). "Adoptive T-cell Therapy Using Autologous Tumor-infiltrating Lymphocytes for Metastatic Melanoma: Current Status and Future Outlook", Cancer J. 18(2):160-175.
Wu, S.C. et al. (Jun. 17, 2005). "Engineering soluble monomeric streptavidin with reversible biotin binding capability", J. Biol. Chem.280(24):23225-23231.
Xu et al., "Closely Related T-memory Stem Cells Correlate With in Vivo Expansion of CAR.CD19-T Cells and Are Preserved by IL-7 and IL-15," Blood (2014) 123 (24): 3750-3759.
Xu et al., "Multiparameter Comparative Analysis Reveals Differential Impacts of Various Cytokines on CART Cell Phenotype and Function Ex Vivo and in Vivo," Oncotarget (2016) 7(50): 82354-82368.
Yang et al., "In vitro generated anti-tumor T lymphocytes exhibit distinct subsets mimicking in vivo antigen-experienced cells." Cancer Immunol Immunother (2011) 60(5): 739-749.
Yang et al., "Targeting lentiviral vectors to specific cell types in vivo," PNAS USA (2006) 103(31):11479-11484.
Yarilin, "Immunology principles," M. Medicine (1999) 184-195, 339-347 (English Translation included).
Zhang et al., "LAT: the ZAP-70 tyrosine kinase substrate that links T cell receptor to cellular activation," Cell (1998) 92(1):83-92.
Zhang, M. et al. (Aug. 7, 2015). "A novel approach to make homogeneous protease-stable monovalent streptavidin", Biochem Biophys Res Commun. 463(4):1059-1063.
Zhao et al., "Development of the First World Health Organization Lentiviral Vector Standard: Toward the Production Control and Standardization of Lentivirus-Based Gene Therapy Products," Hum Gene Ther Methods (2017) 28 (4): 205-214.
Zhou X et al., "Lentivirus-mediated gene transfer and expression in established human tumor antigen-specific cytotoxic T cells and primayr unstimulated T cels," Human Gene Therapy, vol. 14 No. 11, Jul. 20, 2003 pp. 1089-1105.
Zufferey et al. "Self-Inactivating Lentivirus Vector for Safe and Efficient In Vivo Gene Delivery," J. Virol (1998) 72(12):9873-9880.
Zufferey et al. "Woodchuck Hepatitis Virus Posttranscriptional Regulatory Element Enhances Expression of Transgenes Delivered by Retroviral Vectors" 1999. J. Virol. vol. 73, No. 4, pp. 2886-2892.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese).
Kong et al., "Isolation of breast cancer stem cell and screening of specific polypeptide bonding to it," Chinese Journal of Cancer Prevention and Control (2013) 20(24):1892-1895.
Wang et al., "Open-tubular capillary cell affinity chromatography: single and tandem blood cell separation," Anal Chem (2008) 80(6):2118-2124.
U.S. Appl. No. 17/289,690, filed Apr. 28, 2021, by Germeroth et al. (Copy not provided).
Bambauer et al., "LDL-apheresis: technical and clinical aspects," The Scientific World Journal (2012).
Godawat et al., "Period counter-current chromatography—design and operational considerations for integrated and continuous purification of proteins," Biotechnology journal (2012) 7(12):1496-1508.
Korndorfer et al., "Improved affinity of engineered streptavidin for the Strep-tag 11 peptide is due to a fixed open conformation of the lid-like loop at the binding site," Protein Sci (2002) 11:883-893.
Kubben et al. "Identification of differential protein interactors of lamin A and progerin," Nucleus (2010) 1(6): 513-525.
Kumar et al., "Integrated bioprocess for the production and isolation of urokinase from animal cell culture using supermacroporous cryogel matrices," Biotechnology and Bioengineering (2006) 93(4):636-646.
Matic et al., "Fine Tuning and Efficient T Cell Activation with Stimulatory aCD3 Nanoarrays," Nano Letters (2013) 13:5090-5097.

(56) References Cited

OTHER PUBLICATIONS

Schroeder, Nach Zellen Angeln. Faszination Forschung Jun. 30, 2010:28-37 Retrieved from the Internet: URL:http://portal.mytum.de/pressestelle/faszination-forschung/2010nr6/index (Including English translation).

Turka et al., "CD28 is an Inducible T Cell Surface Antigen That Transduces a Proliferative Signal in CD3+ Mature Thymocytes," J Immunol (1990) 144:1646-1653.

Xia et al., "Enrichment of haploid spermatids in mice by flow sorting," Natl Journal of Andrology (2014) 20(2):106-110.

Walter et al., "Cutting edge: Predetermined Avidity of Human CD8 T cells expanded on calibrated MHC/Anti-CD28-Coated Microspheres," J Immunol (2003) 171:4973-4978.

* cited by examiner

Figure 4A
(A)
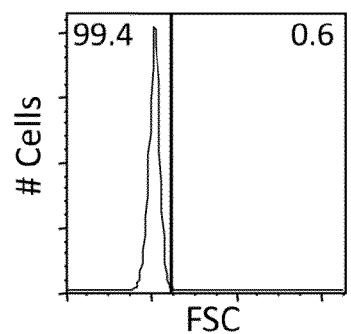
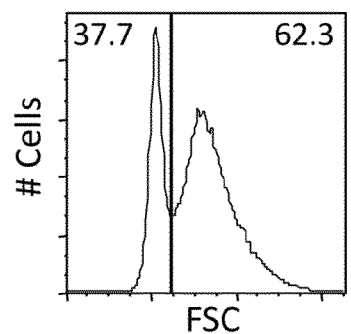
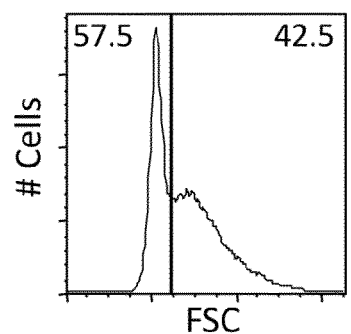
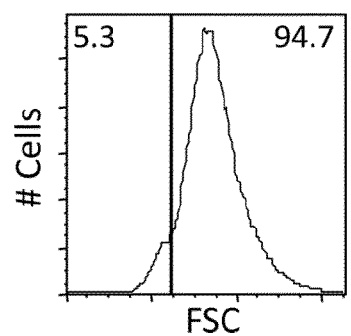

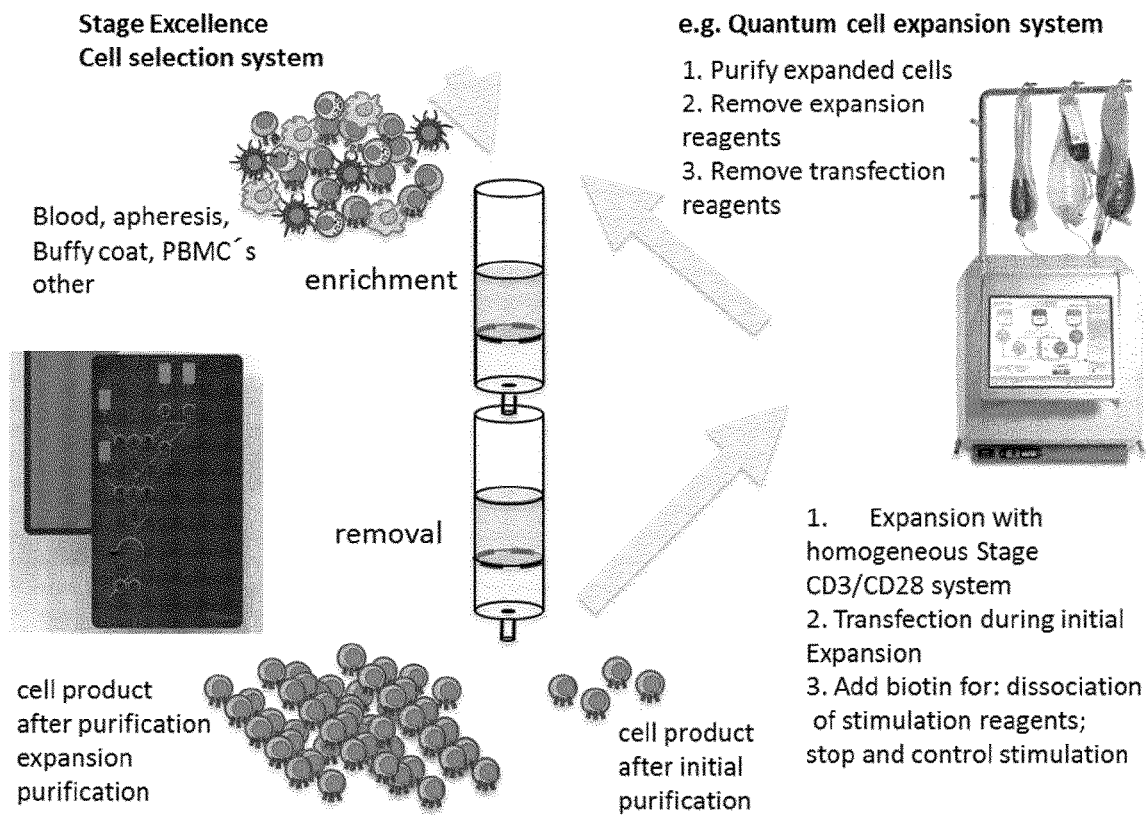

Figure 9b

Coupling of CATCH selection with homogeneous cell expansion

- Closed system enables to shuttle cells back and fro from purification to expansion in one process

- Expansion with homogeneous Stage CD3/CD28 (no beads involved) reagents ideally suited for this closed system since no magnetic beads have to be removed

- Transfection can be integrated in the closed process

- Add biotin for: dissociation of stimulation reagents stop and control stimulation

- Homogeneous assay enable successive generic (CD3/CD28) and receptor-specific expansion

Figure 15
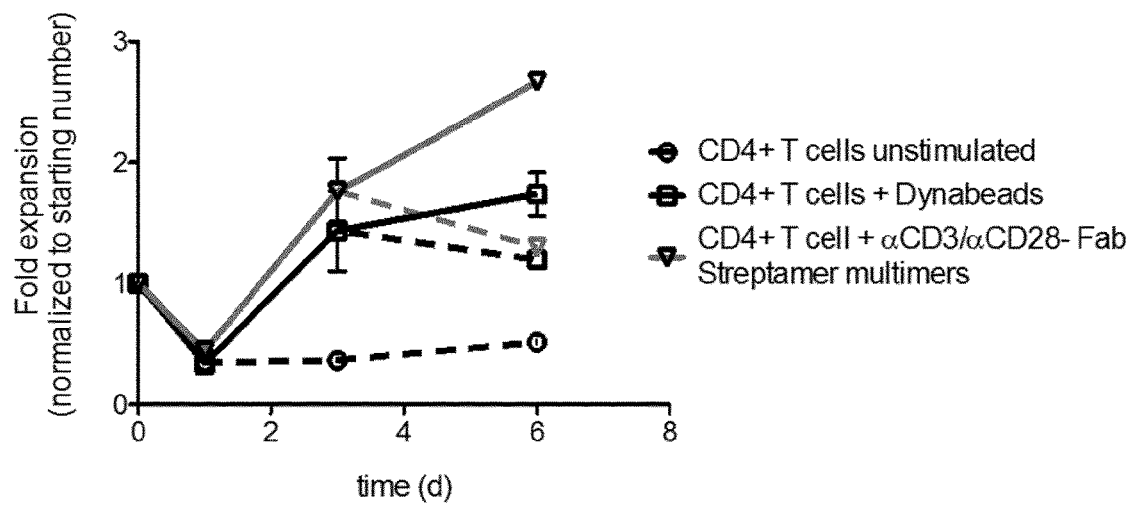
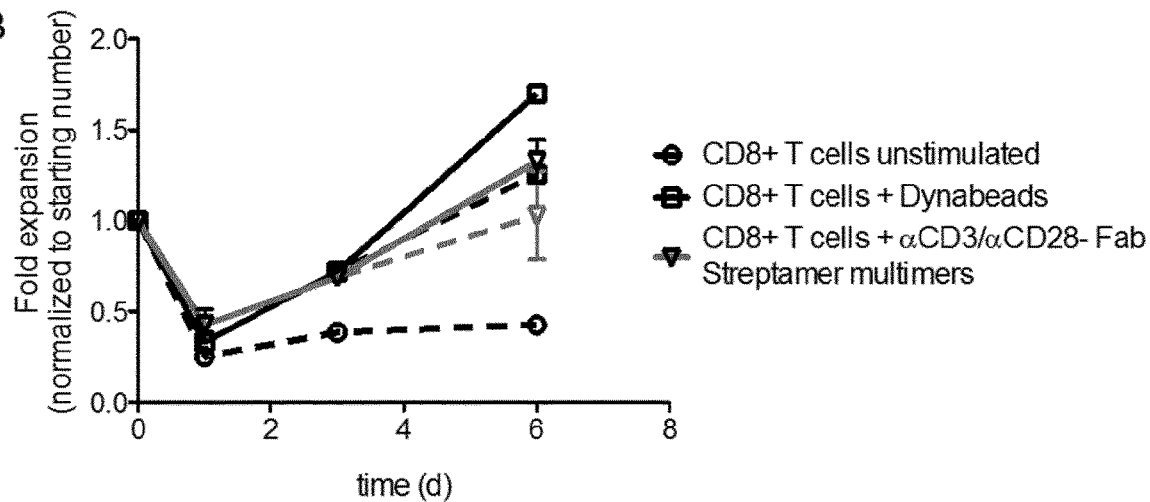

A

Figure 21
A
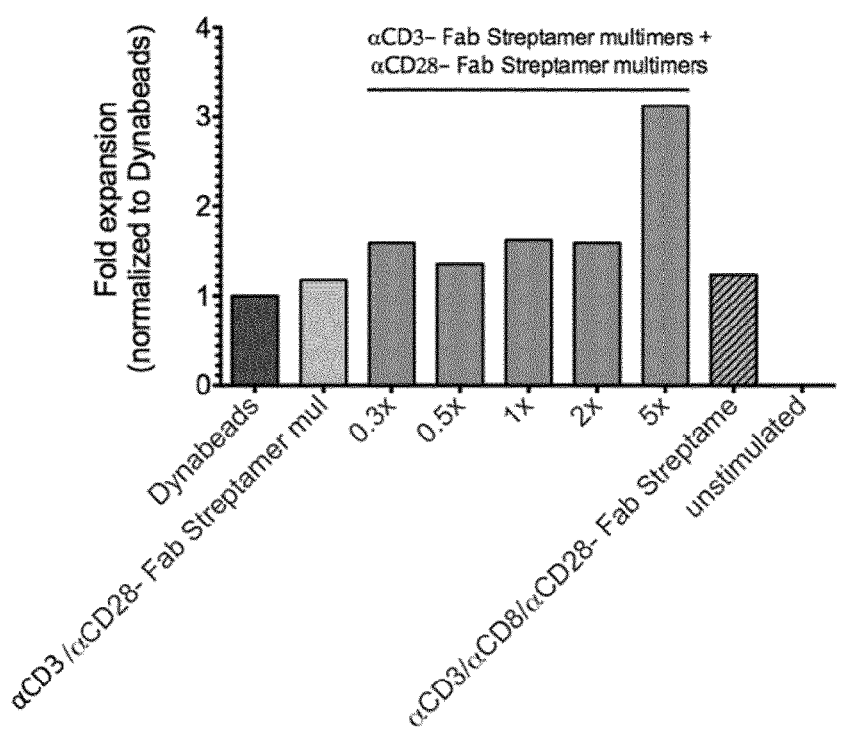
B
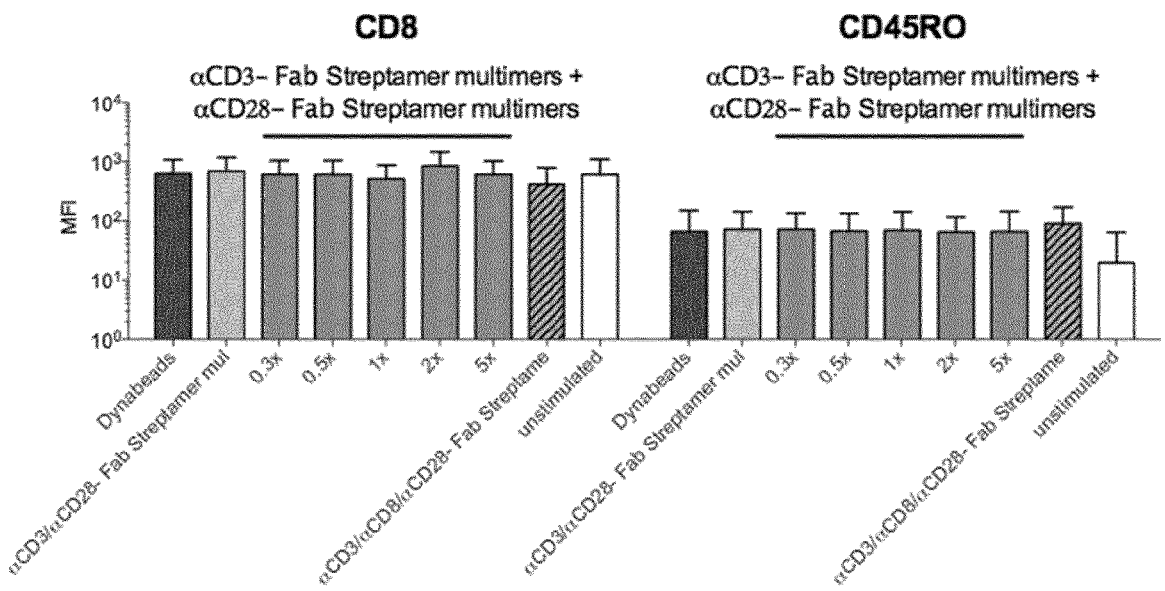

Figure 23
A
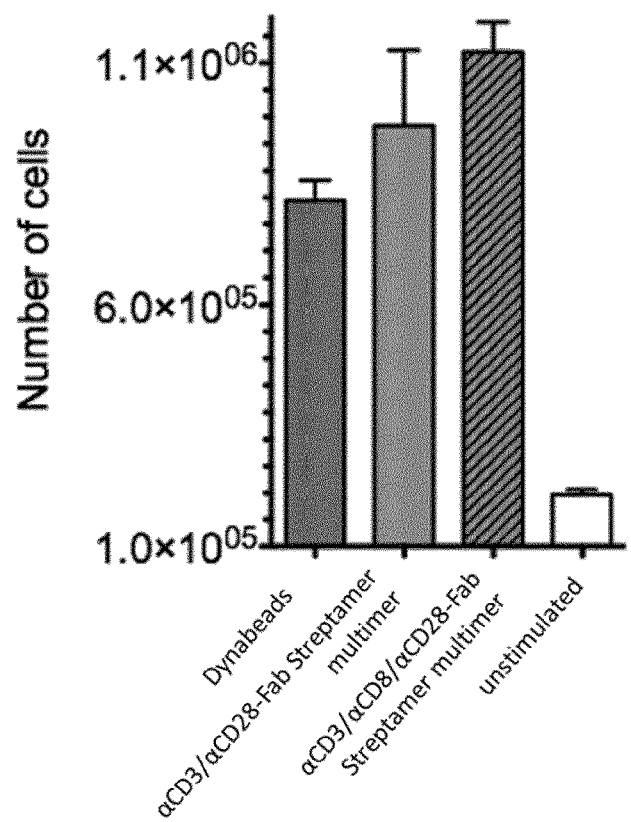
B
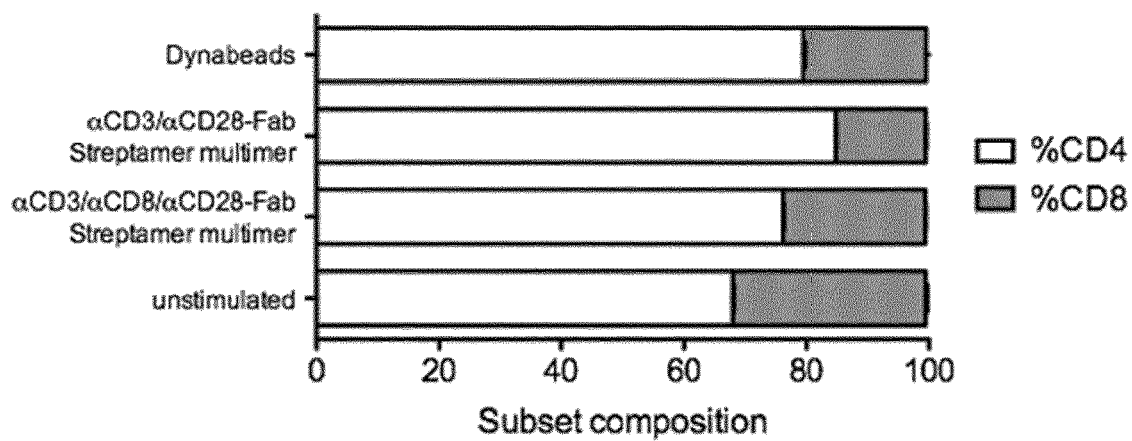

SEQUENCE LISTING

```
<160> NUMBER OF SEQ ID NOS: 27

<210> SEQ ID NO 1
<211> LENGTH: 8
<212> TYPE: PRT
<213> ORGANISM: artificial
<220> FEATURE:
<223> OTHER INFORMATION: Synthetic
<220> FEATURE:
<223> OTHER INFORMATION: Strep-tag

<400> SEQUENCE: 1

Trp Ser His Pro Gln Phe Glu Lys
1               5

<210> SEQ ID NO 2
<211> LENGTH: 4
<212> TYPE: PRT
<213> ORGANISM: artificial
<220> FEATURE:
<223> OTHER INFORMATION: Synthetic
```

```
<220> FEATURE:
<223> OTHER INFORMATION: streptavidin mutein (analog) 1

<400> SEQUENCE: 2

Val Thr Ala Arg
1

<210> SEQ ID NO 3
<211> LENGTH: 4
<212> TYPE: PRT
<213> ORGANISM: artificial
<220> FEATURE:
<223> OTHER INFORMATION: Synthetic
<220> FEATURE:
<223> OTHER INFORMATION: streptavidin mutein (analog) 2

<400> SEQUENCE: 3

Ile Gly Ala Arg
1

<210> SEQ ID NO 4
<211> LENGTH: 28
<212> TYPE: PRT
<213> ORGANISM: artificial
<220> FEATURE:
<223> OTHER INFORMATION: Synthetic
<220> FEATURE:
<223> OTHER INFORMATION: di-tag3

<400> SEQUENCE: 4

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 5
<211> LENGTH: 24
<212> TYPE: PRT
<213> ORGANISM: artificial
<220> FEATURE:
<223> OTHER INFORMATION: Synthetic
<220> FEATURE:
<223> OTHER INFORMATION: di-tag2

<400> SEQUENCE: 5

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 6
<211> LENGTH: 9
<212> TYPE: PRT
<213> ORGANISM: artificial
<220> FEATURE:
<223> OTHER INFORMATION: Synthetic
<220> FEATURE:
<223> OTHER INFORMATION: immediate-early 1 protein (amino acids 309-317)

<400> SEQUENCE: 6

Cys Arg Val Leu Cys Cys Tyr Val Leu
1               5

<210> SEQ ID NO 7
<211> LENGTH: 30
<212> TYPE: PRT
<213> ORGANISM: artificial
```

```
-continued

<220> FEATURE:
<223> OTHER INFORMATION: Synthetic
<220> FEATURE:
<223> OTHER INFORMATION: Twin-Strep-tag

<400> SEQUENCE: 7

Ser Ala Trp Ser His Pro Gln Phe Glu Lys Gly Gly Gly Ser Gly Gly
1               5                   10                  15
Gly Ser Gly Gly Ser Ala Trp Ser His Pro Gln Phe Glu Lys
            20                  25                  30

<210> SEQ ID NO 8
<211> LENGTH: 9
<212> TYPE: PRT
<213> ORGANISM: artificial
<220> FEATURE:
<223> OTHER INFORMATION: Synthetic
<220> FEATURE:
<223> OTHER INFORMATION: pp65 epitope of CMV (amino acids 341-350)

<400> SEQUENCE: 8

Gln Tyr Asp Pro Val Ala Ala Leu Phe
1               5

<210> SEQ ID NO 9
<211> LENGTH: 11
<212> TYPE: PRT
<213> ORGANISM: artificial
<220> FEATURE:
<223> OTHER INFORMATION: Synthetic
<220> FEATURE:
<223> OTHER INFORMATION: pp65 epitope of CMV (amino acids 265-274)

<400> SEQUENCE: 9

Arg Pro His Glu Arg Asn Gly Phe Thr Val Leu
1               5                   10

<210> SEQ ID NO 10
<211> LENGTH: 11
<212> TYPE: PRT
<213> ORGANISM: artificial
<220> FEATURE:
<223> OTHER INFORMATION: Synthetic
<220> FEATURE:
<223> OTHER INFORMATION: hexon 5 epitope of adenovirus (amino acids
      114-124)

<400> SEQUENCE: 10

Lys Pro Tyr Ser Gly Thr Ala Tyr Asn Ala Leu
1               5                   10

<210> SEQ ID NO 11
<211> LENGTH: 9
<212> TYPE: PRT
<213> ORGANISM: artificial
<220> FEATURE:
<223> OTHER INFORMATION: Synthetic
<220> FEATURE:
<223> OTHER INFORMATION: HA-tag

<400> SEQUENCE: 11

Tyr Pro Tyr Asp Val Pro Asp Tyr Ala
1               5

<210> SEQ ID NO 12
<211> LENGTH: 11
<212> TYPE: PRT
<213> ORGANISM: artificial
```

```
<220> FEATURE:
<223> OTHER INFORMATION: Synthetic
<220> FEATURE:
<223> OTHER INFORMATION: VSV-G-tag

<400> SEQUENCE: 12

Tyr Thr Asp Ile Glu Met Asn Arg Leu Gly Lys
1               5                   10

<210> SEQ ID NO 13
<211> LENGTH: 11
<212> TYPE: PRT
<213> ORGANISM: artificial
<220> FEATURE:
<223> OTHER INFORMATION: Synthetic
<220> FEATURE:
<223> OTHER INFORMATION: HSV-tag

<400> SEQUENCE: 13

Gln Pro Glu Leu Ala Pro Glu Asp Pro Glu Asp
1               5                   10

<210> SEQ ID NO 14
<211> LENGTH: 10
<212> TYPE: PRT
<213> ORGANISM: artificial
<220> FEATURE:
<223> OTHER INFORMATION: Synthetic
<220> FEATURE:
<223> OTHER INFORMATION: T7 epitope

<400> SEQUENCE: 14

Ala Ser Met Thr Gly Gly Gln Gln Met Gly
1               5                   10

<210> SEQ ID NO 15
<211> LENGTH: 10
<212> TYPE: PRT
<213> ORGANISM: artificial
<220> FEATURE:
<223> OTHER INFORMATION: Synthetic
<220> FEATURE:
<223> OTHER INFORMATION: myc epitope

<400> SEQUENCE: 15

Glu Gln Lys Leu Ile Ser Glu Glu Asp Leu
1               5                   10

<210> SEQ ID NO 16
<211> LENGTH: 14
<212> TYPE: PRT
<213> ORGANISM: artificial
<220> FEATURE:
<223> OTHER INFORMATION: Synthetic
<220> FEATURE:
<223> OTHER INFORMATION: V5-tag

<400> SEQUENCE: 16

Gly Lys Pro Ile Pro Asn Pro Leu Leu Gly Leu Asp Ser Thr
1               5                   10

<210> SEQ ID NO 17
<211> LENGTH: 119
<212> TYPE: PRT
<213> ORGANISM: mus musculus

<400> SEQUENCE: 17

Gln Val Gln Leu Gln Gln Ser Gly Ala Glu Leu Ala Arg Pro Gly Ala
```

```
            1               5                  10                 15
         Ser Val Lys Met Ser Cys Lys Ala Ser Gly Tyr Thr Phe Thr Arg Tyr
                        20                  25                  30

Thr Met His Trp Val Lys Gln Arg Pro Gly Gln Gly Leu Glu Trp Ile
                        35                  40                  45

Gly Tyr Ile Asn Pro Ser Arg Gly Tyr Thr Asn Tyr Asn Gln Lys Phe
                        50                  55                  60

Lys Asp Lys Ala Thr Leu Thr Thr Asp Lys Ser Ser Ser Thr Ala Tyr
         65                  70                  75                  80

Met Gln Leu Ser Ser Leu Thr Ser Glu Asp Ser Ala Val Tyr Tyr Cys
                        85                  90                  95

Ala Arg Tyr Tyr Asp Asp His Tyr Cys Leu Asp Tyr Trp Gly Gln Gly
                        100                 105                 110

Thr Thr Leu Thr Val Ser Ser
                        115

<210> SEQ ID NO 18
<211> LENGTH: 106
<212> TYPE: PRT
<213> ORGANISM: mus musculus

<400> SEQUENCE: 18

Gln Ile Val Leu Thr Gln Ser Pro Ala Ile Met Ser Ala Ser Pro Gly
         1               5                  10                 15

Glu Lys Val Thr Met Thr Cys Ser Ala Ser Ser Ser Val Ser Tyr Met
                        20                  25                  30

Asn Trp Tyr Gln Gln Lys Ser Gly Thr Ser Pro Lys Arg Trp Ile Tyr
                        35                  40                  45

Asp Thr Ser Lys Leu Ala Ser Gly Val Pro Ala His Phe Arg Gly Ser
                        50                  55                  60

Gly Ser Gly Thr Ser Tyr Ser Leu Thr Ile Ser Gly Met Glu Ala Glu
         65                  70                  75                  80

Asp Ala Ala Thr Tyr Tyr Cys Gln Gln Trp Ser Ser Asn Pro Phe Thr
                        85                  90                  95

Phe Gly Ser Gly Thr Lys Leu Glu Ile Asn
                        100                 105

<210> SEQ ID NO 19
<211> LENGTH: 116
<212> TYPE: PRT
<213> ORGANISM: mus musculus

<400> SEQUENCE: 19

Leu Gln Gln Ser Gly Ala Glu Leu Val Lys Pro Gly Ala Ser Val Arg
         1               5                  10                 15

Leu Ser Cys Lys Ala Ser Gly Tyr Thr Phe Thr Glu Tyr Ile Ile His
                        20                  25                  30

Trp Ile Lys Leu Arg Ser Gly Gln Gly Leu Glu Trp Ile Gly Trp Phe
                        35                  40                  45

Tyr Pro Gly Ser Asn Asp Ile Gln Tyr Asn Ala Lys Phe Lys Gly Lys
                        50                  55                  60

Ala Thr Leu Thr Ala Asp Lys Ser Ser Ser Thr Val Tyr Met Glu Leu
         65                  70                  75                  80

Thr Gly Leu Thr Ser Glu Asp Ser Ala Val Tyr Phe Cys Ala Arg Arg
                        85                  90                  95

Asp Asp Phe Ser Gly Tyr Asp Ala Leu Pro Tyr Trp Gly Gln Gly Thr
```

Met Val Thr Val
        115

<210> SEQ ID NO 20
<211> LENGTH: 108
<212> TYPE: PRT
<213> ORGANISM: mus musculus

<400> SEQUENCE: 20

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105

<210> SEQ ID NO 21
<211> LENGTH: 314
<212> TYPE: PRT
<213> ORGANISM: artificial
<220> FEATURE:
<223> OTHER INFORMATION: Synthetic
<220> FEATURE:
<223> OTHER INFORMATION: HLA-A2402

<400> SEQUENCE: 21

Met Gly Ser His Ser Met Arg Tyr Phe Ser Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Glu Glu
    50                  55                  60

Thr Gly Lys Val Lys Ala His Ser Gln Thr Asp Arg Glu Asn Leu Arg
65                  70                  75                  80

Ile Ala Leu Arg Tyr Tyr Asn Gln Ser Glu Ala Gly Ser His Thr Leu
                85                  90                  95

Gln Met Met Phe Gly Cys Asp Val Gly Ser Asp Gly Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Ile Thr
    130                 135                 140

Lys Arg Lys Trp Glu Ala Ala His Val Ala Glu Gln Arg Ala Tyr
145                 150                 155                 160

Leu Glu Gly Thr Cys Val Asp Gly Leu Arg Arg Tyr Leu Glu Asn Gly
                165                 170                 175

```
Lys Glu Thr Leu Gln Arg Thr Asp Pro Pro Lys Thr His Met Thr His
                180                 185                 190

His Pro Ile Ser Asp His Glu Ala Thr Leu Arg Cys Trp Ala Leu Gly
            195                 200                 205

Phe Tyr Pro Ala Glu Ile Thr Leu Thr Trp Gln Arg Asp Gly Glu Asp
        210                 215                 220

Gln Thr Gln Asp Thr Glu Leu Val Glu Thr Arg Pro Ala Gly Asp Gly
225                 230                 235                 240

Thr Phe Gln Lys Trp Ala Ala Val Val Pro Ser Gly Glu Glu Gln
                245                 250                 255

Arg Tyr Thr Cys His Val Gln His Glu Gly Leu Pro Lys Pro Leu Thr
            260                 265                 270

Leu Arg Trp Glu Pro Pro Ser Gly Ser Ser Ala Trp Ser His Pro
        275                 280                 285

Gln Phe Glu Lys Gly Gly Gly Ser Gly Gly Gly Ser Gly Gly Gly Ser
        290                 295                 300

Ser Ala Trp Ser His Pro Gln Phe Glu Lys
305                 310
```

<210> SEQ ID NO 22
<211> LENGTH: 314
<212> TYPE: PRT
<213> ORGANISM: artificial
<220> FEATURE:
<223> OTHER INFORMATION: Synthetic
<220> FEATURE:
<223> OTHER INFORMATION: HLA-B0702

<400> SEQUENCE: 22

```
Met Gly Ser His Ser Met Arg Tyr Phe Tyr Thr Ser Val Ser Arg Pro
1               5                   10                  15

Gly Arg Gly Glu Pro Arg Phe Ile Ser Val Gly Tyr Val Asp Asp Thr
            20                  25                  30

Gln Phe Val Arg Phe Asp Ser Asp Ala Ala Ser Pro Arg Glu Glu Pro
        35                  40                  45

Arg Ala Pro Trp Ile Glu Gln Glu Gly Pro Glu Tyr Trp Asp Arg Asn
    50                  55                  60

Thr Gln Ile Tyr Lys Ala Gln Ala Gln Thr Asp Arg Glu Ser Leu Arg
65                  70                  75                  80

Asn Leu Arg Gly Tyr Tyr Asn Gln Ser Glu Ala Gly Ser His Thr Leu
                85                  90                  95

Gln Ser Met Tyr Gly Cys Asp Val Gly Pro Asp Gly Arg Leu Leu Arg
            100                 105                 110

Gly His Asp Gln Tyr Ala Tyr Asp Gly Lys Asp Tyr Ile Ala Leu Asn
        115                 120                 125

Glu Asp Leu Arg Ser Trp Thr Ala Ala Asp Thr Ala Ala Gln Ile Thr
    130                 135                 140

Gln Arg Lys Trp Glu Ala Ala Arg Glu Ala Glu Gln Arg Arg Ala Tyr
145                 150                 155                 160

Leu Glu Gly Glu Cys Val Glu Trp Leu Arg Arg Tyr Leu Glu Asn Gly
                165                 170                 175

Lys Asp Lys Leu Glu Arg Ala Asp Pro Pro Lys Thr His Val Thr His
            180                 185                 190

His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
    210                 215                 220
```

```
                210                 215                 220
Gln Thr Gln Asp Thr Glu Leu Val Glu Thr Arg Pro Ala Gly Asp Arg
225                 230                 235                 240

Thr Phe Gln Lys Trp Ala Ala Val Val Pro Ser Gly Glu Glu Gln
                245                 250                 255

Arg Tyr Thr Cys His Val Gln His Glu Gly Leu Pro Lys Pro Leu Thr
                260                 265                 270

Leu Arg Trp Glu Pro Pro Ser Gly Ser Ser Ala Trp Ser His Pro
                275                 280                 285

Gln Phe Glu Lys Gly Gly Gly Ser Gly Gly Gly Ser Gly Gly Gly Ser
                290                 295                 300

Ser Ala Trp Ser His Pro Gln Phe Glu Lys
305                 310

<210> SEQ ID NO 23
<211> LENGTH: 321
<212> TYPE: PRT
<213> ORGANISM: artificial
<220> FEATURE:
<223> OTHER INFORMATION: Synthetic
<220> FEATURE:
<223> OTHER INFORMATION: HLA-C0702

<400> SEQUENCE: 23

Met Ala Leu Thr Glu Thr Trp Ala Cys Ser His Ser Met Arg Tyr Phe
1               5                   10                  15

Asp Thr Ala Val Ser Arg Pro Gly Arg Gly Glu Pro Arg Phe Ile Ser
                20                  25                  30

Val Gly Tyr Val Asp Asp Thr Gln Phe Val Arg Phe Asp Ser Asp Ala
                35                  40                  45

Ala Ser Pro Arg Gly Glu Pro Arg Ala Pro Trp Val Glu Gln Glu Gly
    50                  55                  60

Pro Glu Tyr Trp Asp Arg Glu Thr Gln Lys Tyr Lys Arg Gln Ala Gln
65                  70                  75                  80

Ala Asp Arg Val Ser Leu Arg Asn Leu Arg Gly Tyr Tyr Asn Gln Ser
                85                  90                  95

Glu Asp Gly Ser His Thr Leu Gln Arg Met Ser Gly Cys Asp Leu Gly
                100                 105                 110

Pro Asp Gly Arg Leu Leu Arg Gly Tyr Asp Gln Ser Ala Tyr Asp Gly
            115                 120                 125

Lys Asp Tyr Ile Ala Leu Asn Glu Asp Leu Arg Ser Trp Thr Ala Ala
            130                 135                 140

Asp Thr Ala Ala Gln Ile Thr Gln Arg Lys Leu Glu Ala Ala Arg Ala
145                 150                 155                 160

Ala Glu Gln Leu Arg Ala Tyr Leu Glu Gly Thr Cys Val Glu Trp Leu
                165                 170                 175

Arg Arg Tyr Leu Glu Asn Gly Lys Glu Thr Leu Gln Arg Ala Glu Pro
            180                 185                 190

Pro Lys Thr His Val Thr His His Pro Leu Ser Asp His Glu Ala Thr
            195                 200                 205

Leu Arg Cys Trp Ala Leu Gly Phe Tyr Pro Ala Glu Ile Thr Leu Thr
            210                 215                 220

Trp Gln Arg Asp Gly Glu Asp Gln Thr Gln Asp Thr Glu Leu Val Glu
225                 230                 235                 240

Thr Arg Pro Ala Gly Asp Gly Thr Phe Gln Lys Trp Ala Ala Val Val
                245                 250                 255
```

Val Pro Ser Gly Gln Glu Gln Arg Tyr Thr Cys His Met Gln His Glu
            260                 265                 270

Gly Leu Gln Glu Pro Leu Thr Leu Ser Trp Glu Pro Ser Ser Gln Pro
        275                 280                 285

Thr Ile Gly Ser Ala Trp Ser His Pro Gln Phe Glu Lys Gly Gly Gly
    290                 295                 300

Ser Gly Gly Gly Ser Gly Gly Ser Ala Trp Ser His Pro Gln Phe Glu
305                 310                 315                 320

Lys

<210> SEQ ID NO 24
<211> LENGTH: 100
<212> TYPE: PRT
<213> ORGANISM: homo sapiens

<400> SEQUENCE: 24

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met
            100

<210> SEQ ID NO 25
<211> LENGTH: 118
<212> TYPE: PRT
<213> ORGANISM: mus musculus

<400> SEQUENCE: 25

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
            115

<210> SEQ ID NO 26
<211> LENGTH: 111

```
<212> TYPE: PRT
<213> ORGANISM: mus musculus

<400> SEQUENCE: 26

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Phe Asp
                20                  25                  30

Gly Asp Ser Phe Met Asn Trp Tyr Gln Gln Lys Pro Gly Gln Pro Pro
            35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 27
<211> LENGTH: 283
<212> TYPE: PRT
<213> ORGANISM: artificial
<220> FEATURE:
<223> OTHER INFORMATION: Synthetic
<220> FEATURE:
<223> OTHER INFORMATION: human CD19 extracellular domain with His-Tag

<400> SEQUENCE: 27

Pro Glu Glu Pro Leu Val Val Lys Val Glu Glu Gly Asp Asn Ala Val
 1               5                  10                  15

Leu Gln Cys Leu Lys Gly Thr Ser Asp Gly Pro Thr Gln Gln Leu Thr
                20                  25                  30

Trp Ser Arg Glu Ser Pro Leu Lys Pro Phe Leu Lys Leu Ser Leu Gly
            35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
    115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
    195                 200                 205

Leu Glu Leu Lys Asp Asp Arg Pro Ala Arg Asp Met Trp Val Met Glu
210                 215                 220
```

```
Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
            245                 250                 255

Ala Arg Pro Val Leu Trp His Trp Leu Leu Arg Thr Gly Gly Trp Lys
            260                 265                 270

Ala His His His His His His His His
        275                 280
```

METHODS, KITS AND APPARATUS FOR EXPANDING A POPULATION OF CELLS

CROSS-REFERENCE TO RELATED APPLICATIONS

This application is a US National Stage of International Application No. PCT/EP2015/058339 filed 16 Apr. 2015, which claims the benefit of priority to U.S. provisional patent application 61/980,506 "Methods, Kits And Apparatus For Expanding A Population Of Cells" filed with the US Patent and Trademark Office on 16 Apr. 2014, the contents of these applications are hereby incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735042004000_SeqList.txt, date recorded: Oct. 13, 2016, size: 22,438 bytes).

FIELD OF THE INVENTION

The present invention relates to the expansion (proliferation) of a population of cells such as a population of lymphocytes. The invention in general provides novel methods and reagents for the expansion (proliferation) of cell populations that require binding of a receptor binding molecule (such as a first agent as described herein) to a receptor molecule on the surface of the cells, thereby providing a primary activation signal to the cells. The invention employs a multimerization reagent that has immobilized thereon (bound thereto) a first agent that provides a primary activation signal to the cells. This primary activation signal may as such be sufficient to activate the cells to expand/proliferate. This first agent can either be bound reversibly or also irreversibly to the multimerization reagent. The multimerization reagent may have immobilized thereon (bound thereto) also a second agent that stimulates an accessory molecule on the surface of the cells. The second agent, when binding to the accessory molecule on the surface on the surface of the cells, may thereby stimulate the activated cells to expand. Also this second agent can either be bound reversibly or also irreversibly to the multimerization reagent. The multimerization agent may either be immobilized on a solid support or soluble. In one aspect, the method disclosed herein is a serial expansion of a population of cells in which a complete population of lymphocytes is stimulated/expanded, the reagents necessary for the expansion are then removed by chromatography on a suitable stationary phase and the expanded/stimulated cells are optionally transfected with e.g. a T cell receptor or a chimeric antigen receptor (CAR) and subjected to a second stimulation expansion with a different stimulatory molecule that binds to the introduced T cell receptor or the chimeric antigen receptor. The invention also relates to an apparatus for the expansion of the selected cell population.

BACKGROUND OF THE INVENTION

The development of techniques for propagating T cell populations in vitro has been crucial to many of the advances in the understanding of T cell recognition of antigen and T cell activation. The development of culture methods for the generation of human antigen-specific T cell clones has been useful in defining antigens expressed by pathogens and tumors that are recognized by T cells to establish methods of immunotherapy to treat a variety of human diseases. Antigen-specific T cells can be expanded in vitro for use in adoptive cellular immunotherapy or cancer therapy in which infusions of such T cells have been shown to have anti-tumor reactivity in a tumor-bearing host. In addition, adoptive immunotherapy has also been used to treat viral infections in immunocompromised individuals.

A method of expanding human T cells in vitro in the absence of exogenous growth factor and accessory cells that has been established in the recent years is described in U.S. Pat. No. 6,352,694 B1 and European Patent EP 0 700 430 B1. Disclosed in these patents is an in vitro method for inducing a population of T cells to proliferate. The method comprises contacting a population of T cells with a solid phase surface having directly immobilized thereon: (a) a first agent which provides a primary activation signal to the T cells, thereby activating the T cells; and (b) a second agent which stimulates an accessory molecule on the surface of the T cells, thereby stimulating the activated T cells. The binding of the first agent and the second agent to the T cells induces the T cells to proliferate/to expand. The preferred first agent described in U.S. Pat. No. 6,352,694 B1 and European Patent EP 0 700 430 B1 is a monoclonal anti-CD3 antibody which binds to the TCR/CD3 (TCR=T Cell Receptor) complex and thereby stimulates the TCR/CD3 complex-associated signal in the T cells. The preferred second agent according to these two patents is a monoclonal anti-CD28 antibody which binds the accessory molecule CD28 that is present on T cells. Binding of this second agent to the CD28 accessory molecule provides the necessary co-stimulus that is necessary for expansion/proliferation of activated T cells. Meanwhile, Dynabeads® CD3/CD28 (Invitrogen) are commercially available for T cell expansion. Dynabeads® CD3/CD28 CTS™ are uniform, 4.5 μm superparamagnetic, sterile, non-pyrogenic polystyrene beads coated with a mixture of affinity purified monoclonal antibodies against the CD3 and CD28 cell surface molecules on human T cells.

However, such magnetic beads are, for example, difficult to integrate into a method to expand cells under conditions required for clinical trials or therapeutic purposes since it has to be made sure that these magnetic beads are completely removed before administering the expanded T cells to a patient. Thus, the present invention aims to provide an alternative method for expanding cell populations such as regulatory T cells or central memory T-cells for research, diagnostic and especially therapeutic purposes. Ideally, this new method should also be compatible with integration into an automatized process which can be used for rapid and easy expansion of the desired cells population for therapeutic applications.

This object is solved by the subject matter of the independent claims, inter alia the methods, kits, arrangements and apparatuses as recited in the independent claims.

SUMMARY OF THE INVENTION

The present invention provides methods, kits, arrangements, and apparatus for the in vitro expansion of a desired cell population, having a receptor molecule on its surface which can provide upon binding of a suitable agent a primary activation signal to the population of cells and thereby activating the population of cells for expansion (proliferation). Thus, the methods of the invention are also used for inducing a population of cells to proliferate.

According to a first aspect, the invention provides an in vitro-method of expanding a population of cells, comprising contacting a sample comprising the population of cells with a multimerization reagent, wherein the multimerization reagent has reversibly immobilized thereon (bound thereto) a first agent that provides a primary activation signal to the cells;

wherein the multimerisation reagent comprises at least one binding site Z1 for the reversible binding of the first agent, wherein the first agent comprises at least one binding partner C1, wherein the binding partner C1 is able of reversibly binding to the binding site Z1 of the multimerization reagent, wherein the first agent is bound to the multimerization reagent via the reversible bond formed between the binding partner C1 and the binding site Z1, and wherein the first agent binds to a receptor molecule on the surface of the cells, thereby providing a primary activation signal to the cells and thereby activating the cells.

According to a second aspect the invention provides an in vitro-method of expanding a population of cells, comprising contacting a sample comprising the population of cells with a multimerization reagent, wherein the multimerization reagent is in a soluble form and has immobilized thereon (bound thereto) a first agent that provides a primary activation signal to the cells;

wherein the multimerisation reagent comprises at least one binding site Z1 for the binding of the first agent, wherein the first agent comprises at least one binding partner C1, wherein the binding partner C1 is able of binding to the binding site Z1 of the multimerization reagent, wherein the first agent is bound to the multimerization reagent via the bond formed between the binding partner C1 and the binding site Z1, and wherein the first agent binds to a receptor molecule on the surface of the cells, thereby providing a primary activation signal to the cells and thereby activating the cells.

According to a third aspect the invention provides a reagent kit for expanding a population of cells, the kit comprising (i) a multimerization reagent,
wherein the multimerisation reagent comprises at least one binding site Z for the reversible binding of a first agent,
  (ii) a first agent that binds to a receptor molecule on the surface of the cells, thereby providing a primary activation signal to the cells and thereby activating the cells,
wherein the first agent comprises at least one binding partner C1, wherein the binding partner C1 is able of reversibly binding to a binding site Z1 of the multimerization reagent, wherein the first agent is bound to the multimerization reagent via the reversible bond formed between the binding partner C1 and the binding site Z1, and
  (iii) a second agent that stimulates an accessory molecule on the surface of the cells,
wherein the second agent comprises a binding partner C2, wherein the binding partner C2 is able of reversibly binding to a binding site Z2 of the multimerization reagent, wherein the second agent is bound to the multimerization reagent via the bond formed between the binding partner C2 and the binding site Z2,
wherein the second agent binds to the accessory molecule on the surface on the surface of the cells, thereby stimulating the activated cells.

According to a fourth aspect the invention provides a reagent kit for expanding a population of cells, the kit comprising (i) a multimerization reagent,
wherein the multimerisation reagent is in soluble form and comprises at least one binding site Z for the reversible binding of a first agent,
  (ii) a first agent that binds to a receptor molecule on the surface of the cells, thereby providing a primary activation signal to the cells and thereby activating the cells,
wherein the first agent comprises at least one binding partner C1, wherein the binding partner C1 is able of binding to a binding site Z1 of the multimerization reagent, wherein the first agent is bound to the multimerization reagent via the reversible bond formed between the binding partner C1 and the binding site Z1.

According to a fifth aspect the invention provides an in vitro-method of serially expanding a population of lymphocytes, wherein the population of lymphocytes comprises T cells, the method comprising contacting a sample comprising the T cell comprising population of lymphocytes with a multimerization reagent, wherein the multimerization reagent is in a soluble form and has reversibly immobilized thereon (i) a first agent that provides a primary activation signal to the T cells and (ii) a second agent which stimulates an accessory molecule on the surface of the T cells, wherein the multimerisation reagent comprises at least one binding site Z1 for the reversible binding of the first agent, wherein the first agent comprises at least one binding partner C1, wherein the binding partner C1 is able of reversibly binding to the binding site Z1 of the multimerization reagent, wherein the first agent is bound to the multimerization reagent via the reversible bond formed between the binding partner C1 and the binding site Z1, wherein the multimerisation reagent comprises at least one binding site Z2 for the reversible binding of the second agent, wherein the second agent comprises at least one binding partner C2, wherein the binding partner C2 is able of reversibly binding to the binding site Z2 of the multimerization reagent, wherein the first agent is bound to the multimerization reagent via the reversible bond formed between the binding partner C2 and the binding site Z2, wherein the first agent binds to a receptor molecule on the surface of the T cells, thereby providing a primary activation signal to the cells and thereby activating the T cells, wherein the second agent binds to the accessory molecule on the surface of the T cells, thereby stimulating the activated cells, the first agent and the second agent thereby together inducing the T cells to expand.

According to a sixth aspect the invention provides an arrangement of a bioreactor and a stationary phase for chromatography, wherein the bioreactor is suitable for the expansion of cells, wherein the stationary phase is suitable for cell separation and removal of reagents, the stationary phase being a gel filtration matrix and/or affinity chromatography matrix, wherein the gel filtration and/or affinity chromatography matrix comprises an affinity reagent, wherein the affinity reagent comprises a binding site Z1 specifically binding to a binding partner C1 comprised in a first agent and/or the affinity reagent comprises a binding site Z2 specifically binding to a binding partner C2 comprised in a second agent, thereby being suitable of immobilizing on the stationary phase the first agent and/or the second agent, the first binding partner C1 and/or the free second binding partner C2, wherein the bioreactor and the stationary phase are fluidly connected.

According to a seventh aspect the invention provides an apparatus for purification and expansion of a population of cells, the apparatus comprising at least one arrangement of a bioreactor and a stationary phase for chromatography according to the sixth aspect.

According to an eight aspect, the invention provides a multimerization reagent capable of expanding a population of cells, wherein the multimerisation reagent is in soluble form and comprises at least one binding site Z1 for the reversible binding of a first agent that provides a primary activation signal to the cells, wherein the multimerization reagent has reversibly immobilized thereon (bound thereto) said first agent that provides a primary activation signal to the cells;

wherein the first agent comprises at least one binding partner C1, wherein the binding partner C1 is able of reversibly binding to the at least one binding site Z1 of the multimerization reagent, wherein the first agent is bound to the multimerization reagent via the reversible bond formed between the binding partner C1 and the binding site Z1, According to a ninth aspect, the invention provides a composition capable of expanding a population of cells, the composition comprising (i) a first multimerization reagent, wherein the first multimerisation reagent is in soluble form and comprises at least one binding site Z1 for the reversible binding of a first agent that provides a primary activation signal to the cells, wherein the first multimerization reagent has reversibly immobilized thereon (bound thereto) said first agent that provides a primary activation signal to the cells;

wherein the first agent comprises at least one binding partner C1, wherein the binding partner C1 is able of reversibly binding to the at least one binding site Z1 of the multimerization reagent, wherein the first agent is bound to the multimerization reagent via the reversible bond formed between the binding partner C1 and the binding site Z1, and (ii) a second multimerization reagent, wherein the second multimerization reagent is in soluble form and comprises at least one binding site Z2 for the reversible binding of a second agent that stimulates an accessory molecule on the surface of the cells, wherein the multimerization reagent has reversibly immobilized thereon (bound thereto) said second agent that stimulates an accessory molecule on the surface of the cells, wherein the second agent comprises a binding partner C2, wherein the binding partner C2 is able of binding to the at least one binding site Z2 of the multimerization reagent, wherein the second agent is bound to the multimerization reagent via the bond formed between the binding partner C2 and the binding site Z2.

DESCRIPTION OF THE DRAWINGS

The invention will be better understood with reference to the detailed description when considered in conjunction with the non-limiting examples and the accompanying drawings. The figures illustrate embodiments of methods of the invention. Without wishing to be bound by theory, the figures include conclusions with regard to the underlying expansion mechanism. The conclusions are given for illustrative purposes only and merely serve in allowing a visualization of the expansion method is achievable on a molecular level.

1, the multimerization reagent (4) might further include multimeric calmodulin or glutathione-S-transferase, both of which form reversible bonds with calmodulin binding peptides or glutathione. Thus, the binding site Z2 (44) can be formed by calmodulin or glutathione-S-transferase. Such a protein conjugate of for example, calmodulin with a streptavidin mutein can be made by standard protein chemistry, for example, by using bifunctional linkers.

Figure 1A:
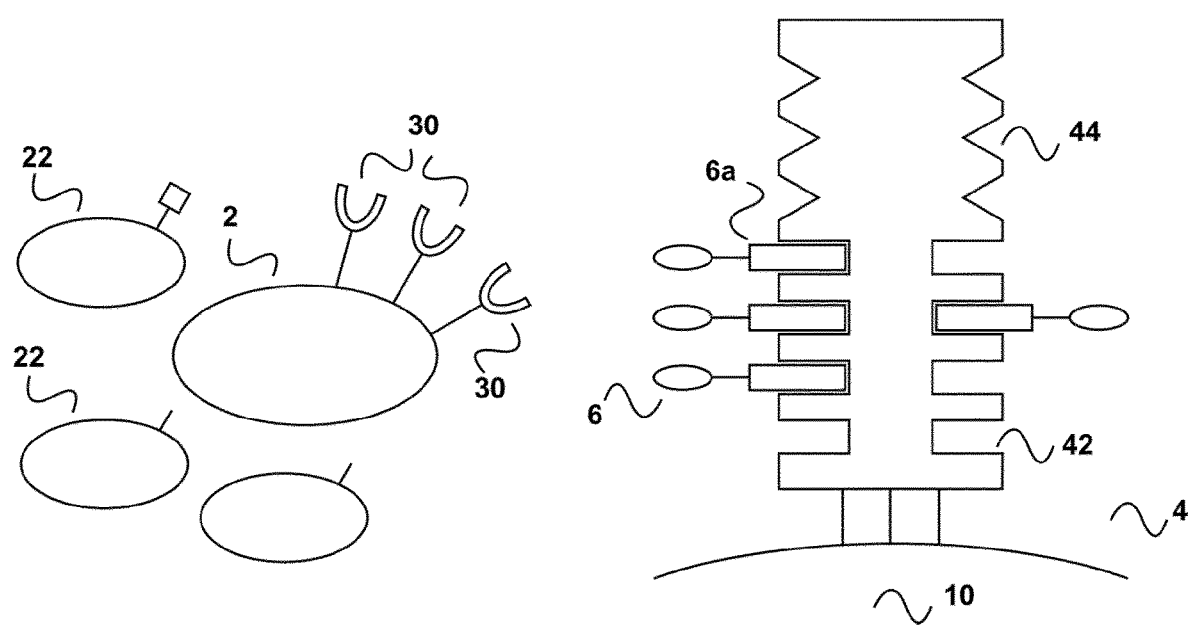
As shown in FIG. 1a a sample that comprises the population of cells (2) that carry a surface receptor molecule (30) is contacted with a multimerization reagent (4). The population of cells (2) is in mixture with other cell populations (22) that lack the surface receptor molecule (30). The multimerization reagent (4) has reversibly immobilized thereon (bound thereto) a first agent (6) that provides a primary activation signal to the cells. The multimerization reagent (4) comprises at least one binding site Z1 (42) for the reversible binding of the first agent (6) and the first agent (6) comprises at least one binding partner C1 (6a), wherein the binding partner C1 (6a) is able of reversibly binding to the binding site Z1 (44) of the multimerization reagent. Thus, for immobilization, the first agent (6) is bound to the multimerization reagent (4) via the reversible bond formed between the binding partner C1 (6a) and the binding site Z1 (42). In the example shown in FIG. 1 the multimerization reagent (4) has a second binding site Z2 (44) which is not used in this example. The multimerization reagent (4) is itself immobilized on a solid support (10) such as a magnetic bead, a polymeric bead of a surface of a cell culture plate or reactor. The population of cells (2) can, for example be, a lymphocyte cell population such as a population of B cells that can be activated via the CD40 receptor (see, for example, Carpenter et al, *Journal of Translational Medicine* 2009, 7:93 "Activation of human B cells by the agonist CD40 antibody CP-870,893 and augmentation with simultaneous toll-like receptor 9 stimulation). In this case, the cell surface molecule (30) is CD40 and the first reagent (6) can be any CD40 binding molecule that provides the desired activation signal, for example, the monoclonal antibody CP-870,893 or an antibody binding fragment thereof such an a monovalent Fab fragment. The binding partner C1 of the first agent (6) may, for example, be any affinity peptide that is fused or conjugated to, for example, the C-terminus of one of the two polypeptide chains (heavy or light chain) of the antibody molecule. The binding partner C1 (6a) may, for example, be a streptavidin-binding peptide such as the peptide Trp-Ser-His-Pro-Gln-Phe-Glu-Lys (SEQ ID NO: 01), also known as the "Strep-tag®") that is described in U.S. Pat. No. 5,506,121, for example, or streptavidin binding peptides having a sequential arrangement of two or more individual binding modules as described in International Patent Publication WO 02/077018 or U.S. Pat. No. 7,981, 632. When using a streptavidin binding peptide as binding partner C1, the multimerization reagent (4) be any streptavidin mutein to which the streptavidin peptide (=first binding partner C1 (6a)) reversibly binds via its (biotin) binding sites Z1 (42) schematically shown in FIG. 1. Such a multimerization reagent may be a streptavidin mutein (analog) that comprises the amino acid sequence Val$^{44}$-Thr$^{45}$-Ala$^{46}$-Arg$^{47}$ (SEQ ID NO: 02) at sequence positions 44 to 47 of wild type streptavidin or a streptavidin mutein (analog) that comprises the amino acid sequence Ile$^{44}$-Gly$^{45}$-Ala$^{46}$-Arg$^{47}$ (SEQ ID NO: 03) at sequence positions 44 to 47 of wild type streptavidin, both of which are described in U.S. Pat. No. 6,103,493, for example, and are commercially available under the trademark Strep-Tactin®. In the Example of FIG.
Figure 1B:
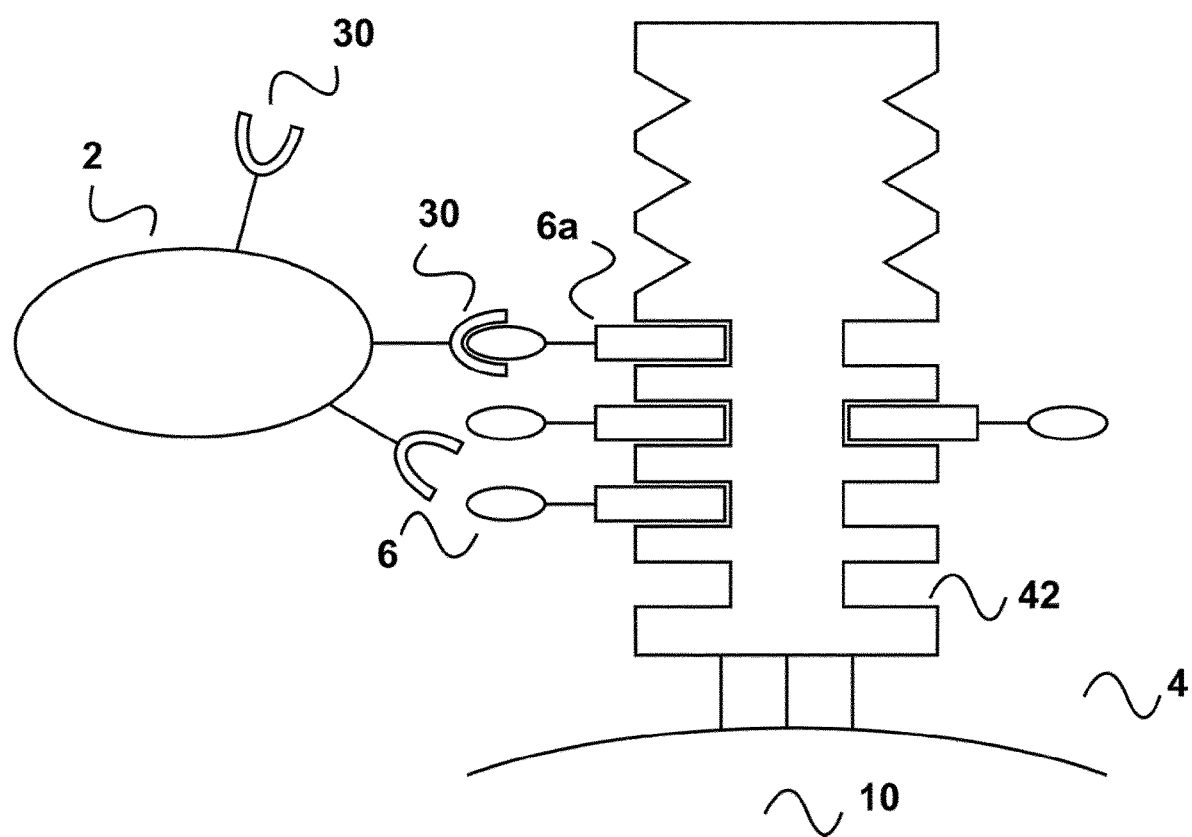
FIG. 1 depicts an embodiment of an in vitro-method of expanding of expanding a population of cells that has a cell surface receptor the binding of which by a first agent can provide an activation signal for the cells to expand.

As shown in FIG. 1b, after contacting the cell population (2) with the multimerisation reagent (4) and usually incubating the cell population with the multimerization reagent (4), the population of cells (2) forms complexes/is bound to the multimerization agent via the first agent (6). The first agent binds specifically to the cell surface receptor molecule such as CD40 in this Example and provides the activation signal for cell expansion, of for example B cells. The other cell populations (22) contained in the initial sample that lack the specific cell surface molecule (30) do not bind to the multimerization reagent. In this respect, it is noted that the cell population (2) usually has multiple copies of the cell surface molecule (30) on its surface and binding of these multiple copies is typically needed for activation. Thus, the multimerization agent (4) provide typically more than one binding site Z1 so that multiple first agents (6) can be reversibly bound to achieve "multimerization" of the first agent, meaning to present the first agent in a sufficient density to the population of cells (2) (not shown in the scheme of FIG. 1). In this respect, it is noted that a multimerization agent as used herein can as such have multiple binding sites Z1, for example, a streptavidin mutein (being a homo-tetramer) in its native state has four such binding sites Z1. It is however also possible that the multimerization reagent is based on a compound that has as such only one binding site Z1 for the reversible binding of a binding partner C1. Such an example is multimeric calmodulin. Calmodulin as such has only one binding site for calmodulin binding peptides. However, calmodulin can be biotinylated and then reacted with streptavidin-oligomers (see also below), thereby providing a multimerization reagent in which multiple calmodulin molecules are presented in high density on a "scaffold", thereby providing multimeric calmodulin.

Figure 1C:
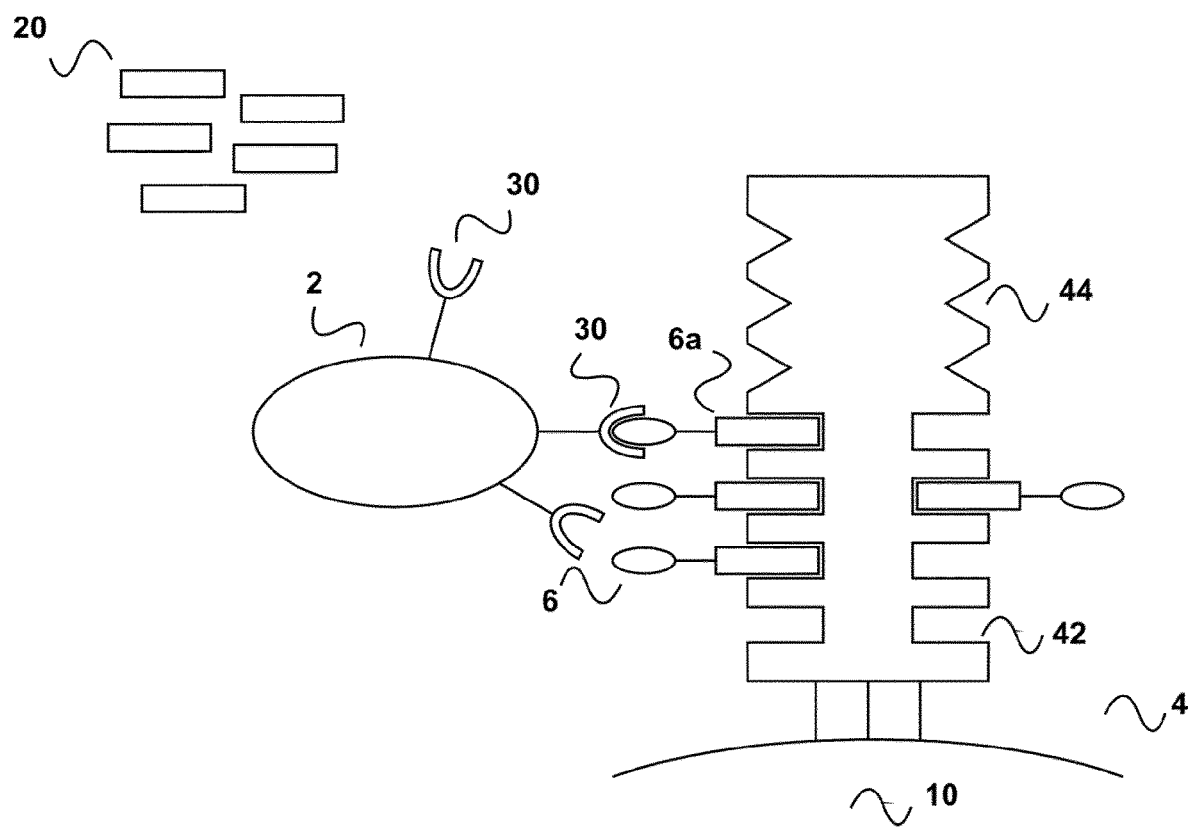

As shown in FIG. 1c, after incubation (which is usually carried out over a period of time suitable to achieve expansion of the desired cell population) the binding between the binding partner C1 (6a) of the first agent (6) and the binding site Z1 of the multimerization reagent (4) is disrupted by disrupting the respective reversible bond. The disruption may be achieved by adding a competitor to the incubation/reaction mixture containing the population of cells (2) being bound to the multimerization reagent. For competitive disruption (which can be understood as being a competitive elution) of the reversible bond between the binding partner C1 (6a) of the first agent and the binding site Z1 (22) of the multimerization reagent, the incubation mixture/population of cells can be contacted with a free first binding partner C1 (20) or an analog of said first binding partner C that is capable of disrupting the bond between the first binding partner C1 (6a) and the binding site Z1 (22). In the example of the binding partner C1 being a streptavidin binding peptide that binds to biotin binding site of streptavidin, the first free partner C1 (20) may be the corresponding free streptavidin binding peptide or an analogue that binds competitively. Such an analogue can, for example, be biotin or a biotin derivate such as desthiobiotin.

Figure 1D:
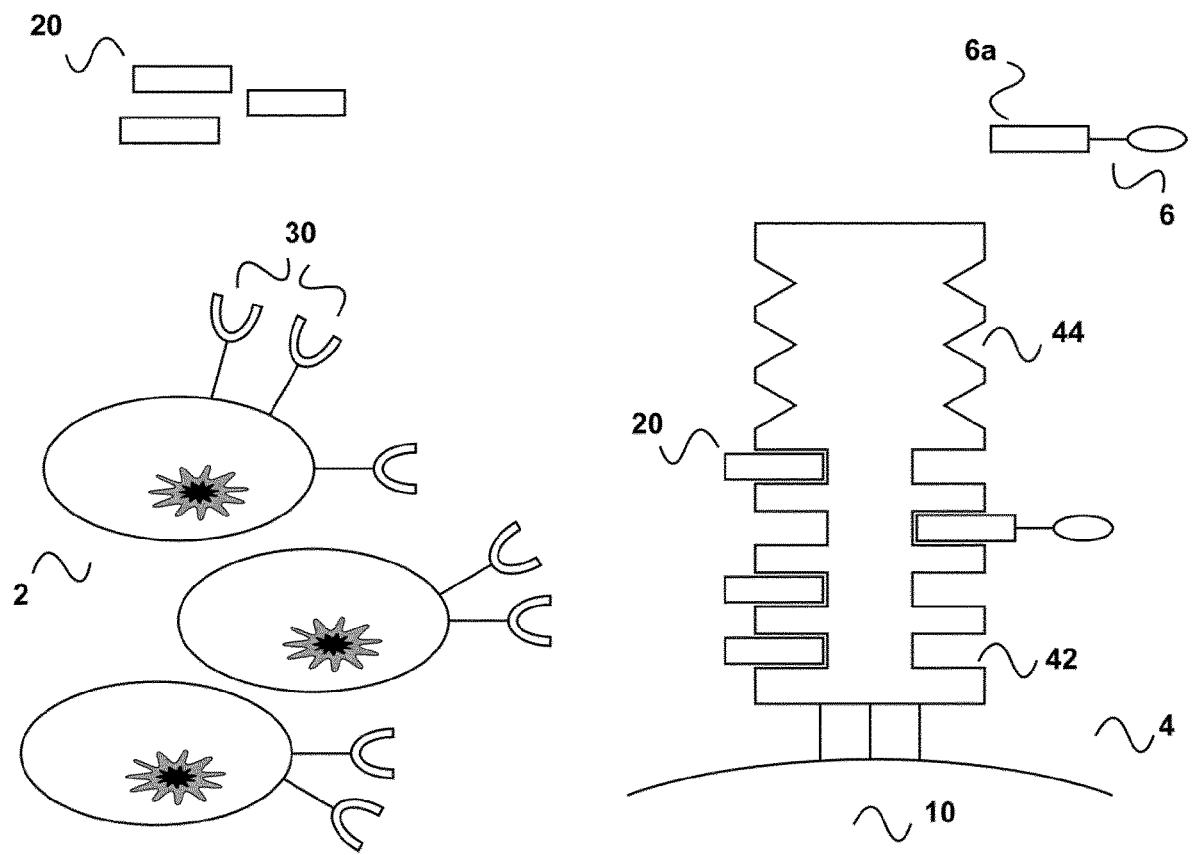

As shown in FIG. 1d, addition of the first free partner (20) or the analogue thereof results in displacement of the binding partner C1 (6a) from the multimerization reagent (4) and thus, since the binding partner C1 is comprised in the first agent (6), displacement of the first agent (6) from the multimerization reagent (4). This displacement of the first agent (6) in turn results in a dissociation of the first agent (6) from the cell surface receptor (30), in particular if the binding affinity of the bond between the first agent and the cell surface receptor (30) has a dissociation constant ($K_d$) in the range of $10^{-2}$ M to $10^{-13}$ M and is thus also reversible. Due to this dissociation, the stimulation of the cell population (2) is also terminated. Thus, the present invention provides the advantage that the time period of the stimulation or expansion of the cell population can be exactly controlled and thus also the functional status of the cell population can be closely controlled. In this context, it is noted that the binding affinity of antibody molecules towards their antigen, including for example, a cell surface receptor molecule such as CD40 in this Example, is usually in the affinity range of the $K_d$ of $10^{-7}$ M to $10^{-13}$ M. Thus, conventional monoclonal antibodies can be used as first agent (and also of course second agent as explained below) in the present invention. In order to avoid any unwanted avidity effects that lead to a stronger binding, monoclonal antibodies can also be used in form of their monovalent antibody fragments such as Fab-fragments or single chain Fv fragments.

In addition, due to the dissociation of the first agent from the cell surface molecule (30), the present invention has the added advantage that the stimulated cell population is free of stimulating agents at the end of the stimulation period and that all other reagents used in the method, namely the first agent (6) as well as the free first partner (20) of the binding partner C1 or the analogue thereof can be easily removed from the stimulated cell population (2) via a "removal cartridge" described in International patent application WO 2013/124474 while the multimerization reagent (4) being immobilized on a solid support such as a bioreactor surface or a magnetic bead is being held back. Thus, reverting to the removal of the free agent (6) and the free first partner (20), in accordance with the description of the "removal cartridge" in WO 2013/124474 (see with reference to FIG. 4 thereof, for example), the elution sample obtained in FIG. 1d here can be loaded onto the second chromatography column of WO 2013/124474. This chromatography column has a suitable stationary phase that is both an affinity chromatography matrix and, at the same time, can act as gel permeation matrix. This affinity chromatography matrix has an affinity reagent immobilized thereon. The affinity reagent may, in the case of the current Example, for instance, be streptavidin, a streptavidin mutein, avidin, an avidin mutein or a mixture thereof. The first agent (6), the free first partner (20) of the binding partner C1 (which is also called "competition reagent" herein) bind to the affinity reagent, thereby being immobilized on the chromatography matrix. As a result the elution sample containing the isolated and expanded cell population (2) is being depleted of the first agent (6) and the competition reagent (20). The expanded cell population (2), being freed of any reactants, is now in a condition for further use, for example, for diagnostic applications (for example, further FACS™ sorting) or for any cell based therapeutic application.

FIG. 2 shows a further embodiment of an expansion method of the invention. As shown in FIG. 2a a sample comprises a population of cells (2) that carry two specific cell surface molecules (30) and (32). The cell surface molecule (30) is involved in a primary activation signal to the cell population, while the cell surface molecule (32) is an accessory molecule on the cell surface that is involved in providing a stimulus to the cells. The population of cells may, for example, be a T cell population in which the cell surface molecule (30) is a TCR/CD3 complex and the cell surface molecule (32) is the accessory molecule CD28. Binding of both the TCR/CD3 complex as the primary activation signal and CD28 as co-stimulant are necessary for expansion/proliferation of T cells. The population of T cells (2) is in mixture with other cell populations (22) that lack the surface receptor molecules (30) and (32). Also in this embodiment, the cell population (2) is contacted with a multimerization reagent (4). The multimerization reagent (4) has reversibly immobilized thereon (bound thereto) a first agent (6) that provides a primary activation signal to the cells. In addition, the multimerization agent has reversibly immobilized thereon (bound thereto) a second agent (8) that stimulates CD28 as accessory molecule on the surface of the cells.

The multimerization reagent (4) comprises at least one binding site Z1 (42) for the reversible binding of the first agent (6) and the first agent (6) comprises at least one binding partner C1 (6a), wherein the binding partner C1 (6a) is able of reversibly binding to the binding site Z1 (44) of the multimerization reagent. Thus, for immobilization, the first agent (6) is bound to the multimerization reagent (4) via the reversible bond formed between the binding partner C1 (6a) and the binding site Z1 (42). In addition, in the Example illustrated in FIG. 2, the second agent (8) comprises a binding partner C2 (8a), wherein the binding partner C2 is able of being reversibly bound to a binding site Z2 (44) of the multimerization reagent (4). The second agent (8) is bound to the multimerization reagent (4) via the reversible bond formed between the binding partner C2 (8a) and the binding site Z2 (44). In this Example, the first agent (6) might be a monoclonal anti-CD3-antibody or an antigen binding fragment thereof such as a Fab fragment. The second agent (8) might be a monoclonal anti-CD28 antibody or an antigen binding fragment thereof such as Fab fragment. The first binding partner (6a) might be a streptavidin binding peptide (6a) that is fused or conjugated to the anti-CD3 antibody or the anti-CD3 antibody fragment. The second binding partner (8a) might be calmodulin binding peptide that is also conjugated or fused to the CD28 antibody or the CD28 binding antibody fragment. In this context, it is noted that monoclonal antibodies against, for example, CD3 or CD28 are well-known (see, for example, U.S. Pat. No. 6,352,694 B or European Patent EP 0 700 430 B1 discussed above) and are commercially available from numerous suppliers such as Santa Cruz Biotechnology (Santa Cruz, Calif. USA), Life Technologies, (Carlsbad, Calif., USA), BD Biosciences (San Jose, Calif., USA), Biolegend (San Diego, Calif., USA) or Miltenyi Biotec (Bergisch Gladbach, Germany) to name only a few. Accordingly, such monoclonal antibodies can be used as first and second agent and can, for example, be chemically coupled (conjugated) with a binding partner C1 or C2. Alternatively, it is also possible to either clone the genes of the variable domains from the hydridoma cell line or use an antibody of which the amino acid sequence is known and produce a respective antibody fragment such as a Fab fragment or a Fv recombinantly. When using such an approach as described herein in the Example section for both the hybridoma cell line OKT3 (ATCC® CRL-8001™, described in U.S. Pat. No. 4,361,549) that produces a monoclonal anti-CD3 antibody) and the anti-CD28 antibody 28.3 described by Vanhove et al, BLOOD, 15 Jul. 2003, Vol. 102, No. 2, pages 564-570 and GenBank accession number AF451974.1, the binding partners C1 and C2 are conveniently provided by the respective expression vector used for the recombinant production so that the antibody fragment carries the binding partner C1 or C2 as a fusion peptide as the C-terminus of either the light or the heavy chain (In this context, the amino acid sequence of the variable domain of the heavy chain and of the variable domain of the light chain of the antibody OKT3 that are described in Arakawa et al J. Biochem. 120, 657-662 (1996) are shown for illustration purposes as SEQ ID NOS 17 and 18 and in the accompanying Sequence Listings, while the amino acid sequence of the variable domain of the anti-CD28 antibody 28.3 described by Vanhove et al, supra, is shown as SEQ ID NOS 19 (VH) and 20 (VL) in the accompanying Sequence Listings). Also this methodology of cloning the variable domains of an antibody molecule and recombinantly producing a respective antibody fragment is well known to the person skilled in the art, see for example, Skerra, A. (1994) A general vector, pASK84, for cloning, bacterial production, and single-step purification of antibody Fab fragments. Gene 141, 79-84, or Skerra, A. (1993) Bacterial expression of immunoglobulin fragments. Curr Opin Immunol. 5, 256-562). Finally, it is also possible to generate antibody molecules of artificial binding molecules with antibody like properties against a given target such as CD3 or CD28 as in the Example of FIG. 2 by well-known evolutive methods such as phage display (reviewed, e.g., in Kay, B. K. et al. (1996) Phage Display of Peptides and Proteins-A Laboratory Manual, 1$^{st}$ Ed., Academic Press, New York N.Y.; Lowman, H. B. (1997) Annu. Rev. Biophys. Biomol. Struct. 26, 401-424, or Rodi, D. J., and Makowski, L. (1999) Curr. Opin. Biotechnol. 10, 87-93), ribosome display (reviewed in Amstutz, P. et al. (2001) Curr. Opin. Biotechnol. 12, 400-405) or mRNA display as reported in Wilson, D. S. et al. (2001) Proc. Natl. Acad. Sci. USA 98, 3750-3755.

In the case of the Example shown in FIG. 2, the multimerization reagent (4) has two different binding sites Z1 (42) and Z2 (44). With the binding partner C1 (6a) being a streptavidin binding peptide, the binding site Z1 (42) of the multimerization reagent (4) is provided by a suitable streptavidin mutein to which the streptavidin peptide (6a) reversibly binds. Since the binding C2 is a calmodulin binding peptide, the binding site Z2 (44) of the multimerization reagent (4) is provided by multimeric calmodulin. The multimerization reagent (4) can be a single molecule, for example a conjugate of multimeric calmodulin with streptavidin (this alternative would be usually used in case of a soluble multimerization) or can also consist of two independent molecules. The latter option is preferred when the multimerization reagent (44) is immobilized on a solid support as shown in FIG. 2 In this case, a mixture of a streptavidin mutein and calmodulin can be coated (immobilized) on the solid support, for example, in a 1:1 molar ratio with respect to the binding sites Z1 and Z2. In this context, it is noted that, due to the immobilisation of calmodulin on the surface of the solid support, there is no need to prepare multimeric calmodulin as explained above but immobilization of the calmodulin on the surface is sufficient to present calmodulin (that, as mentioned above, has only a single binding site for calmodulin binding peptides, in a sufficiently high density to ensure binding of the cell population (2). For example, in this case, a bivalent antibody fragment that has two binding sites against CD28 or an intact antibody that has per se two identical binding sites could be used as second reagent (8).

Figure 2A:
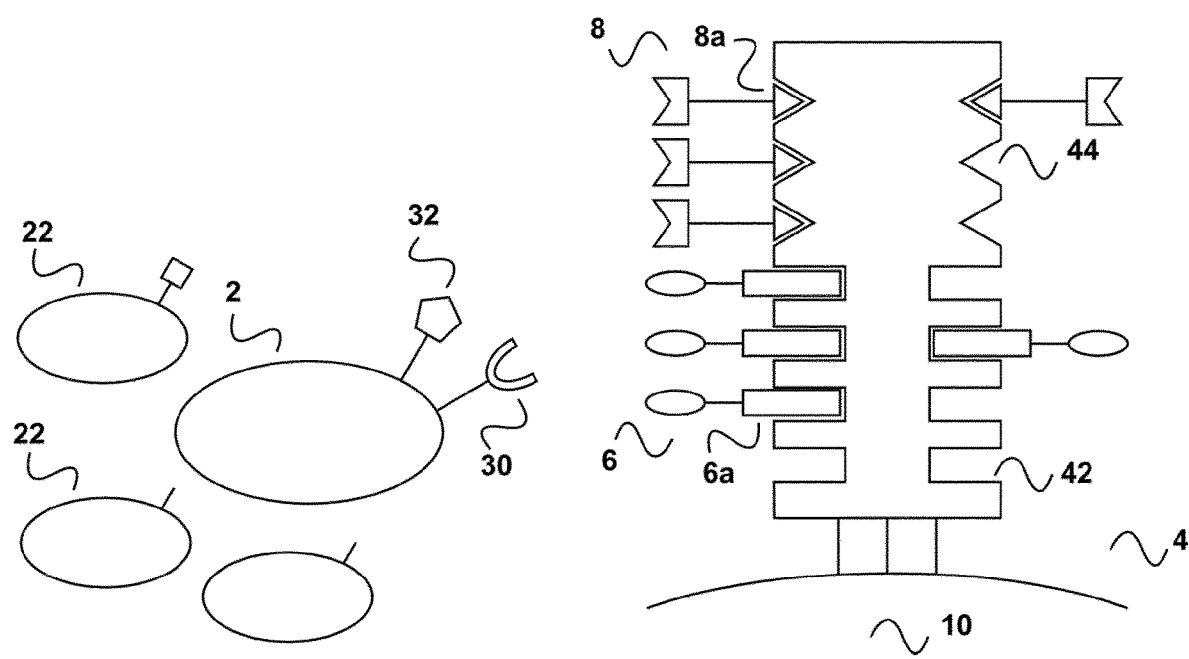
Figure 2B:
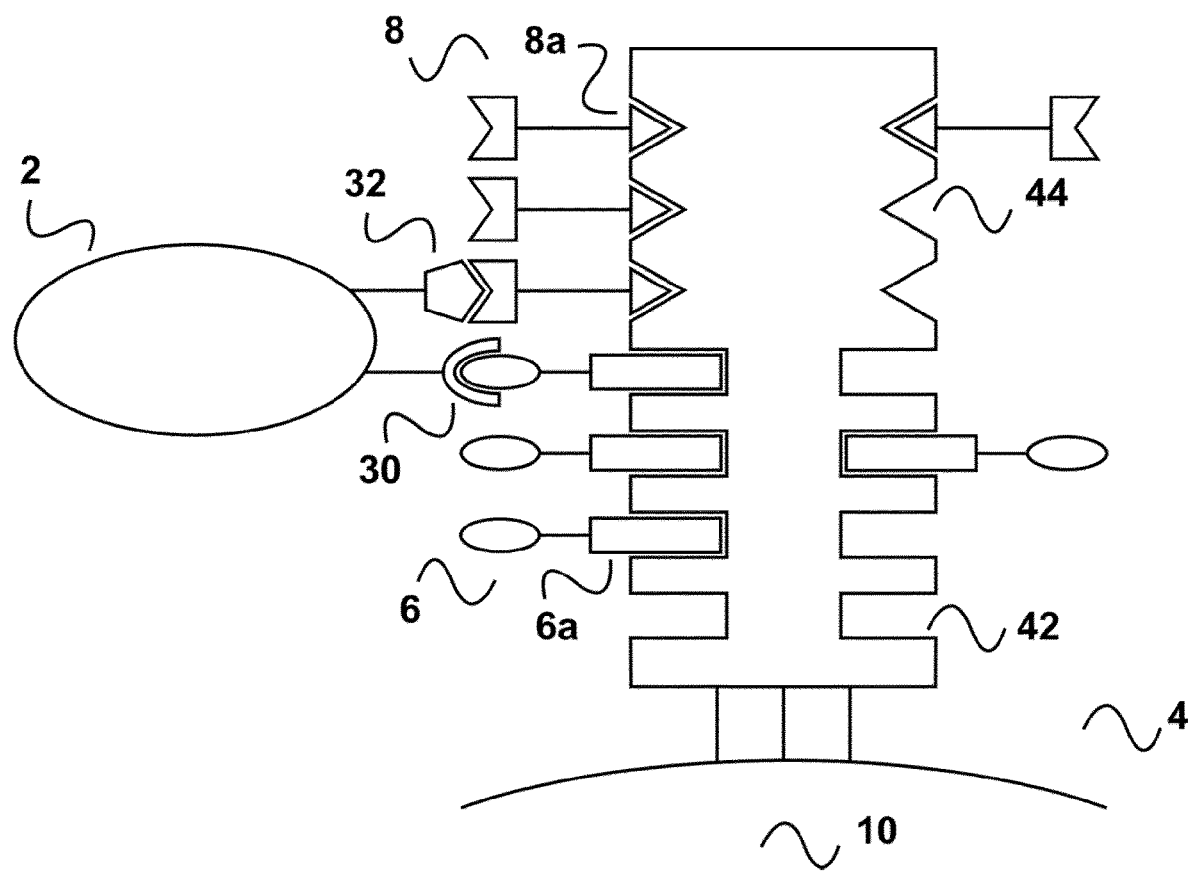

As shown in FIG. 2b, after contacting the T cell population (2) with the multimerisation reagent (4) and usually incubating the cell population with the multimerization reagent (4), the population of T cells (2) forms complexes/is bound to the multimerization agent via the first agent (6) and the second agent (8). The first agent (6) and the second agent (8) bind specifically to the TCR/CD3 complex and the accessory molecule CD28, thereby inducing the T cells to proliferate/expand.

Figure 2C:
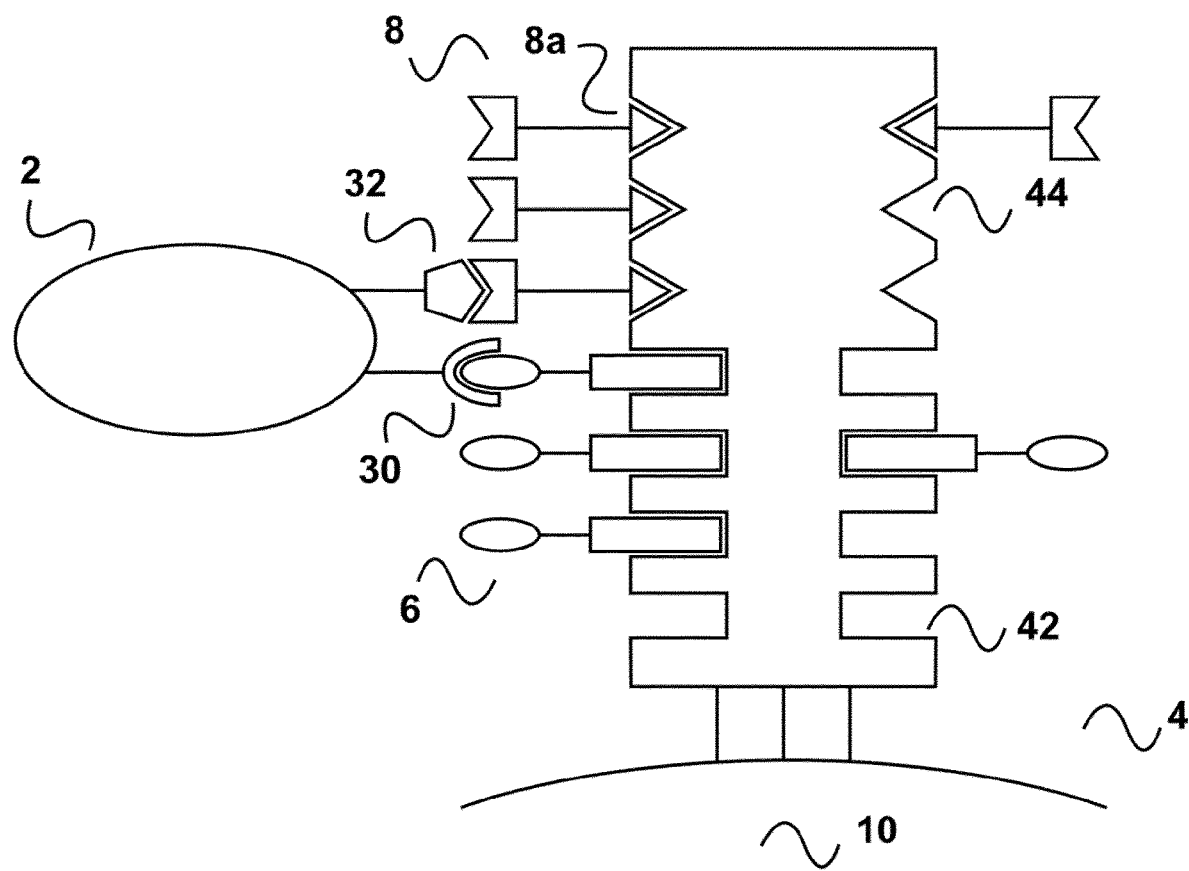

As shown in FIG. 2c, after incubation (which is usually carried out over a period of time suitable to achieve expansion of the desired cell population) the binding between the binding partner C1 (6a) of the first agent (6) and the binding site Z1 of the multimerization reagent (4) is disrupted by disrupting the respective reversible bond. Likewise, the binding between the binding partner C2 (8a) of the second agent (8) and the binding site Z2 of the multimerization reagent (4) is disrupted by disrupting the respective reversible bond. The reversible bond between the binding partner C1 (6a) of the first agent (6) and the binding site Z1 can be disrupted by biotin (which acts as an analogue (20) of the free first partner) while the reversible bond between the binding partner C2 (8a) of the first agent (8) and the binding site Z2 can be disrupted by the addition of a metal chelator (calcium chelator) such as EDTA or EGTA (that acts an analogue (20) of the free second partner) since the binding of calmodulin to calmodulin binding peptides is calcium ion ($Ca^{2+}$) dependent). This of course means that the contacting of the cell population (2) is carried out in a $Ca^{2+}$ containing buffer.

Figure 2D:
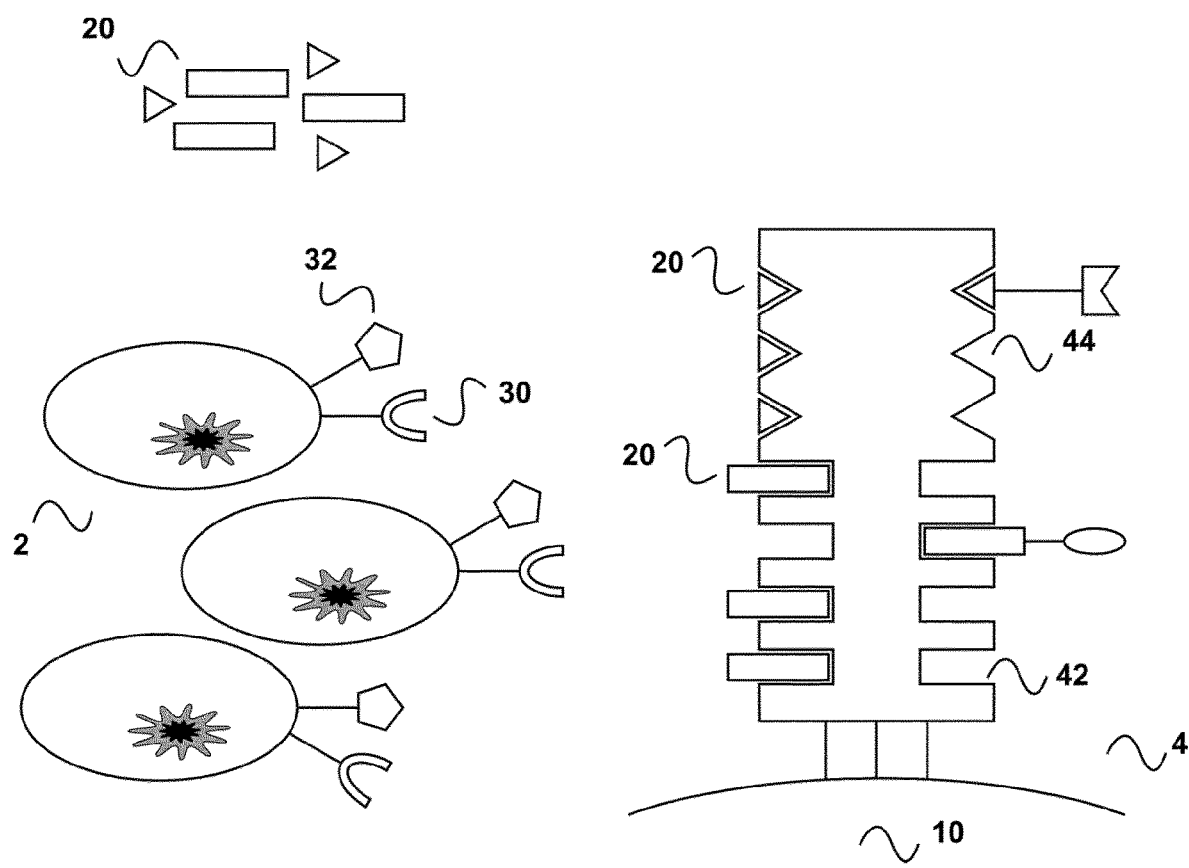

As shown in FIG. 2d, addition of the analogue (20) of the first free partner and the second free partner, respectively results in displacement of the binding partners C1 (6a) and C2 (8a) from the multimerization reagent (4) and thus in displacement of the first agent (6) and the second agent (8) from the multimerization reagent (4). This displacement of the first agent (6) and second agent (8) in turn results in a dissociation of the first agent (6) and the second agent (8) from the TCR/CD3 complex and the accessory molecule CD28, thereby terminating the stimulation/expansion of the cell population (2). Thus, as said above, the present invention provides the advantage that the time period of the stimulation or expansion of a T cell population can be exactly controlled and therefore also the functional status of the population of T cells can be closely controlled. After the elution of the cells as illustrated in FIG. 1d, the first agent (6), the second reagent (8) as well as the analogue (20) of free first partner of the binding partner C1 and the second free partner of the binding partner C2 can be easily removed from the stimulated cell population (2) via a "removal cartridge" described in International patent application WO 2013/124474. In addition, and importantly, in case the initial sample was a population of lymphocytes, for example, in form of PMBCs obtained from a Ficoll gradient, the T cell population (2) is now available for serial expansion as defined here. Since the expanded cell population (e.g. by an initial stimulation via CD3/CD28) can be transfected during expansion e.g. with a T cell receptor (TCR) or a chimeric antigen receptor (CAR, also known as artificial T cell receptor), the genetically modified cells can then be liberated from the initial stimulus and subsequently be stimulated with a second type of stimulus e.g. via the de novo introduced receptor. These second stimuli may comprise an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). Thus, the T cell population obtained from this serial expansion can be used for adoptive cell transfer.

Figure 3A:
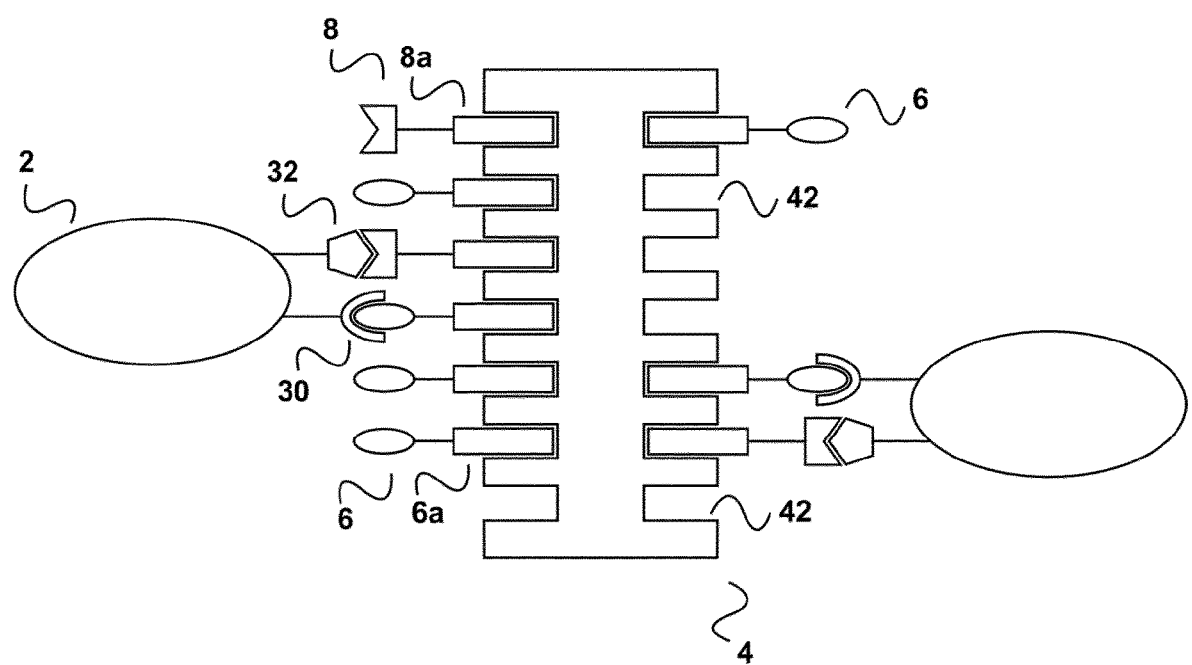

FIG. 3 shows a further embodiment of an expansion method of the invention. Also the sample used in this Example comprises a population of T cells (2) that carry two specific cell surface molecules (30) and (32), with the cell surface molecule (30) being a TCR/CD3 complex and the cell surface molecule (32) being the accessory molecule CD28. In FIG. 3a the population of T cells (2) is shown after being contacted with a multimerization reagent (4). Also in this Example, the multimerization reagent (4) has reversibly immobilized thereon (bound thereto) as first agent (6) an anti-CD3 antibody or an antigen binding fragment thereof that provides a primary activation signal to the T cells and as second agent (8) an anti-CD28 antibody or an antigen binding fragment thereof that stimulates CD28 as accessory molecule.

The multimerization reagent (4) shown in the Example of FIG. 3 comprises only one type binding site Z1 (42) for the reversible binding of both the first agent (6) and the second agent (8). Both the first agent (6) and the second agent (8) comprise at least one binding partner C1 (6a, 8a), wherein both the binding partner C1 (6a) and the binding partner (8a) are able of reversibly binding to the binding site Z1 (44) of the multimerization reagent. Thus, for immobilization, the first agent (6) and the second agent (8), respectively are bound to the multimerization reagent (4) via the reversible bond formed between the binding partner C1 (6a) and the binding partner C2 and the binding site Z1 (42). The binding partners C1 and C2 can either be different or identical. For example, the binding partner C1 can be a streptavidin binding peptide of the sequences Trp-Ser-His-Pro-Gln-Phe-Glu-Lys ((SEQ ID NO: 01), the "Strep-tag®") while the binding partner C2 can be the streptavidin binding peptide of the sequence Trp-Ser-His-Pro-Gln-Phe-Glu-Lys-(GlyGlyGlySer)$_3$-Trp-Ser-His-Pro-Gln-Phe-Glu-Lys ((SEQ ID NO: 04), also known as "di-tag3")) or of the sequence Trp-Ser-His-Pro-Gln-Phe-Glu-Lys-(GlyGlyGlySer)$_2$-Trp-Ser-His-Pro-Gln-Phe-Glu-Lys ((SEQ ID NO: 05), also known as "the di-tag2"), described by Junttila et al., Proteomics 5 (2005), 1199-1203 or U.S. Pat. No. 7,981,632). All these streptavidin binding peptides bind to the same binding site, namely the biotin binding site of streptavidin. If one or more of such streptavidin binding peptides is used as binding partners C1 and C2, the multimerization reagent (4) is a streptavidin mutein. As shown in FIG. 3, a soluble multimerization reagent (4) is used. In the case of a streptavidin mutein, this soluble multimerization reagent may, for example, be an oligomer or a polymer of streptavidin or avidin or of any mutein (analog) of streptavidin or avidin. The oligomer may comprise three or more monomers of streptavidin, avidin or a mutein therof. The oligomer or polymer may be crosslinked by a polysaccharide. Such oligomers or polymers of streptavidin or of avidin or of muteins of streptavidin or of avidin can in a first step be prepared by the introduction of carboxyl residues into a polysaccharide, e. g. dextran, essentially as described in "Noguchi, A., Takahashi, T., Yamaguchi, T., Kitamura, K., Takakura, Y., Hashida, M. & Sezaki, H. (1992). Preparation and properties of the immunoconjugate composed of anti-human colon cancer monoclonal antibody and mitomycin C dextran conjugate. Bioconjugate Chemistry 3, 132-137". In a second step, streptavidin or avidin or muteins thereof are coupled via primary amino groups of internal lysine residue and/or the free N-terminus to the carboxyl groups in the dextran backbone using conventional carbodiimide chemistry. Alternatively, cross-linked oligomers or polymers of streptavidin or avidin or of any muten of streptavidin or avidin may also be obtained by crosslinking via bifunctional linkers such as glutardialdehyde or by other methods described in the literature.

Figure 3B:
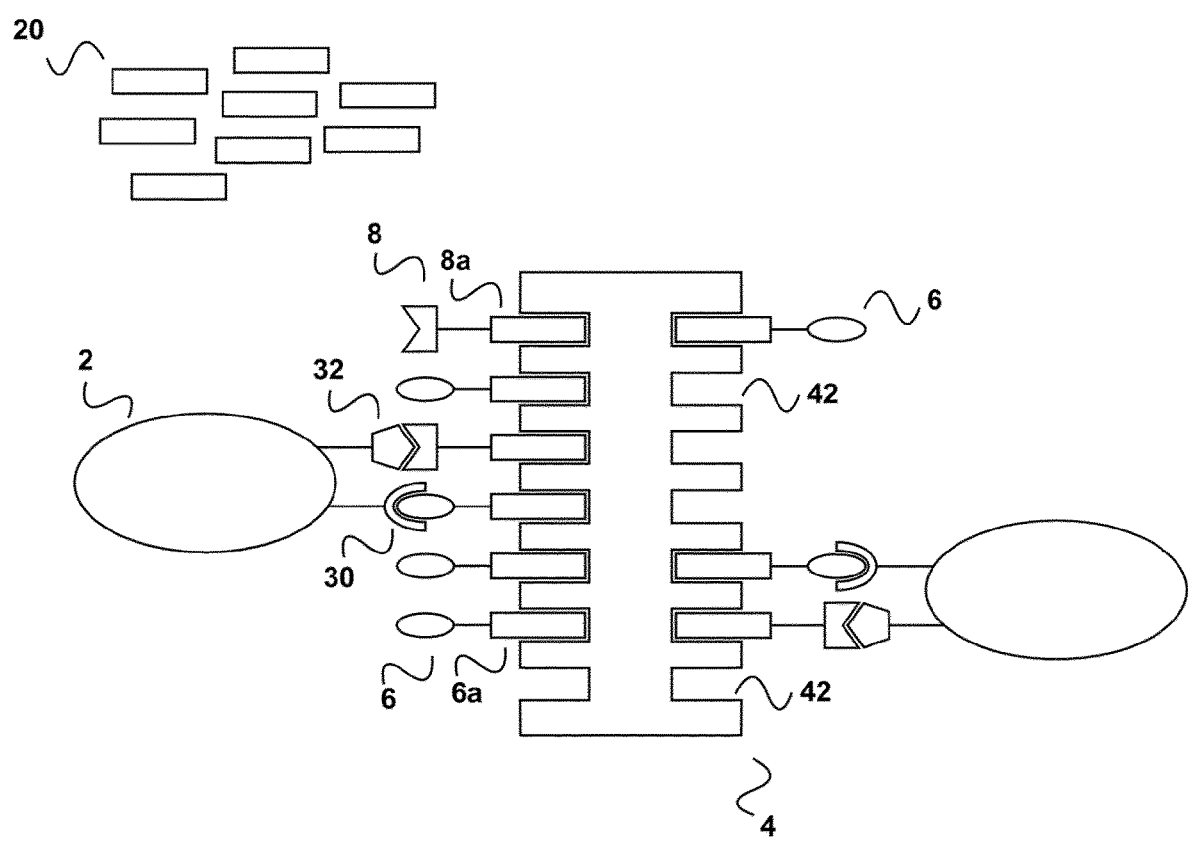

Using as binding partners C1 and C2, moieties that bind to the same binding site (42) of the multimerization agent has the advantage that, as shown in FIG. 3b, the same free partner (of the first binding partner C1 and also of the second binding partner C2) or analogue thereof can be used to terminate the expansion of the population of T cells (2) and to release this population of T cells (2) from the multimerization agent. In the Example of FIG. 3, an analogue of the first and second partner C1 and C2 such as biotin or a biotin derivate (iminobiotin or desthiobiotin) can be conveniently used for the termination of the expansion and the elution of the population of T cells (2).

Figure 3C:
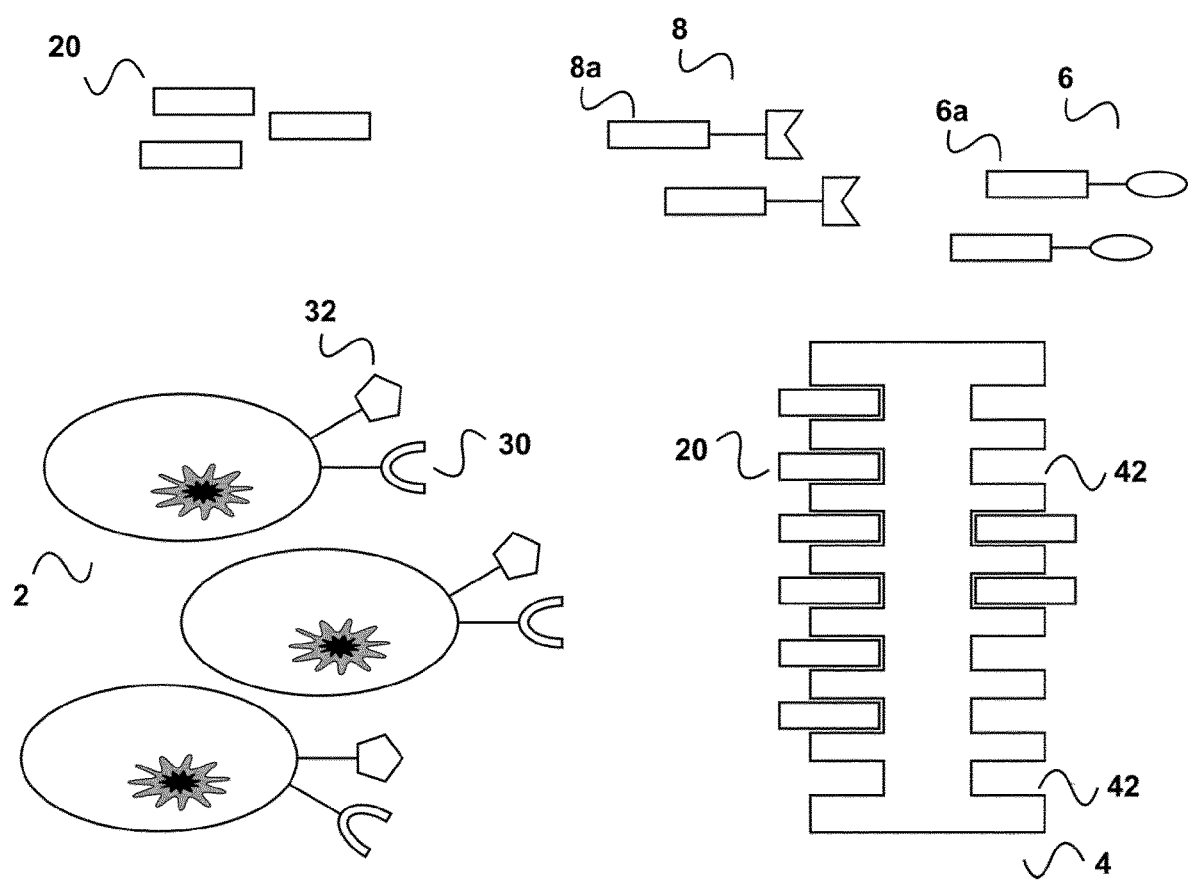

As shown in FIG. 3c, after the elution of the cells as illustrated in FIG. 1d, the first agent (6), the second reagent (8) as well as biotin as the analogue (20) of free first partner of the binding partner C1 and the second free partner of the binding partner C2 can be easily removed from the stimulated cell population (2) via a "removal cartridge" described in International patent application WO 2013/124474. In addition, the embodiment of using a soluble multimerization reagent (4) has the further advantage of being able to avoid any solid support such as magnetic beads. This means there is no risk of contamination of the activated T cells by such magnetic beads. This also means that a process that is compliant with GMP standards can be much easier established compared to the known method such as the use of Dynabeads® in which additional measures have to be taken to ensure that the final expanded T cell population is free of magnetic beads. Furthermore, the use of a soluble multimerisation agent makes it much easier to remove the same from the activated cell population (T cells, B cells or also natural killer cells) since the cells can be simple sedimented by centrifugation and the supernatant including the soluble multimerization agent can be discarded. Alternatively, the soluble multimerization agent can be removed from the expanded cell population in a gel permeations matrix of the removal cartridge of International patent application WO 2013/124474. Since no solid phase (e.g. magnetic beads) are present, the present invention also provides for an automated closed system for expansion of the cells that can be integrated into known cell expansion systems such as the Xuri Cell Expansion System W25 and WAVE Bioreactor 2/10 System, available from GE Healthcare (Little Chalfont, Buckinghamshire, United Kingdom) or the Quantum® Cell Expansion System, available from TerumoBCT Inc. (Lakewood, Colo., USA).

Figure 4B:
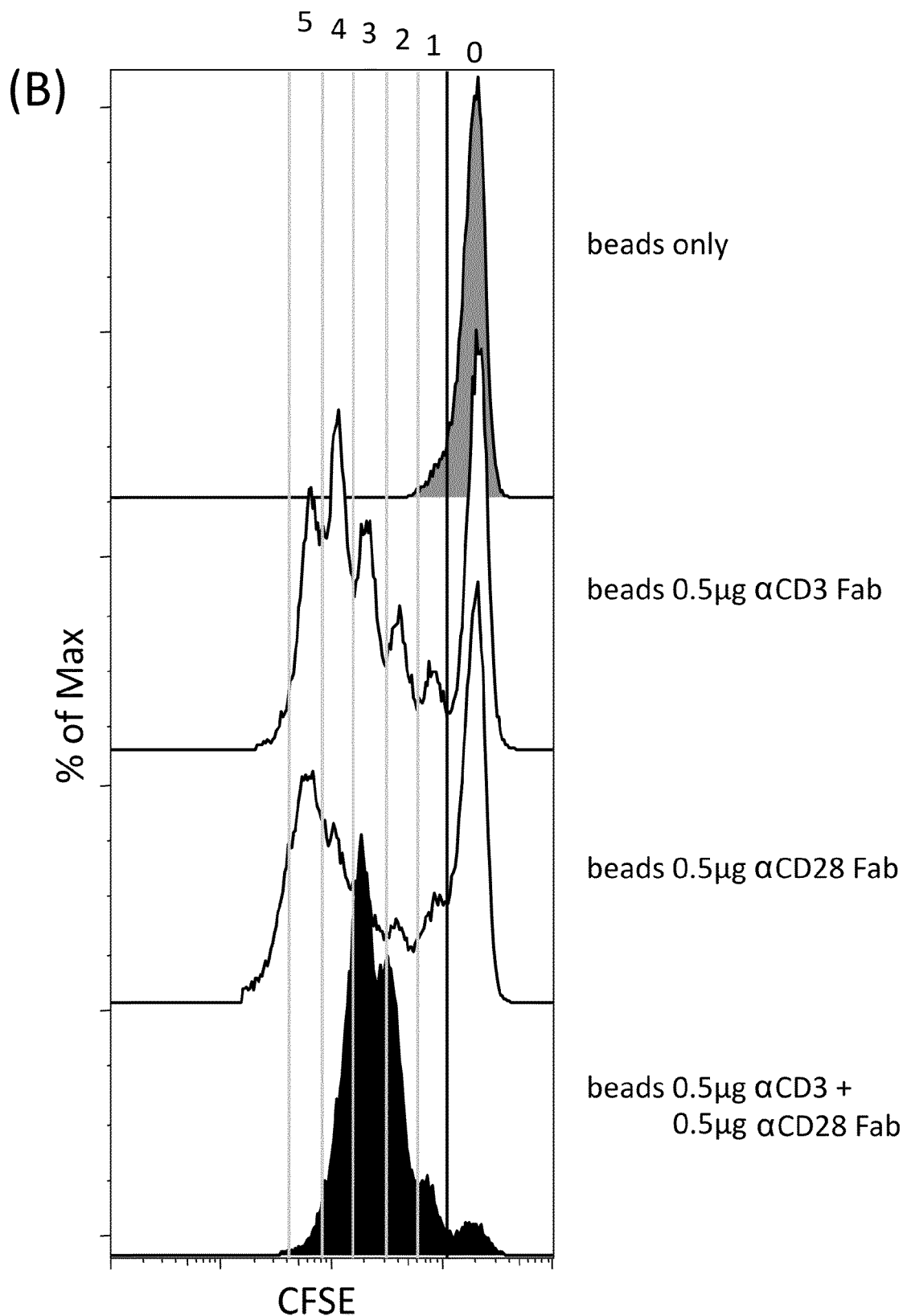
Figure 4C:
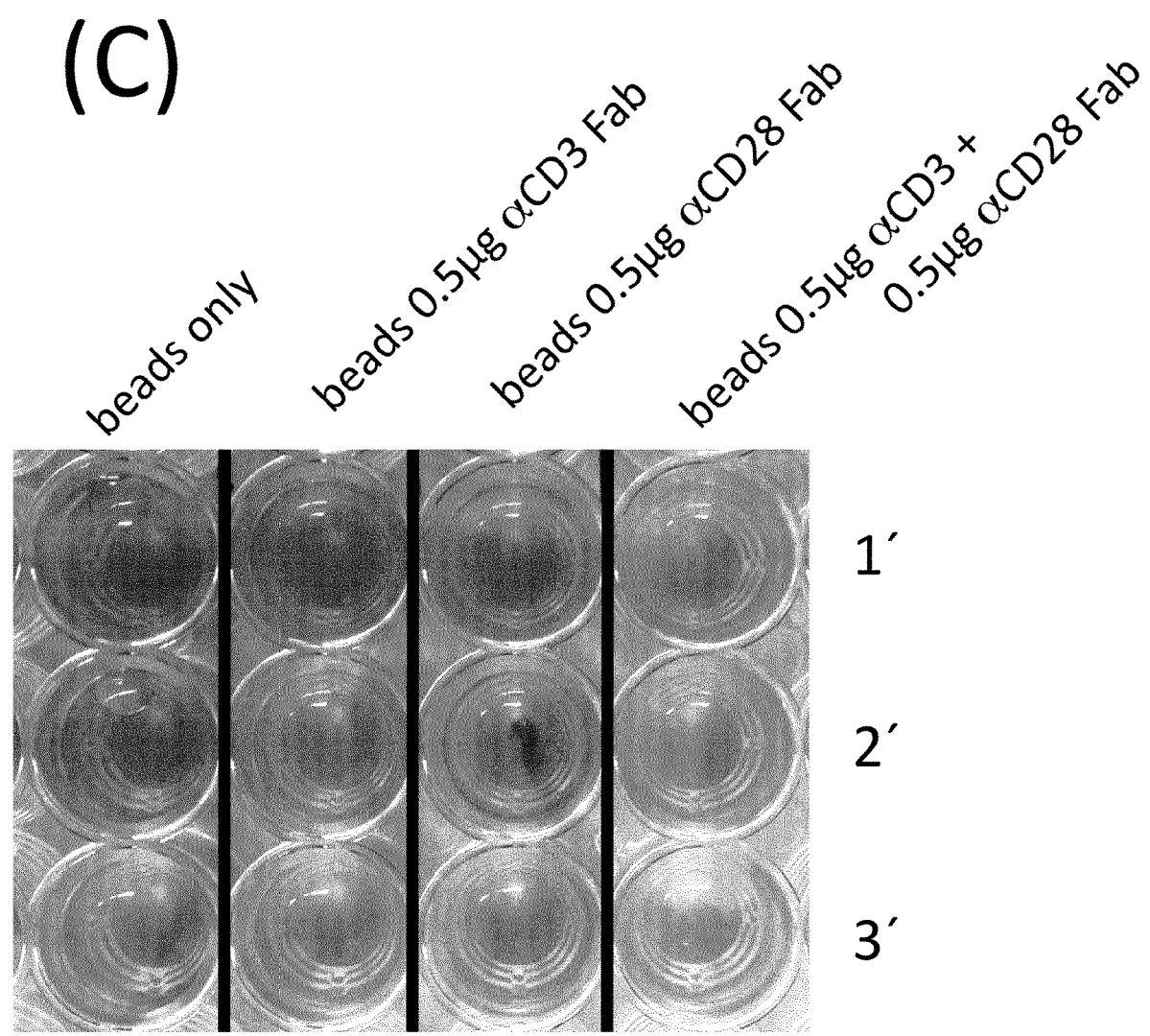

FIG. 4 shows the results of an experiment in which CD3+ T responder cells were proliferated after being stimulated in vitro with αCD3 and αCD28 Fab fragments that were reversibly immobilized on beads coated with the streptavidin mutein Strep-tactin®. FIG. 4A in a histogram showing size-distribution (forward scatter) of stimulated cells, FIG. 4B depicts histograms representing the degree of proliferation according to the number of cells per cell division that are indicated on top of FIG. 4B (0 represents undivided cells; 5 represents cells that have gone through at least 5 divisions), and FIG. 4C shows a picture of the culture dish after 4 days of stimulation.

Figure 5A:
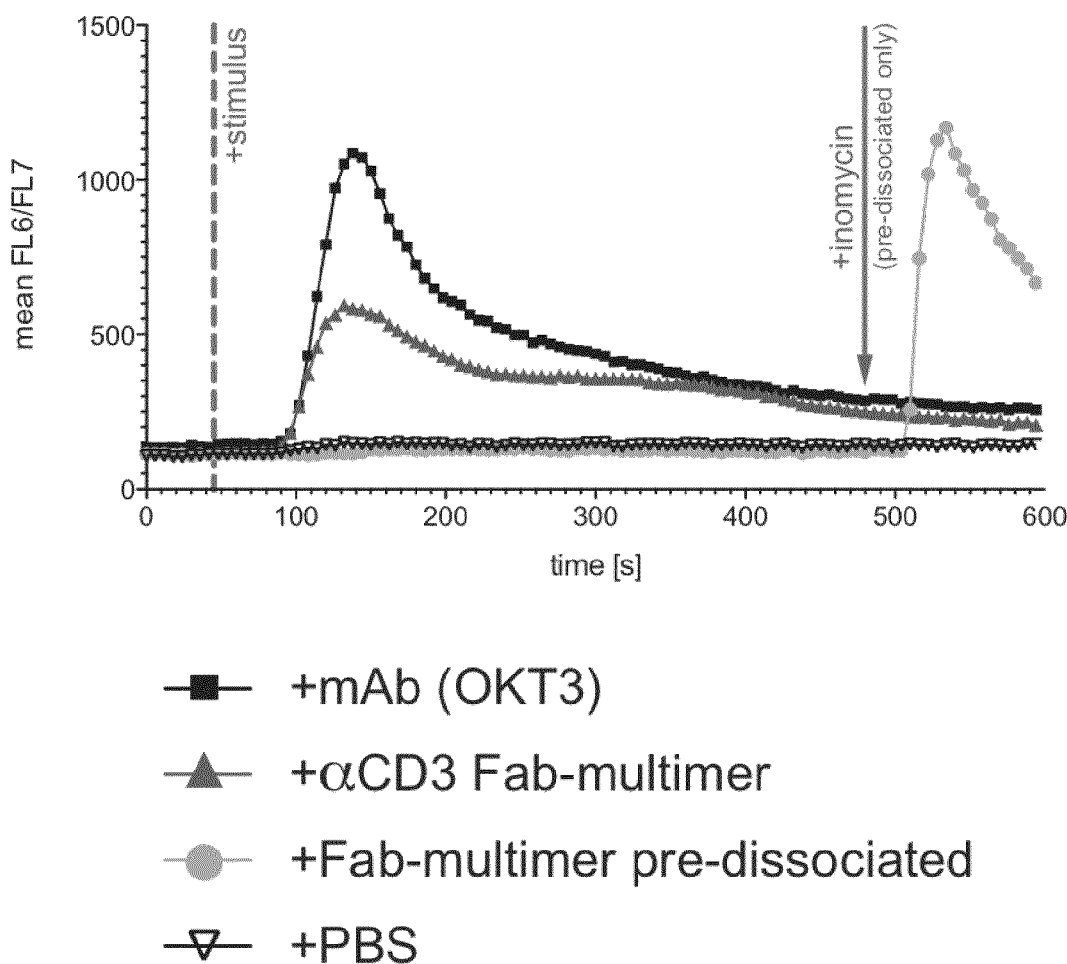
Figure 5B:
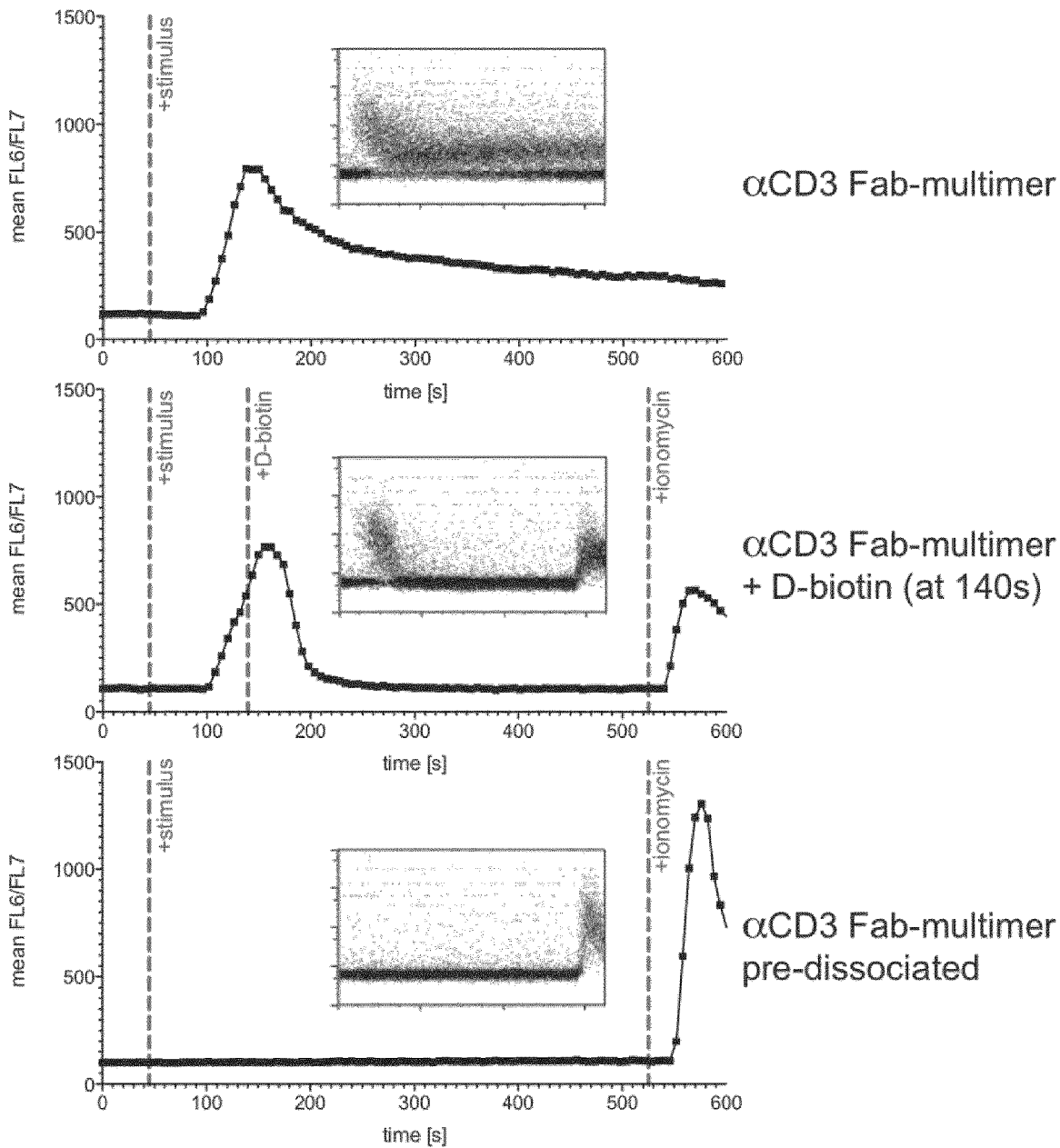

FIG. 5 shows the results of the differential intracellular calcium mobilization in Jurkat cells that are either labelled with the αCD3 antibody OKT3 or with Fab fragments of OKT3 being multimerized with Strep-tactin® (also referred to as Fab multimers herein). FIG. 5A: Jurkat cells were loaded with the calcium-sensitive dye Indo-1-AM and calcium release was triggered by injection of either αCD3 mAb (black squares) or αCD3 OKT3 Fab multimers (derived from the parental cell line OKT3) with or without prior D-biotin disruption (dark grey triangles and light grey circles respectively) compared to injection of PBS (inverted white triangles). Application of ionomycine served as positive control. Time-resolved changes in intracellular $Ca^{2+}$ concentration were monitored by flow-cytometry based on the change in FL6/FL7 ratio. FIG. 5B: Indo-1-AM-labeled Jurkat cells were activated by different αCD3 stimuli as described in FIG. 4a; OKT3: upper graph and αCD3 Fab-multimer: middle graph) followed by subsequent (t=140 s) D-biotin mediated disruption of αCD3 Fab-multimer signaling. Injection of PBS (lower graph) and ionomycine served as negative or positive control. Data are representative of three different experiments.

Figure 6:
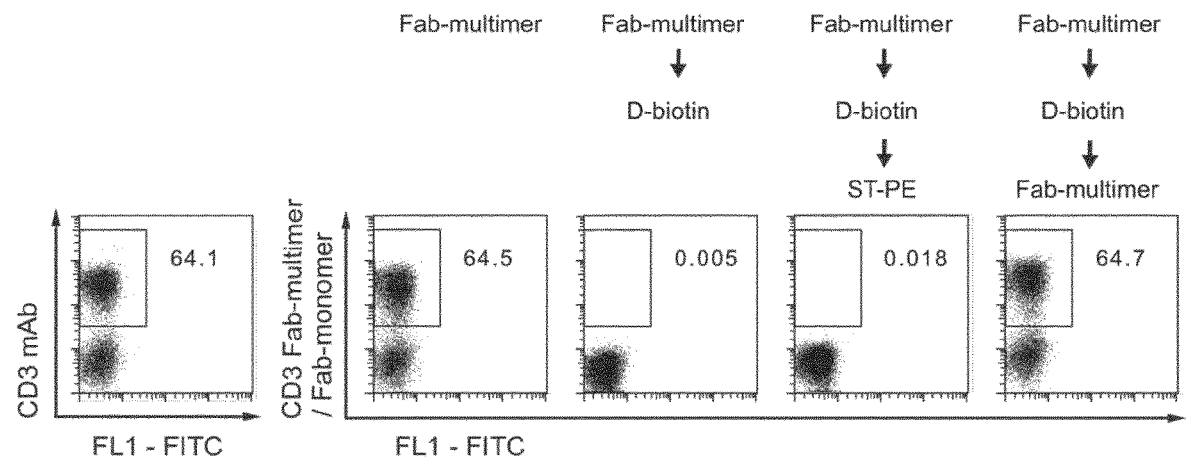

FIG. 6 shows the result of the reversible staining of cells by anti CD3 OKT3 Fab-multimers. Freshly isolated PBMCs were stained with either a monoclonal antibody (left dot plot, parental clone for the Fab-multimers) or cognate PE-labeled Fab-multimers and analyzed either before (second left column) or after treatment with D-biotin (middle column). Remaining Fab monomers were then detected after subsequent washing steps using fresh PE-labeled Strep-Tactin® (second right column). Secondary Fab-multimer staining of reversibly stained cells served as control (right column). Only live ($PI^{negative}$) cells are shown. Numbers in dot plots indicate the percentage of cells within gates.

Figure 7:
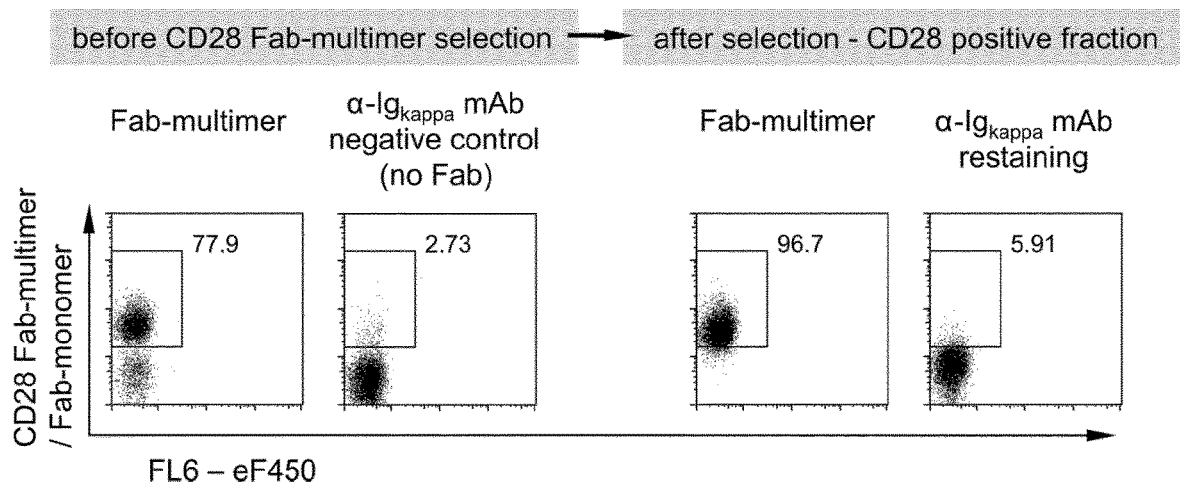

FIG. 7 shows the isolation of cells by reversible binding of anti-CD28 Fab fragments multimerized with Strep-Tactin® labeled with phycoerythrine as a fluorescent label. CD28+ cells were selected/isolation by Fab-multimer magnetic cell selection from freshly isolated PMBCs as described in International Patent Application WO2013/011011. Before selection cells were control stained with either the cognate fluorescent aCD28-multimers (left dot plot) or with an antibody directed against the immunoglobulin kappa light chain (second left dot plot, α-Ig kappa mAb). After selection, cells were treated with D-biotin and subsequently washed to remove magnetic beads and Fab-monomers. Liberated CD28+ cells were subsequently (re-)stained either with CD28 Fab-multimers (second right dot plot) or with the α-Ig kappa mAb (right dot plot) to detect potentially remaining Fab-monomers. Only live ($PI^{negative}$) CD3+ cells are shown. Numbers in dot plots indicate the percentage of cells within gates.

Figure 8:
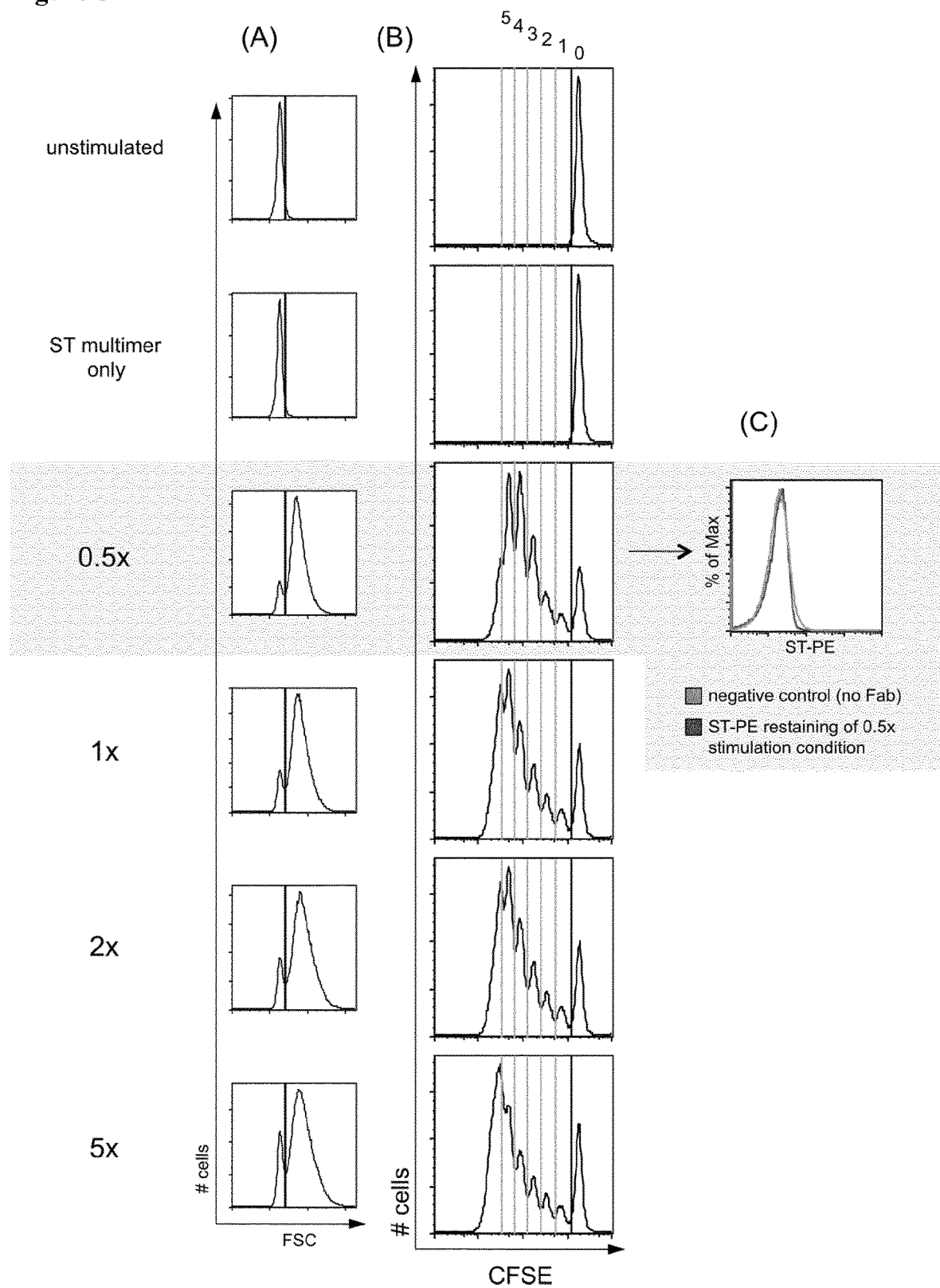
Figures 8, 8D:
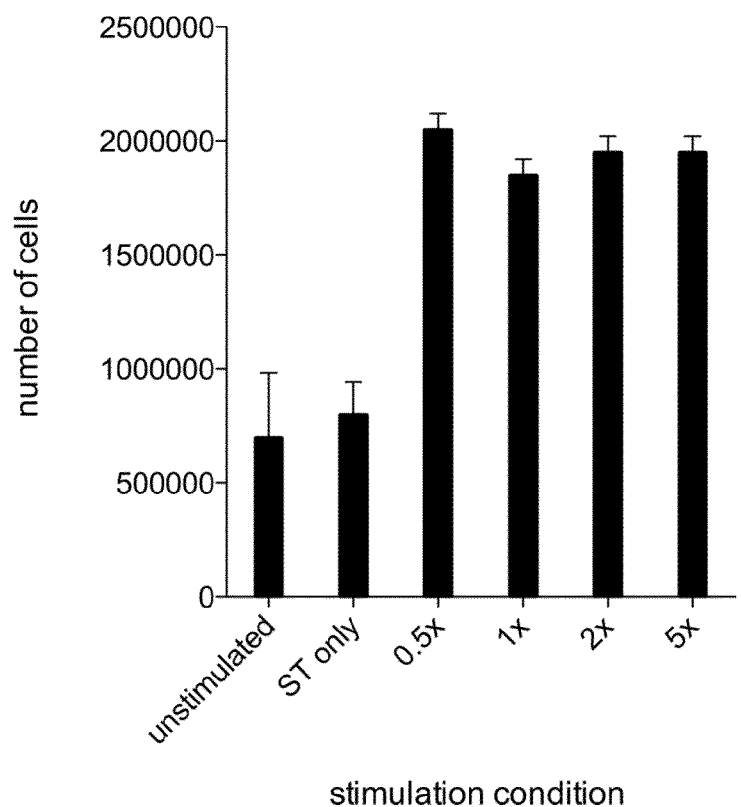
Figures 8, 8E:
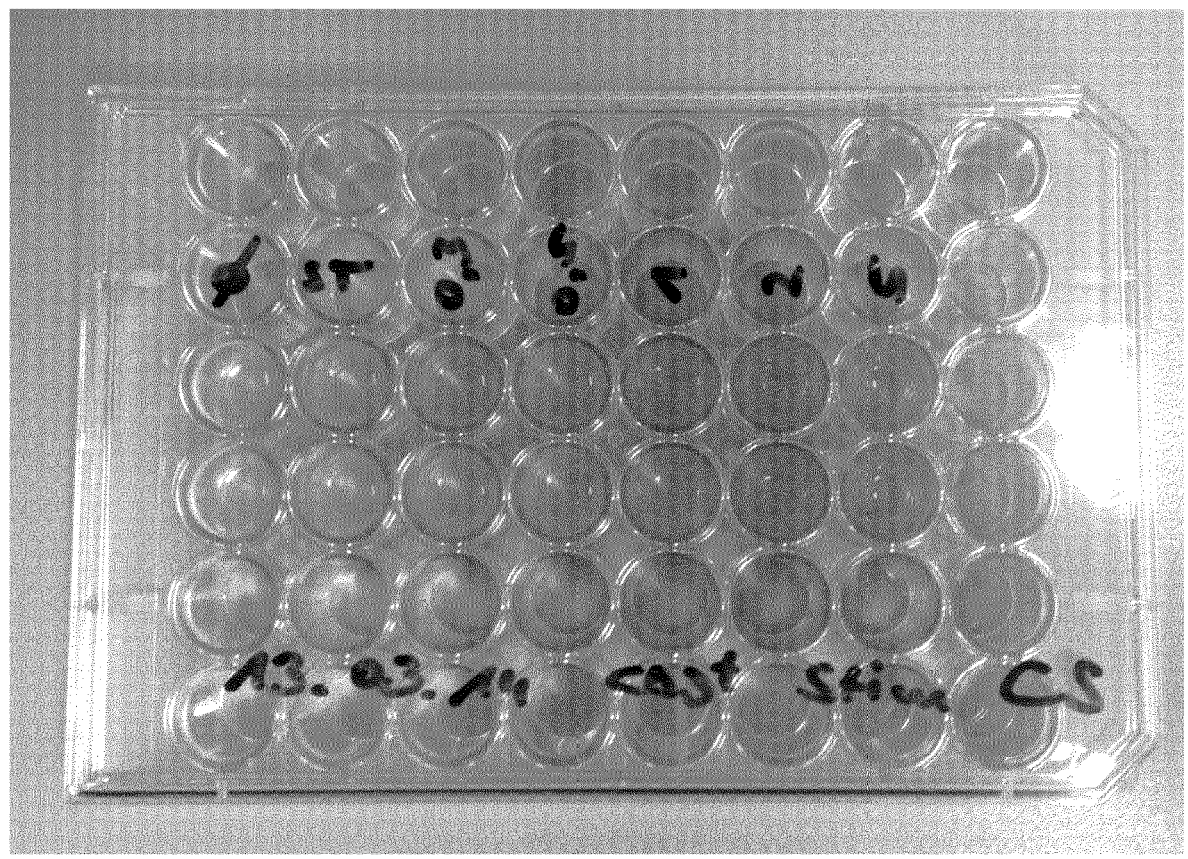

FIG. 8 shows the results of an experiment in which CD3+ T responder cells were proliferated after being stimulated in vitro with reversible αCD3/αCD28 Fab fragments that were reversibly immobilized on soluble oligomeric Strep-tactin® acting a soluble multimerization reagent. For the experiments the results of which are shown in FIG. 8, 300.000 CD3+ responder T cells (Tresp) were labeled with 2 μM Carboxyfluorescein succinimidyl ester (CFSE) and stimulated with varying amounts of a preparation of soluble Streptactin oligomers on which a combination of αCD3 Fab fragment and αCD28 Fab both carrying a Strep-tag as streptavidin binding peptide at the heavy chain were immobilized. ("1×" corresponds to 3 μg multimerized Strep-tactin functionalized with 0.5 μg αCD3- and 0.5 μg αCD28 Fab; numbers indicate fold amount of "1×"). Tresp cells either left unstimulated or were stimulated with blank Strep-tactin multimers (no Fab) served as negative control. Tresp cells were seeded in duplicates in 48-well plates along with 300.000 CD3 negative autologous feeder cells (irradiated with 30 Gy) in 1 ml cell culture medium supplemented with 20 U/ml interleukin 2 (IL-2). Cells were incubated at 37° C. without media exchange and proliferation was analyzed according to CFSE dilution after 5 days by FACS analysis (FIG. 8B). FIG. 8A shows size distribution of cells after 5 days in culture. Histograms show live CD3+ cells, while FIG. 8C shows cells after culture that were liberated by stimulation reagents after treated with 1 mM D-biotin and washed. The dissociation and removal of monomeric Fab fragments was analyzed by restaining with Strep-Tactin® labeled with phycoerythrine (ST-PE) as a fluorescent label and a representative histogram is shown. FIG. 8D shows the absolute number of live (trypan blue negative) cells after 5 days was counted using a Neubauer counting chamber and plotted against the respective stimulation condition. Median cell numbers are shown in FIG. 8D; error bars indicate standard deviation (SD). FIG. 8E shows a picture of the culture dish after 5 days of stimulation.

FIG. 9 depicts an illustration of the serial expansion method of the present invention (FIG. 9*a*) while FIG. 9*b* briefly describes some features and advantages of the serial expansion.

Figure 10:
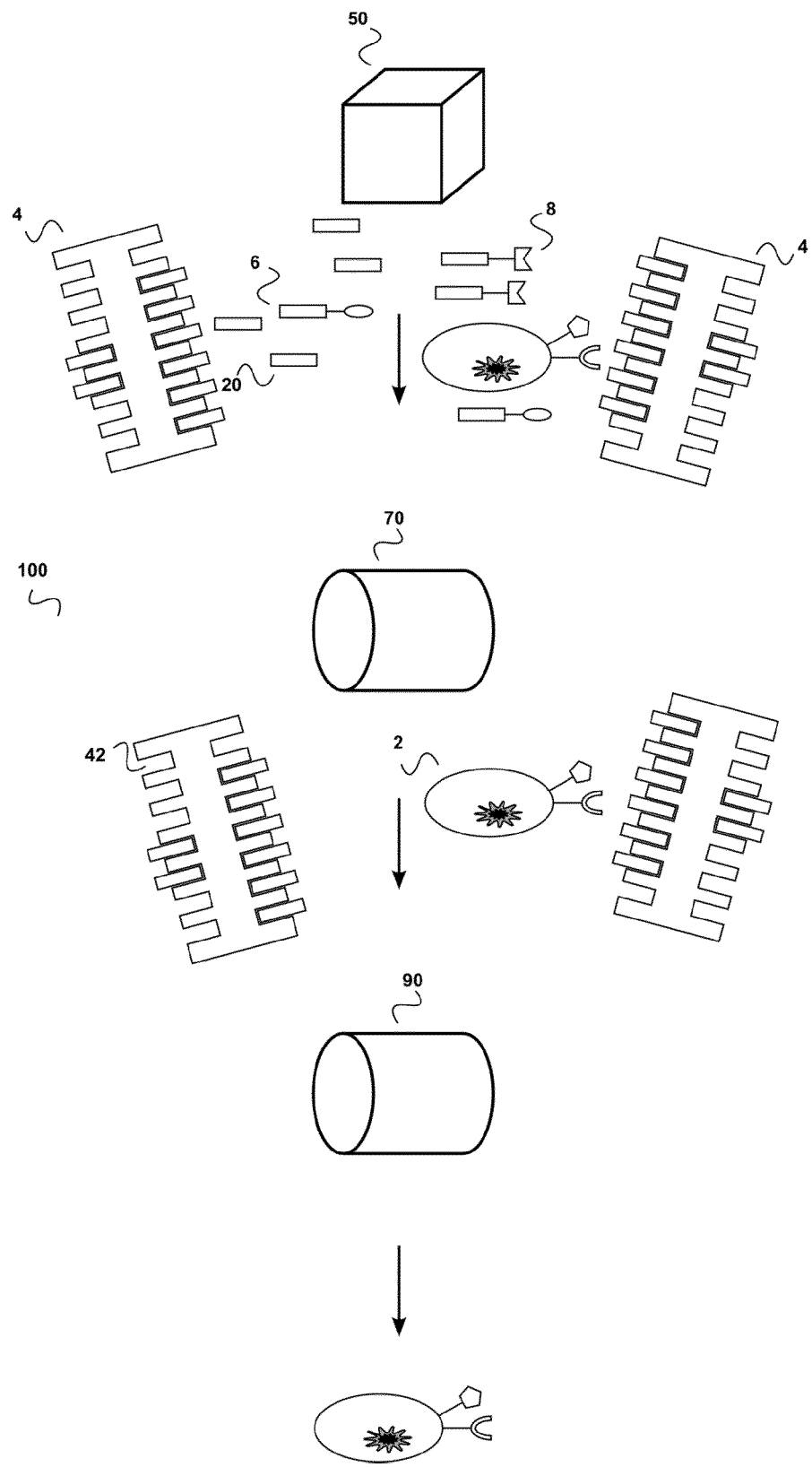

FIG. 10 shows an arrangement of the invention that can be used together with the expansion methods of the invention. This arrangement (100) includes a bioreactor (50), a first "removal cartridge" (70) and a second "removal cartridge" (90). The bioreactor (50) is fluidly connected to the first removable cartridge (70), and the first removal cartridge is fluidly connected to the second removal cartridge (90). This arrangement (100) can be part of a device for automated cell expansion and purification as described here.

In the bioreactor (50) an expansion method as described herein is carried out, for example an expansion method illustrated in FIG. 3 that makes use of a soluble multimerization reagent. In this case, after termination of the activation/expansion of the cell population (2) by addition of a competitor (20) (free partner of the binding partner C1 or an analogue thereof) the reaction mixtures that is released from the bioreactor contains the expanded population of cells (2), the first agent (6), the second agent (8) as well as the soluble multimerization reagent (4). In this example, the first agent (6) is a CD3 binding antibody fragment that includes a streptavidin binding peptide as binding partner C1, the second agent (8) is a CD28 binding antibody fragment that includes a streptavidin binding peptide as binding partner C1 and the competitor (20) (free analogue of the binding partner C1) is biotin. This reaction mixture is applied on the first removal cartridge (70). This first removal cartridge (70) is a removal cartridge as described in International patent application WO 2013/124474 that includes a chromatography column with a suitable stationary phase. The stationary phase can serve both an affinity chromatography matrix and, at the same time, can act as gel permeation matrix. This affinity chromatography matrix has an affinity reagent immobilized thereon. The affinity reagent may, in the case of the current Example, for instance, be streptavidin, a streptavidin mutein, avidin, an avidin mutein or a mixture thereof. Thus, the first agent (6) and the second agent (8) bind to the affinity reagent via their streptavidin binding peptide. Also biotin as the competitor (20) binds to the affinity reagent. Thus, these three reagents are all being immobilized on the chromatography matrix of the first removal cartridge while the expanded cell population (2) and the soluble multimerization reagent (4) pass through the stationary phase. This "flow through" is then applied onto the second removal cartridge (90). Also this second removal cartridge (90) comprises a stationary phase. This stationary phase comprises a second affinity reagent thereon which is able to bind to the binding site Z1 (42) of the multimerization reagent (4). This affinity reagent may for example be biotin that is covalently bound to the stationary phase. Such a stationary phase may, for example, be d-biotin Sepharose™ obtainable from Affiland S. A. (Ans-Liege, Belgium). Thus, the soluble multimerization reagent (4) will be bound (retained) on the stationary phase of the second removal cartridge (90) while the expanded population of cells (2) passes through the stationary phase and is being freed of any reactants. The population of cells (2) is now in a condition for any further use, for example, for diagnostic applications (for example, further FACS™ sorting) or for any cell based therapeutic application. It is noted here that it is of course also possible to change the order of the first "removal cartridge" (70) and the second "removal cartridge" (90) in an arrangement (100), such that bioreactor (50) is (directly) fluidly connected to the second removable cartridge (90), and the first removal cartridge (70) is arranged after and fluidly connected to the second removal cartridge (90). In this arrangement the multimerization reagent (4) will first be removed from the population of cells (2) and subsequently the first agent (6), the second (8) and e.g. the competitor (20) are removed. Such an arrangement is also encompassed in the present invention and can also be part of a device for automated cell expansion and purification as described here.

Figure 11:
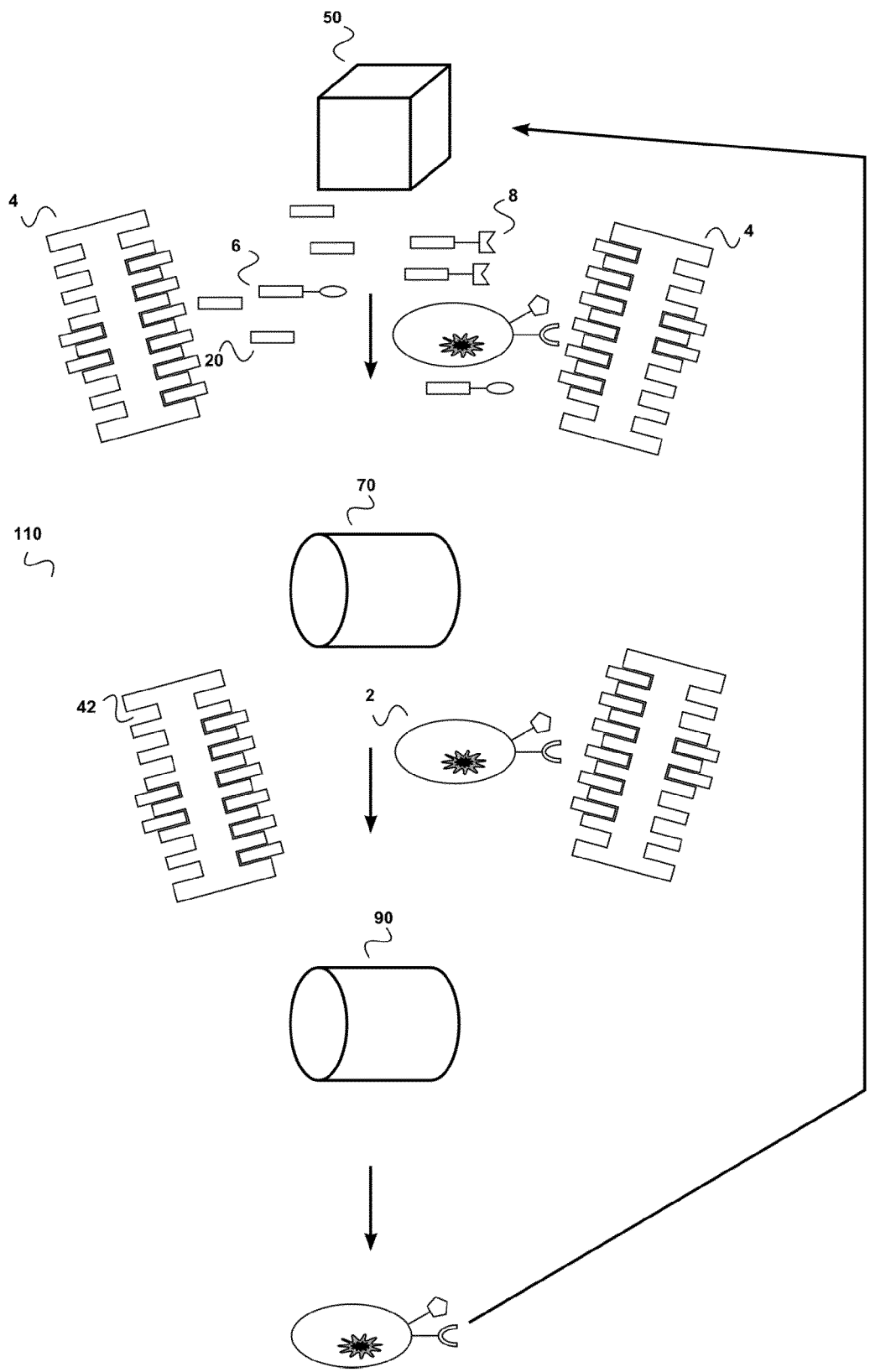

FIG. 11 shows a further embodiment of an arrangement of the invention that can be used together with the expansion methods of the invention. This arrangement (110) includes a bioreactor (50), a first "removal cartridge" (70) and a second "removal cartridge" (90). The bioreactor (50) is fluidly connected to the first removable cartridge (70), and the first removal cartridge is fluidly connected to the second removal cartridge (90). In addition, the second removal cartridge (110) is fluidly connected to the bioreactor (50). This arrangement (110) can also be part of a device for automated cell expansion and purification as described here. When used, for example, together with an expansion method that employs a soluble multimerization reagent (4), a purified expanded population of cells (2) is obtained as eluate of the second removal cartridge (90). Since the removal cartridge (90) is fluidly connected to the bioreactor (50), the population of cells (2) can be transferred back into the bioreactor (50), for example, to serial clonal expansion as described here, by transfecting the population of cells, for example, with the gene of an T cell receptor and subsequent further (second) expansion using an expansion method of the invention.

Figure 12:
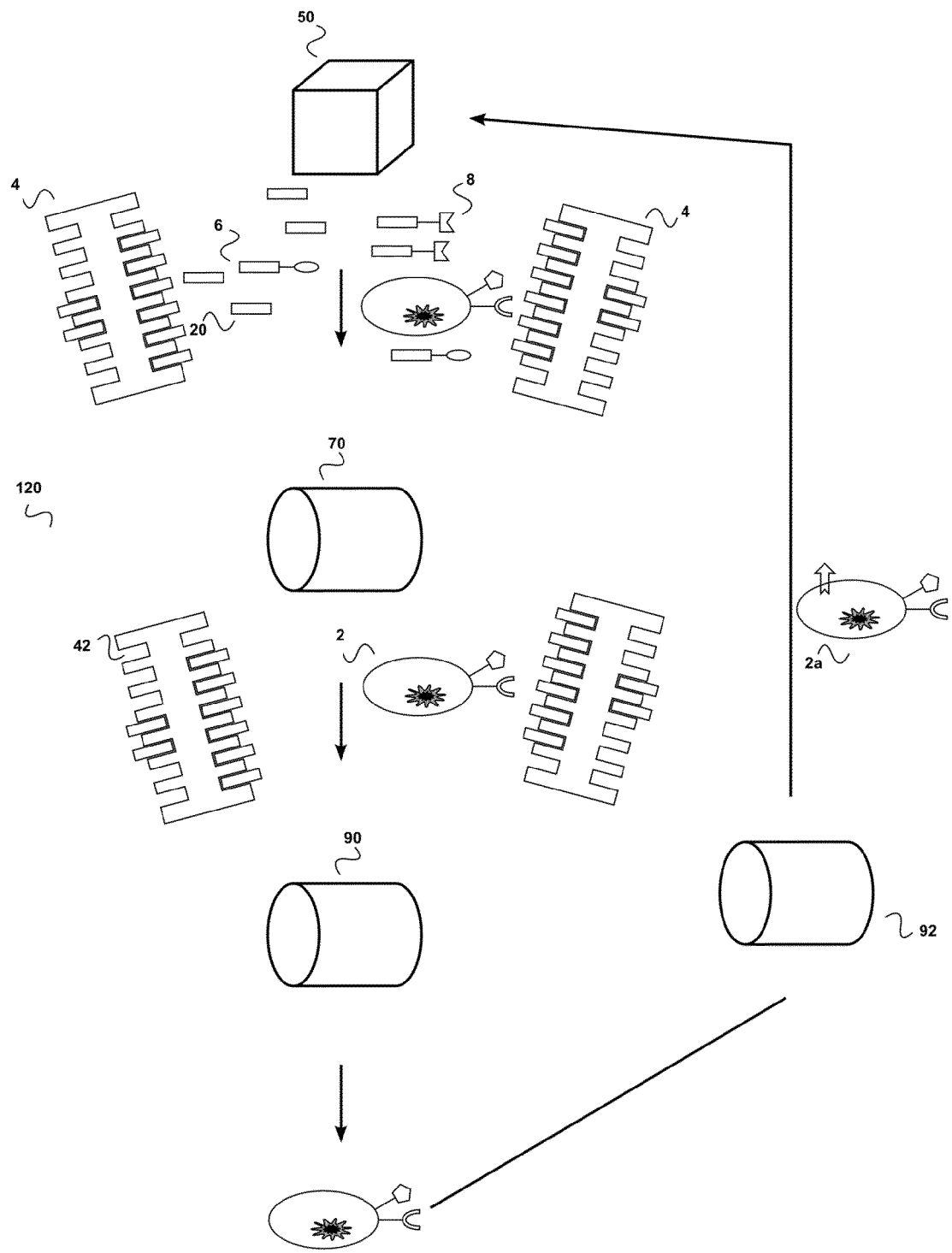

FIG. 12 shows a further embodiment of an arrangement of the invention that can be used together with the expansion methods of the invention. This arrangement (120) includes a bioreactor (50), a first "removal cartridge" (70) and a second "removal cartridge" (90). The bioreactor (50) is fluidly connected to the first removable cartridge (70), and the first removal cartridge is fluidly connected to the second removal cartridge (90). Similar to the embodiment shown in FIG. 11, the second removal cartridge (110) is fluidly connected to the bioreactor (50). However, a "selection cartridge" (92) as described in International patent application WO 2013/124474 is arranged in between the second removal cartridge (90) and the bioreactor (50). Thus, a subpopulation of cells (2*a*) that is comprised in the population of cells (2) can be selected/enriched via this "selection cartridge" (92) as described in WO 2013/124474. This subpopulation of cells (2*a*) can either be transferred into the bioreactor (50), for example, to undergo serial expansion as described here. Alternatively (not shown), this subpopulation of cells (2a) can be used for cell based therapy. It is again noted here that the use of a soluble multimerization reagent as described here allows the design of automated cell purification and expansion devices which are functionally closed and thus not prone to contamination. In addition, since soluble multimerization reagent avoids the need for solid phase materials such as magnetic beads, such cell purification devices can be designed as continuous flow devices.

Figure 13:
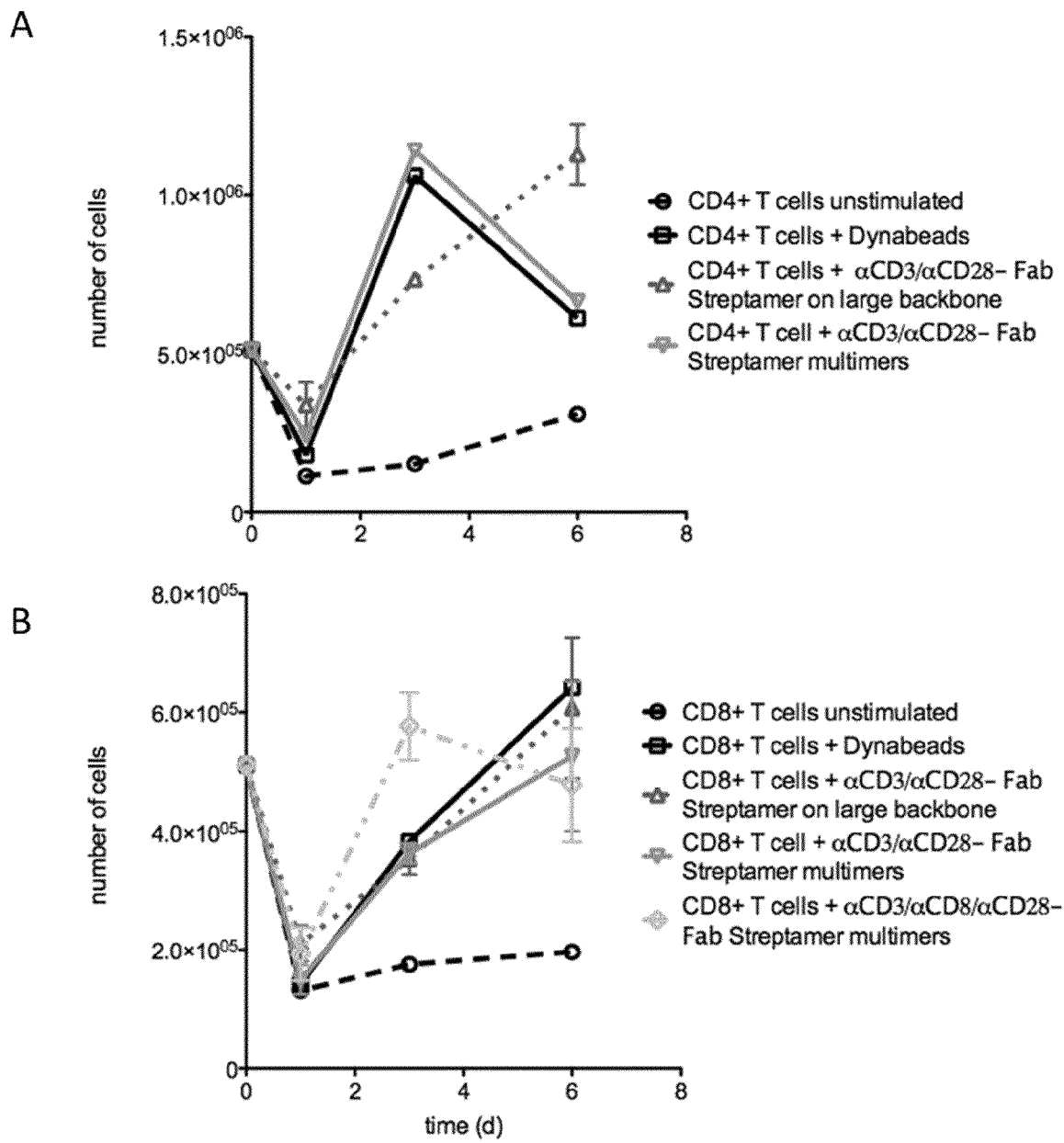

FIG. 13 shows the expansion kinetics of proliferation of purified CD4+ and CD8+ T responder cells (Tresp) that were stimulated in vitro either with αCD3/αCD28 Fab fragments or with αCD3/αCD28/αCD8 that were reversibly immobilized on two kinds of a soluble oligomeric Strep-tactin® mutein acting as soluble multimerization reagent. The first kind of oligomeric Strep-tactin® was the fraction of the oligomeric streptavidin mutein (n≥3) obtained in Example 5 (also referred herein as "conventional Streptactin® backbone", illustrated by the triangle symbol with the tip down in FIG. 13), the second kind of this oligomeric streptavidin mutein used as soluble multimerization reagent was an oligomer that was obtained by reacting the soluble oligomeric streptavidin mutein with biotinylated human serum albumin (HSA) This HSA based soluble multimerization reagent is also referred herein as "large Streptactin® backbone). In the experiments of FIG. 13 the expansion was carried out without medium exchange. The results for the CD4+ T responder cells are shown in FIG. 13A, the results for the CD8+ T responder cells are shown in FIG. 13B. In this context, it is noted that the experimentally used soluble multimerization reagents that were functionalized by reversibly binding first agents, and optionally second and third agents are referred to in the Figures as "Streptamer® multimers"

Figure 14:
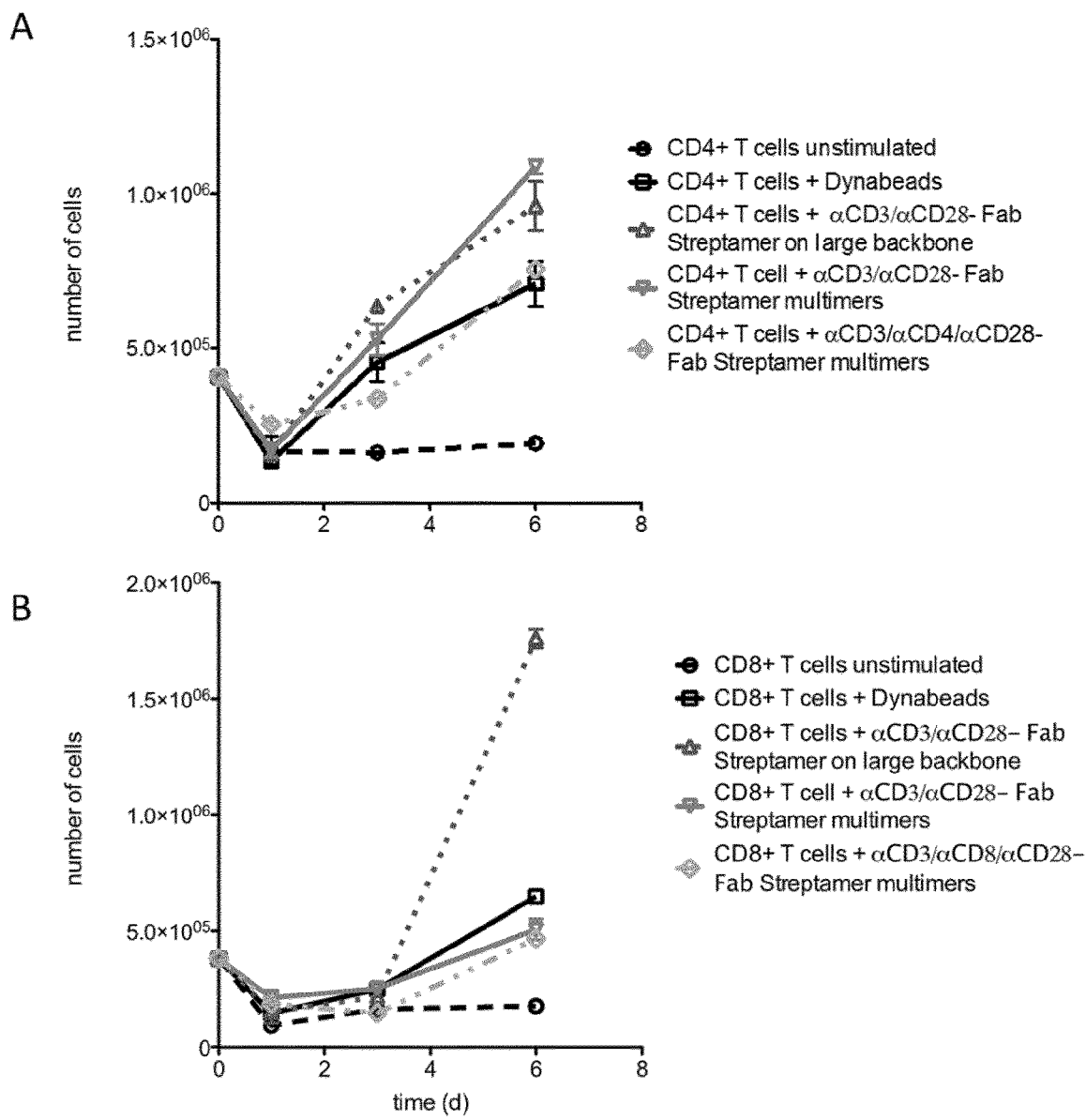

FIG. 14 shows the expansion kinetics of proliferation of purified CD4+ and CD8+ T responder cells (Tresp) that were stimulated in vitro with αCD3/αCD28 Fab fragments that were reversibly immobilized fragments that were reversibly immobilized with two kinds of soluble oligomeric Strep-tactin® acting as soluble multimerization reagent. The first kind of oligomeric Strep-tactin® was the fraction of the oligomeric streptavidin mutein (n≥3) obtained in Example 5 (also referred herein as "conventional Streptactin® backbone", illustrated by the triangle symbol with the tip on top in FIG. 14), the second kind of this oligomeric streptavidin mutein used as soluble multimerization reagent was the HSA based soluble multimerization agent, the above-mentioned "large Streptactin® backbone"). In the experiments of FIG. 14 the expansion was carried out with medium exchange. The results for the CD4+ T responder cells are shown in FIG. 14, the results for the CD8+ T responder cells are shown in FIG. 14B.

FIG. 15 shows the combined data from the results obtained in FIGS. 13 and 14 for the expansion kinetics of proliferation of purified CD4+ and CD8+ T responder cells, with FIG. 15A depicting the results for CD4+ T cells and FIG. 15B depicting the results for the CD8+ T cells. Straight lines are used for the culturing with medium exchange on day 3, while dashed lines depict the values obtained for the degree of expansion without media exchange on day 3. The data shown in FIG. 15 are normalized on the input cell number. Only data for the Tresp stimulated with the oligomeric streptavidin mutein (n≥3), the Tresp stimulated with the commercially available Dynabeads (positive control) and the unstimulated T cells (negative control) are shown but no data on the multimerization reagent with the "large Streptactin® backbone".

Figure 16:
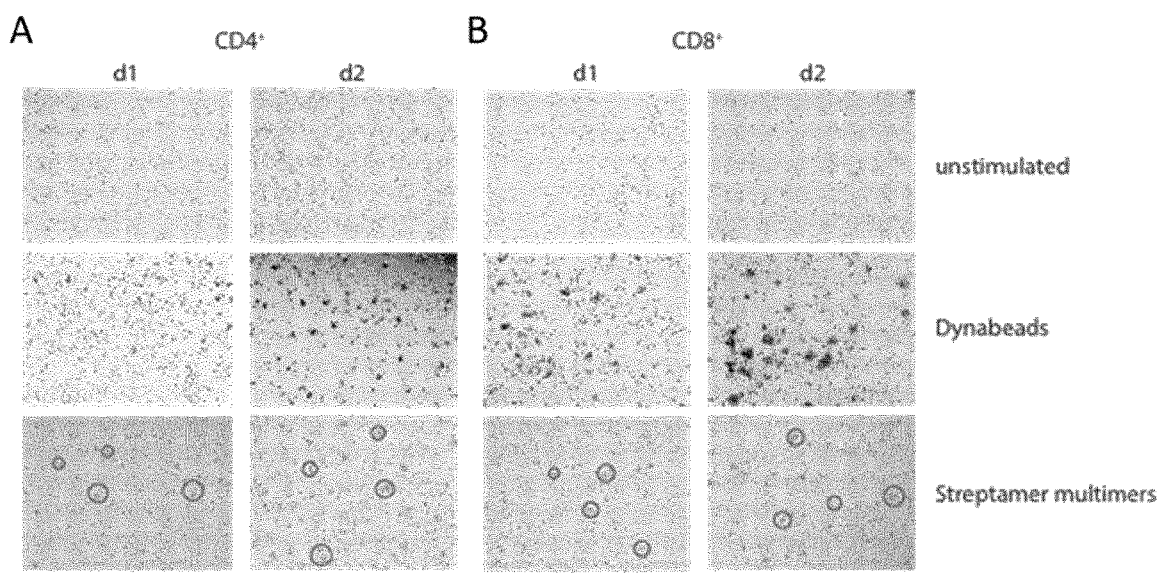

FIG. 16 shows early cluster formation of T cells after activation of purified CD4+ and CD8+ T responder cells stimulated in vitro with αCD3/αCD28 Fab fragments that were reversibly immobilized on the soluble oligomeric streptavidin mutein (n≥3) described in Example 5. FIG. 16A depicts the results for CD4+ T cells and FIG. 16B depicts the results for the CD8+ T cells. Data for the Tresp stimulated with the soluble multimerization reagent (the oligomeric streptavidin mutein), the Tresp stimulated with the commercially available Dynabeads (positive control) and the unstimulated T cells (negative control) are shown.

Figure 17:
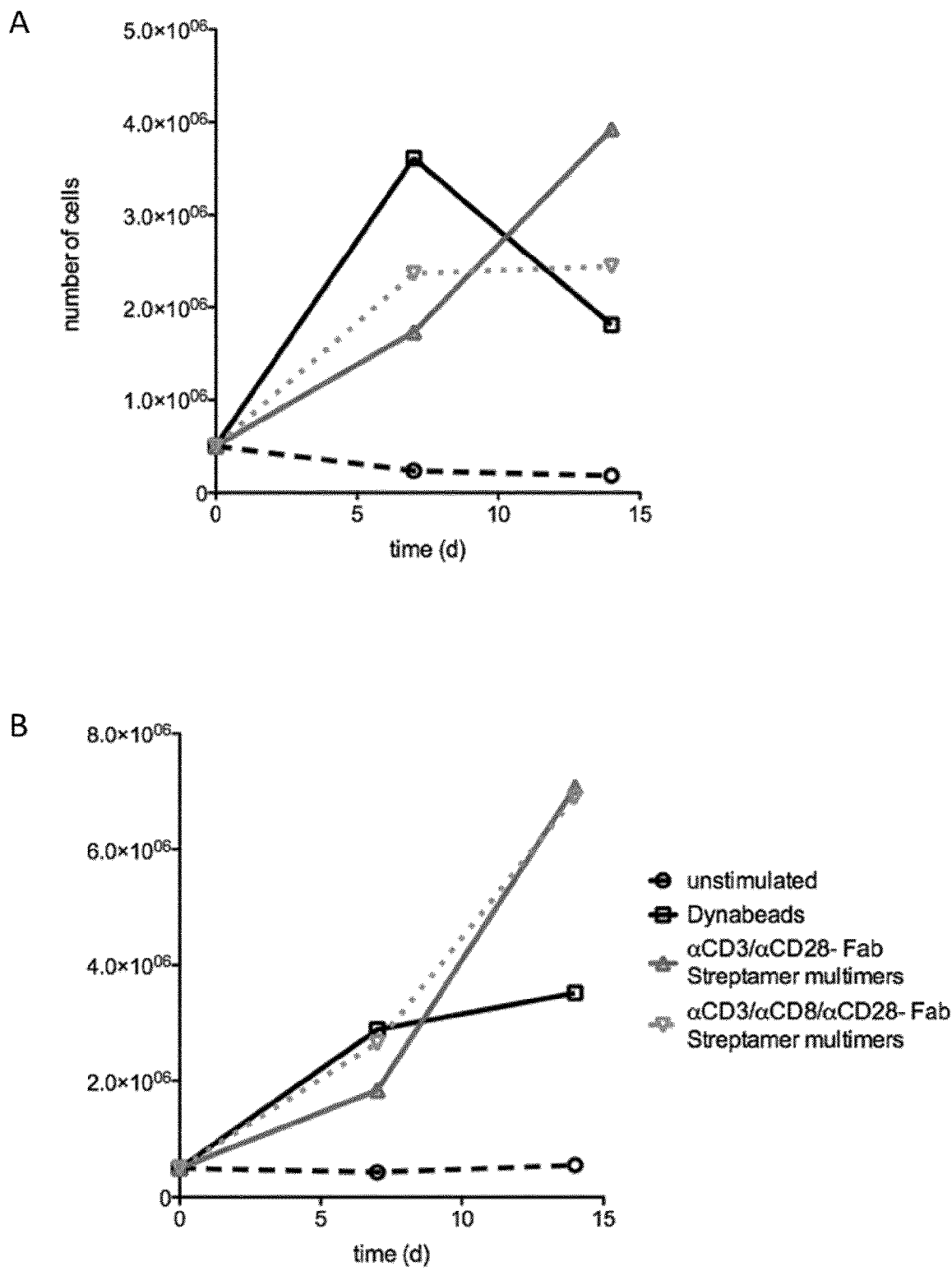
Figure 17:
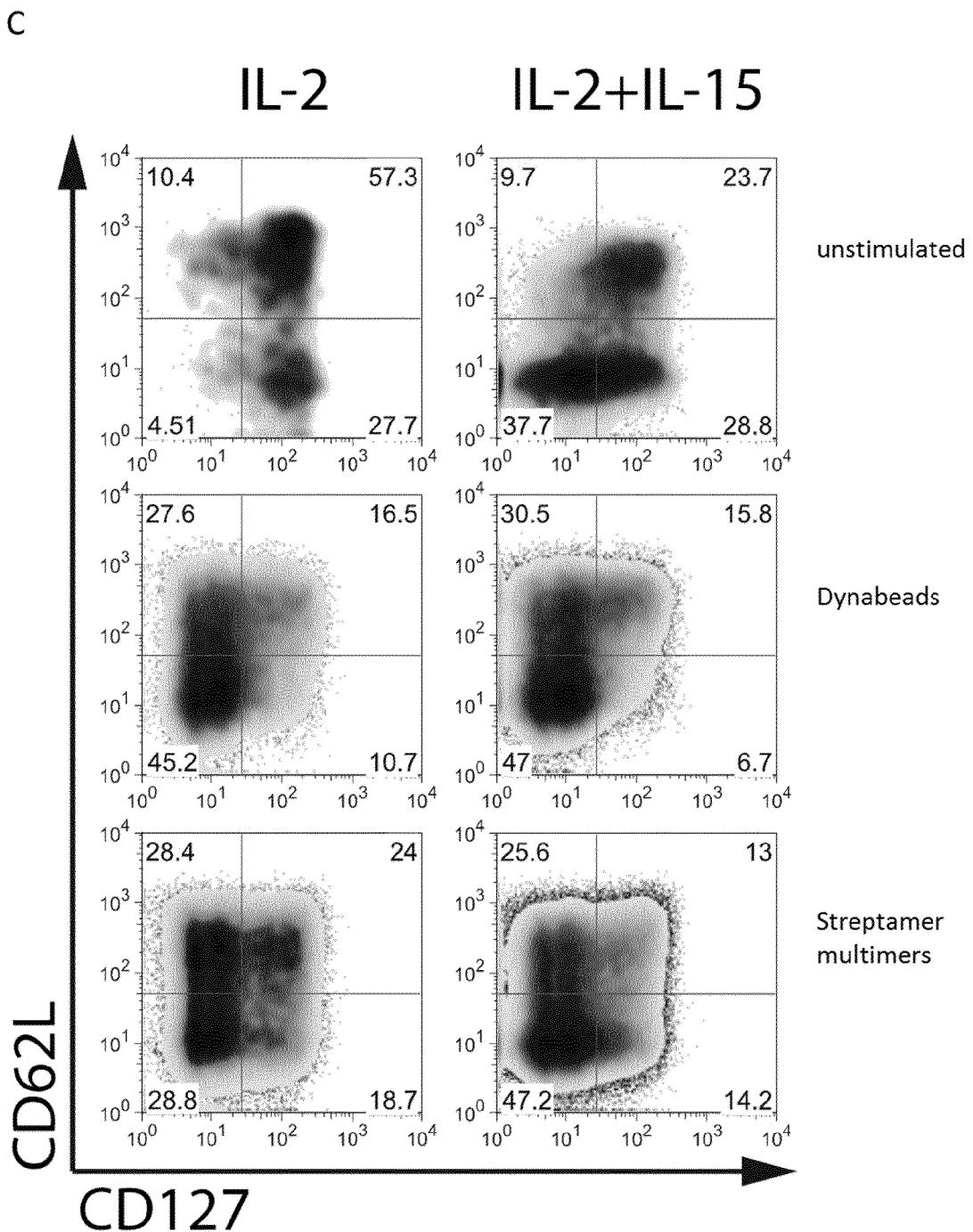

FIG. 17 shows the expansion kinetics and phenotype of CD3+ central memory T cells (Tcm) (CD3+CD62L+ CD45RA-Tcm) polyclonally stimulated in vitro with αCD3/ αCD28 Fab fragments that were reversibly immobilized on the soluble oligomeric streptavidin mutein (with n≥3) described in Example 5. The graphs shown in FIG. 17 represent the degree of proliferation according to the number of cells harvested per time point, with FIG. 17A showing the proliferation in only IL-2 supplemented media and in FIG. 17B showing the proliferation in IL-2 and IL-15 supplemented media. FIG. 17C shows a flow-cytometric analysis of CD62L and CD127 surface expression after 14 days of culture in these variable cytokine milieus.

Figure 18:
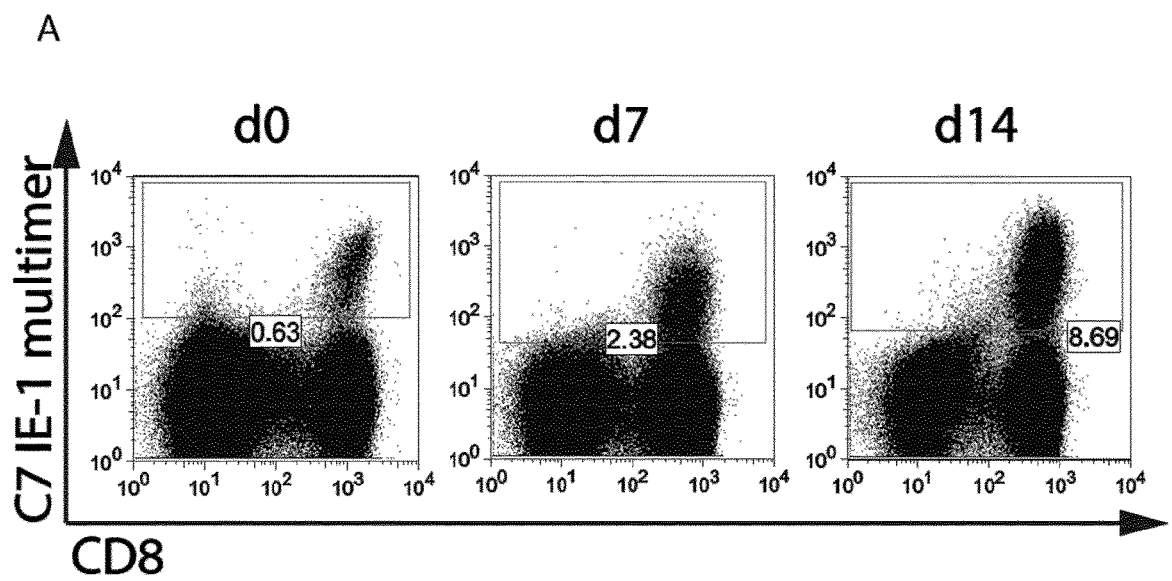
Figure 18:
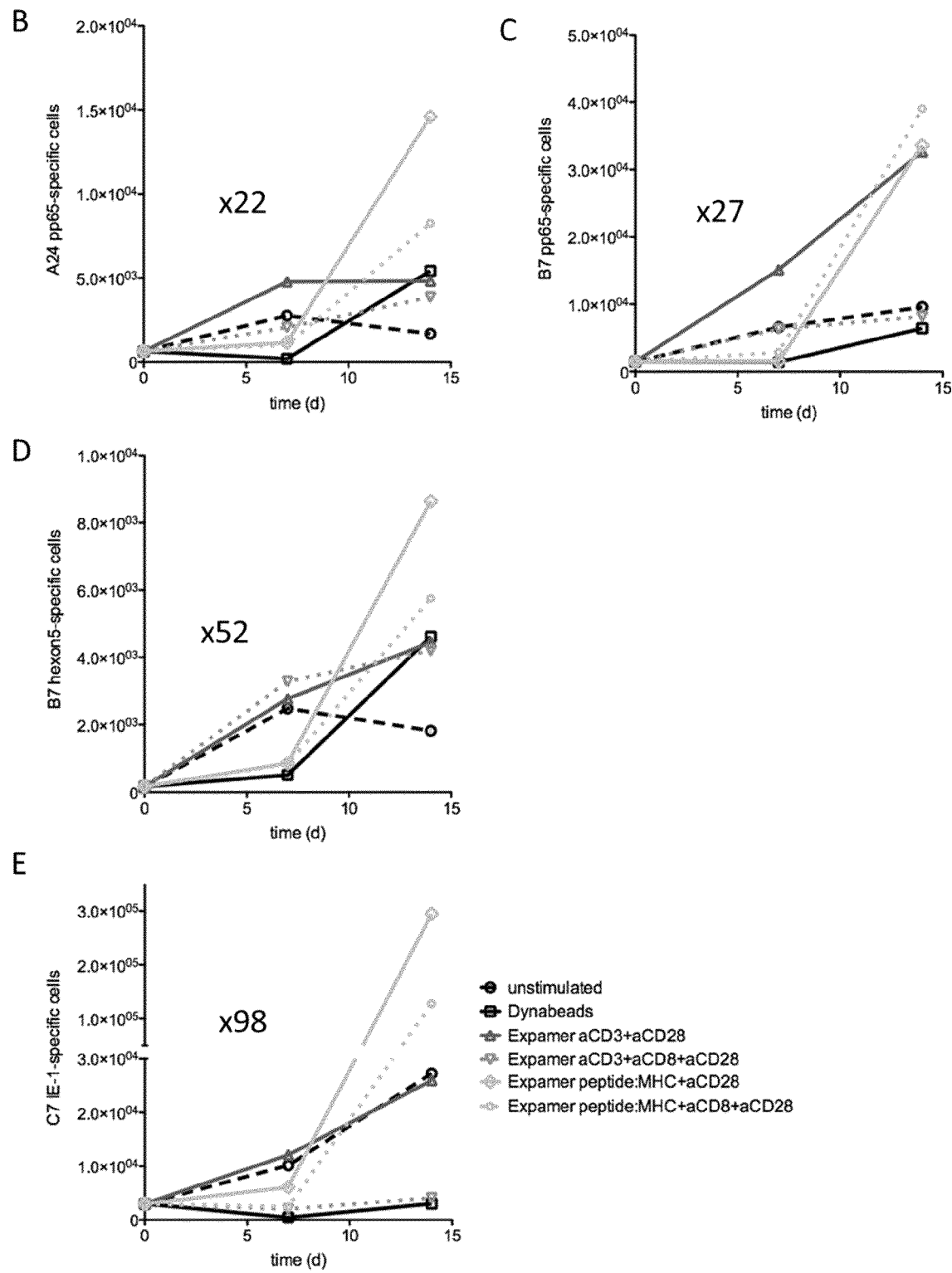
Figures 18, 18F:
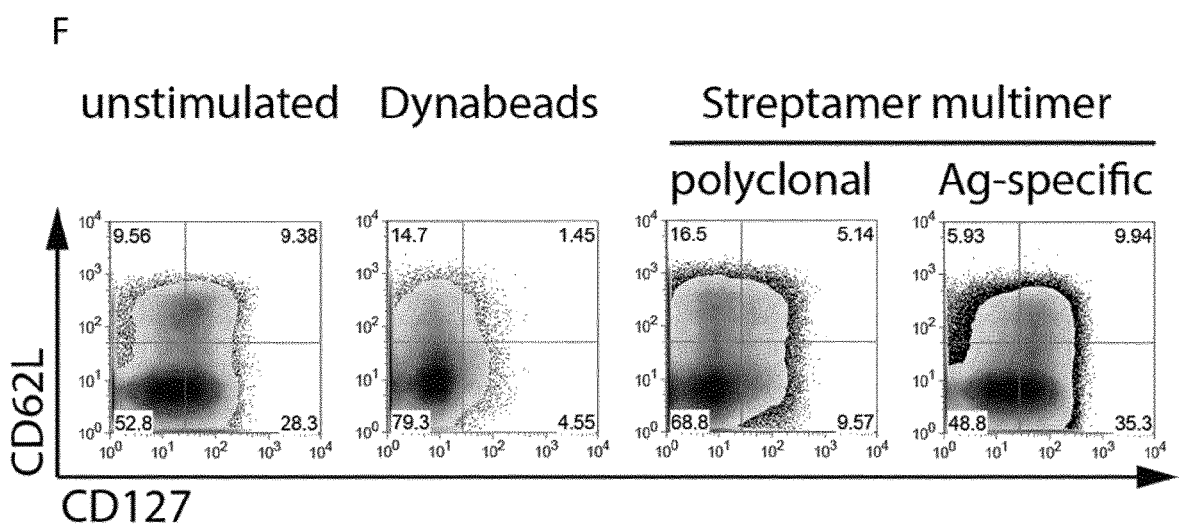

FIG. 18 shows the kinetics of selective antigen-specific (Ag-specific) expansion out of a bulk population of purified CD3+CD62L+CD45RA-Tcm responder cells that were stimulated in vitro with both a peptide:MHC molecule complex (that acts as first agent that provides a primary activation signal to the cells) and αCD28 Fab fragment (that acts as second agent that binds the accessory molecule on the surface of the cells) and unstimulated T cells (negative control) are shown. Both, the complex of antigen-specific peptide with the MHC molecule and the αCD28 Fab fragment were reversibly immobilized on the same soluble oligomeric streptavidin mutein (with n≥3) described in Example 5. The peptide used for the antigen-specific expansion in FIG. 18A was the peptide CRVLCCYVL (SEQ ID NO: 06), amino acids 309-317 of the immediate-early 1 protein restricted by the HLA-C702 MHC molecule (described in Ameres et al, PLOS Pathogens, May 2013, vol. 9, issue 5, e1003383) representing an HLA-C7/IE-1 epitope that is specific for cytomegalovirus (CMV). The MHC I molecule that presents the peptide carries at its C-terminus of the heavy chain the streptavidin binding peptide (SAWSHPQFEK(GGGS)$_2$GGSAWSHPQFEK (SEQ ID NO: 07), that is commercially available as "Twin-Strep-tag®" from IBA GmbH, Göttingen, Germany). FIG. 18A shows exemplary flow-cytometric analysis for the fraction of the Ag-specific cells that were proliferated using the peptide:MHC-I complex specific for this HLA-C7/IE-1 epitope as first agent that provides a primary activation signal to the cells reversibly immobilized on the soluble oligomeric streptavidin mutein. The graphs in FIG. 18B to FIG. 18E illustrates the expansion kinetics of further Ag-specificities according to the number of specific peptide: MHCI multimer-positive cells harvested per time point in analogy to FIG. 18A using distinct complexes of an antigen-specific peptide with the MHC I molecule as first agent that provides a primary activation signal to the cells reversibly immobilized on the soluble oligomeric streptavidin mutein. In more detail, FIG. 18B shows the expansion of Ag-specific cells that were expanded using the peptide:MHC-I complex specific for the pp65 epitope of CMV (amino acids 341-350 (QYDPVAALF, (SEQ ID NO: 08)) restricted by HLA-A2402), FIG. 18C shows the expansion of Ag-specific cells that were expanded using another peptide:MHC-I complex specific for the pp65 epitope of CMV (amino acids 265-274 RPHERNGFTV, (SEQ ID NO: 09)) restricted by HLA-B702), FIG. 18D shows the expansion of Ag-specific cells that were proliferated using the peptide:MHC-I complex specific for the hexon 5 epitope of adenovirus (amino acids 114-124 (CPYSGTAYNSL, (SEQ ID NO: 10)) restricted by HLA-B702), FIG. 18E shows the expansion of Ag-specific cells that were proliferated using the peptide:MHC-I complex specific for the HLA-B7/IE-1$_{309-317}$ epitope of CMV (exemplary FACS data see above FIG. 18A). All peptide:MHC molecules bearing the Twin Strep®-Tag are commercially available from IbaGmbH. In this context, the amino acid sequences of the HLA-A*2402, HLA-B*0702 and HLA-C*0702 molecules that carry the "Twin-Strep-tag®" as their C-terminus are shown as SEQ ID NO: 21, 22 and 23 in the accompanying Sequence Listings, while the amino acid sequence of the β$_2$ microglobulin (which forms together with the α chain, that means the HLA encoded molecules the respective MHC I molecule) is shown as SEQ ID NO: 24 in the accompanying Sequence Listing. In addition, FIG. 18F show exemplary flow-cytometric analysis of CD62L and CD127 surface expression after 14 days of culture for HLA-B7/Hexon5$_{114-124}$ stimulated/expanded cells from FIG. 18D.

Figure 19:
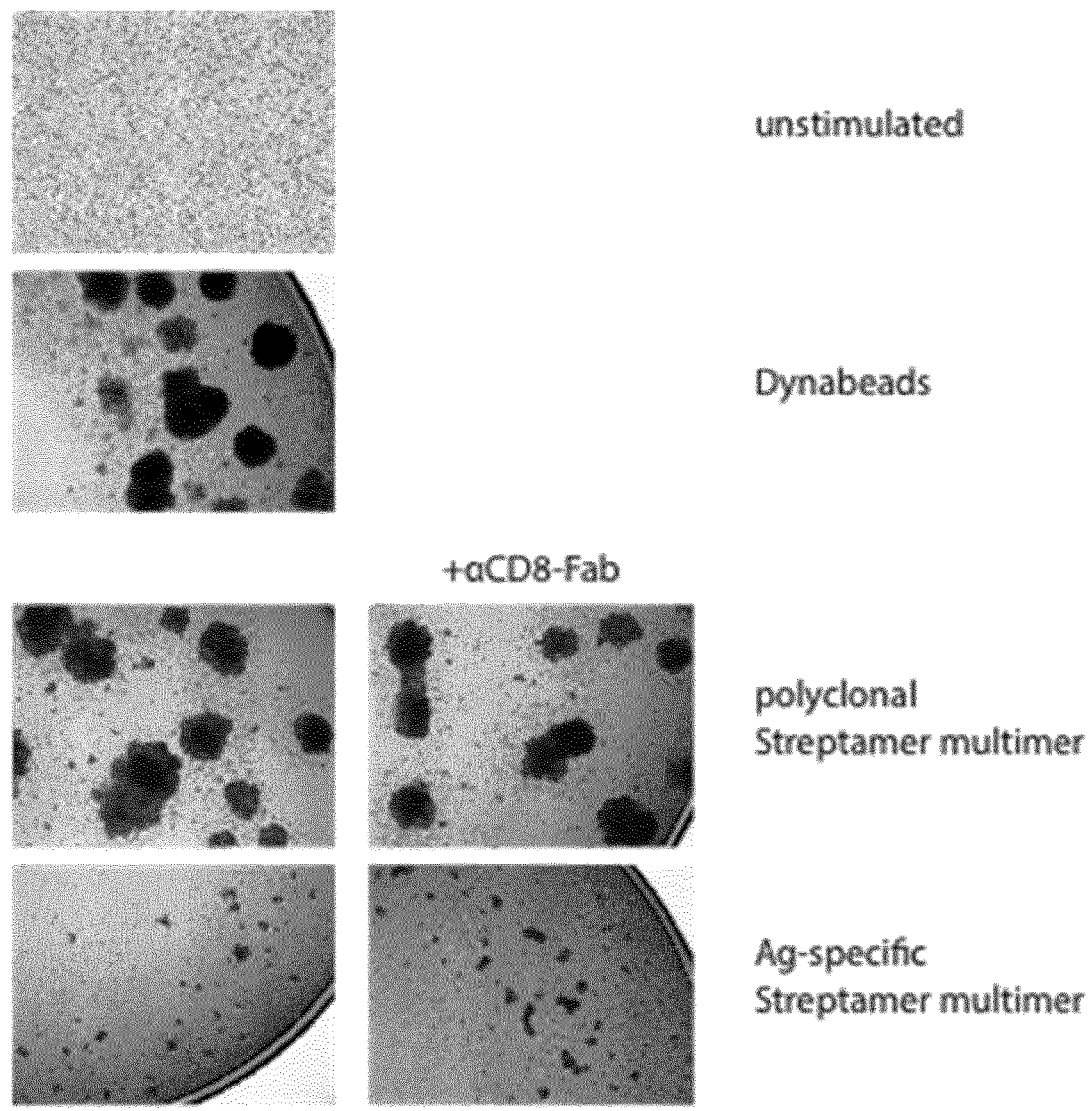

FIG. 19 shows the kinetics of selective Ag-specific expansion out of purified CD3+CD62L+CD45RA-Tcm responder cells that were stimulated in vitro with a) antigen specific peptide MHC I complexes and b) αCD28 Fab fragments that were reversibly immobilized as first and second agent on soluble oligomeric streptavidin muteins. For this purpose 500.000 CD3+CD62L+CD45RA-responder Tcm cells (Tresp) were stimulated Ag-specifically using 3 µl of a preparation of Streptactin multimerization reagent functionalized with 0.5 µg peptide:MHC class I complexes equipped with a streptavidin binding peptide (the specific peptide represents amino acids 114-124 (CPYSGTAYNSL, SEQ ID NO: 10) of the Hexon 5 protein of the adenovirus restricted by HLA-B0702, see above) and 0.5 µg αCD28 Fab. As an alternative, 4.5 µl of a preparation of Streptactin multimerization reagent loaded with 0.5 µg this peptide:MHC class I complex, 0.5 µg αCD8 Fab and 0.5 µg αCD28 Fab. For comparison, polyclonal stimulation was performed, using 3 µl of a preparation of Streptactin multimerization reagent (1 mg/ml) either loaded with a combination of 0.5 µg αCD3 Fab and 0.5 µg αCD28 Fab. Again as the alternative stimulation condition described above, 4.5 µl of a preparation of Streptactin multimers loaded with 0.5 µg αCD3 Fab, 0.5 µg αCD8 Fab and 0.5 µg αCD28 Fab was used. Untreated (unstimulated) Tresp cells served as negative control and Tresp cells stimulated polyclonal with Dynabeads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The photographs shown in FIG. 19 represent the degree of cluster formation on day 5 for Ag-specific stimulation as exemplified for the HLA-B7/Hexon 5 epitope of adenovirus.

Figure 20:
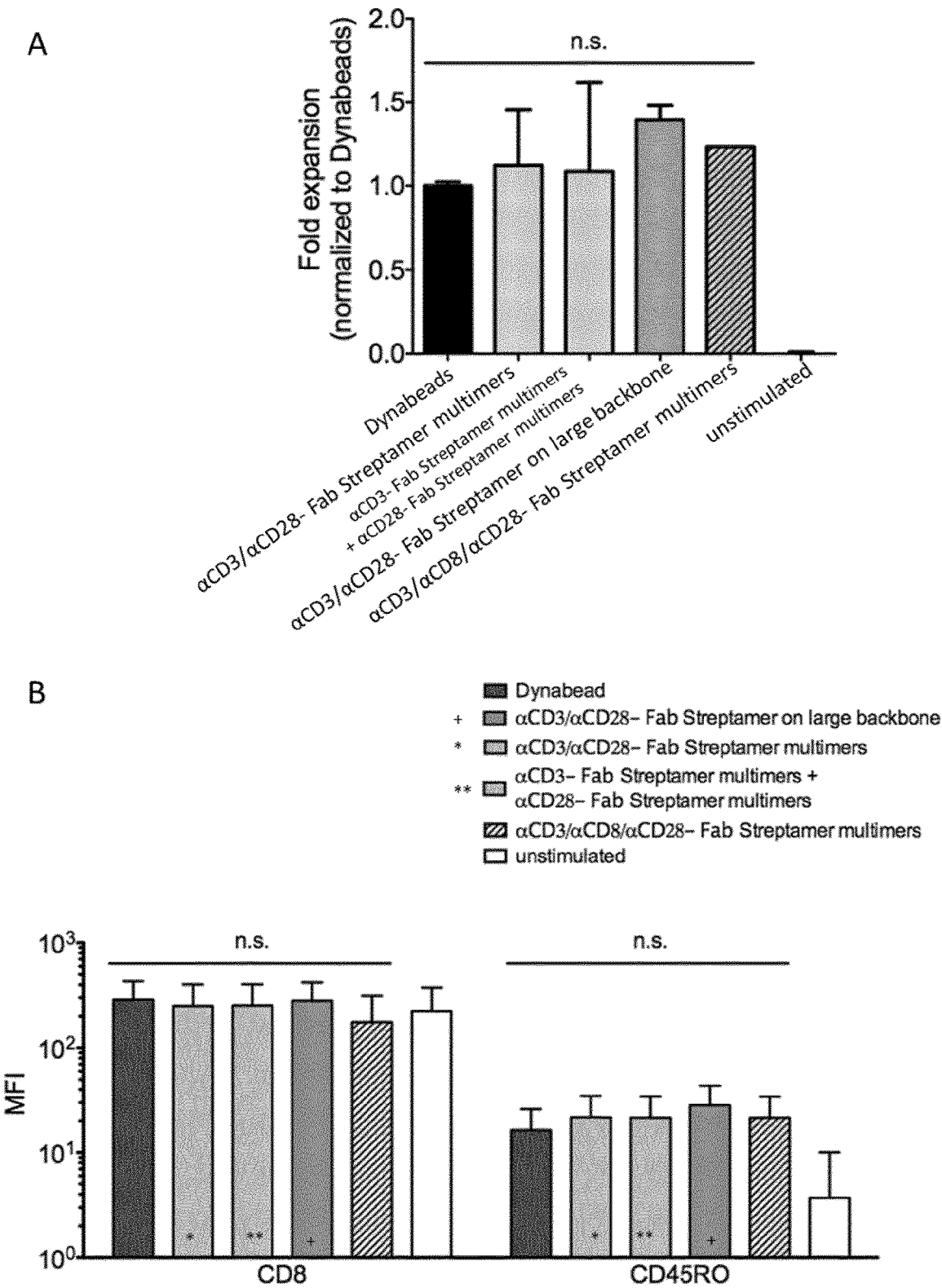

FIG. 20 shows the yield and phenotype of expansion of purified CD8+ T responder cells stimulated in vitro with αCD3/αCD28 Fab fragments that were reversibly immobilized on two kinds of soluble oligomeric Strep-tactin® acting a soluble multimerization reagent. The first kind of oligomeric Strep-tactin® was the fraction of the oligomeric streptavidin mutein (nmericobtained in Example 5 (conventional backbone), the second kind of this oligomeric streptavidin mutein used as soluble multimerization reagent was the soluble oligomer described above and referred herein as "large" Streptactin® backbone. In these experiments, the fraction of the oligomeric conventional streptavidin mutein (n≥3) was also used as a multimerization reagent that were either functionalized with single Fab fragments (third bar in FIG. 20A and FIG. 20B) or with a combination of αCD3 and αCD28 Fab-fragments. Furthermore to the combined stimulation with αCD3/αCD28 Fab fragments, also an additional αCD8 Fab fragment (commercially available from IBA GmbH, Göttingen, Germany) was immobilized in order to test whether it is possible to preferentially stimulate a specific T cell subpopulation. FIG. 20A shows a graph of bars that represent the degree of proliferation according to the number of cells harvested at day 6 compared to the negative controls (unstimulated purified CD8+ T responder cells) and normalized to the positive control (purified CD8+ T responder stimulated with commercially available Dynabeads (beads on which αCD3 and αCD28 monoclonal antibodies are irreversible immobilized). FIG. 20B shows flow-cytometric analysis of the surface expression of CD8 and the T cell surface molecule CD45RO (that is indicative of T cell proliferation and activation) after cell culture. The various stimulating conditions were compared using one-way ANOVA and no significant difference (n.s.) was detected.

FIG. 21 shows the yield and phenotype for the expansion of purified CD8+ T responder cells stimulated in vitro with αCD3/αCD28 Fab fragments that were reversibly immobilized on soluble oligomeric Strep-tactin® acting as a soluble multimerization reagent that were either functionalized with single Fab fragments or with a combination of Fab-fragments (as already described above). In these experiments, the CD8+ T responder cells were stimulated with the soluble multimerization reagent (the soluble oligomeric Strep-tactin® (1 mg/ml) of Example 5) which was functionalized with varying amounts of αCD3 and αCD28 Fab fragments, optionally together with the αCD8 Fab fragment described above. The term "1×" corresponds to 1.5 µg multimerized Streptactin functionalized with 0.5 µg αCD3 Fab fragment alone and 1.5 µg multimerized Streptactin functionalized with 0.5 µg αCD28 Fab alone), or 3 µl of a preparation of oligomeric Streptactin loaded with 0.5 µg αCD3 Fab fragment and 0.5 µg αCD28 Fab, or 4.5 µl of a preparation of Streptactin multimers loaded with 0.5 µg strep-tagged αCD3, 0.5 µg strep-tagged αCD8 and 0.5 µg strep-tagged αCD28 Fab. Accordingly, the term "2×" corresponds to 3.0 µg multimerized Streptactin functionalized with 1 µg αCD3 Fab fragment alone and 3.0 µg multimerized Streptactin functionalized with 1 µg αCD28 Fab alone, meaning that twice the amount of immobilized αCD3 Fab fragment was used. Untreated Tresp cells served as negative control and purified CD8+ T responder stimulated with commercially available Dynabeads (beads on which αCD3 and αCD28 monoclonal antibodies are irreversible immobilized) as positive control. FIG. 21A shows a graphs in which the bars represent the degree of proliferation according to the number of cells harvested at day 5 compared to the negative controls and normalized to the positive control. FIG. 21B shows FACS analysis of CD8 and CD45RO surface expression after cell culture.

Figure 22:
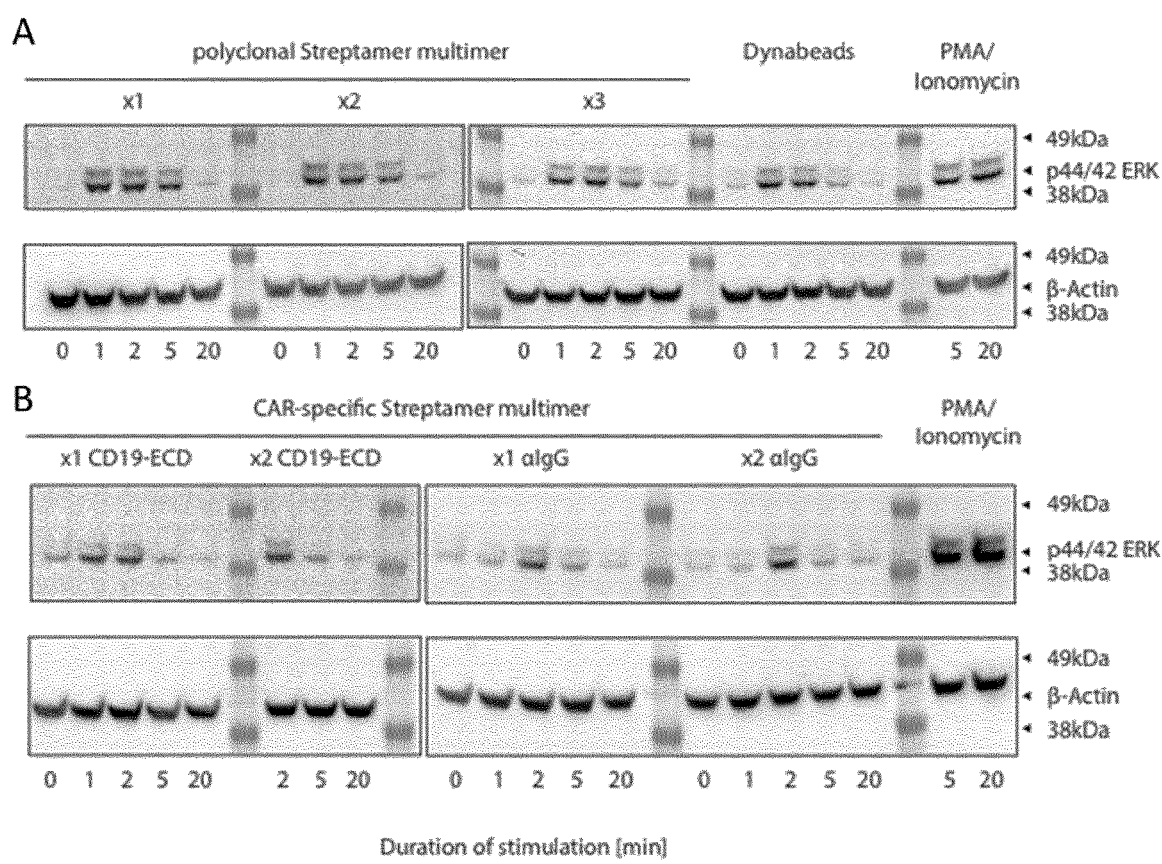

FIG. 22 shows the activation of intracellular signaling cascades of transduced Jurkat cells that have been modified to express an αCD19 chimeric antigen receptor (CAR), and that were stimulated using the oligomeric Strep-tactin® of Example 5 as soluble multimerization reagent. The specificity of a CAR is typically derived from a scFv region assembled from the antigen-binding region of a monoclonal antibody (mAb) that specifically binds a target/tumor associated antigen such as CD19 and links it to T cell specific signaling (described in Hudecek et al, Clin Cancer Res. 2013 Jun. 15; 19(12): 3153-3164. In the experiments the extracellular domain (ECD) of CD19, which contains the natural ligand of the αCD19 CAR as well as the polyclonal αIgG F(ab)$_2$ fragment that recognizes the IgG4 spacer (donkey-anti-human F(ab)$_2$ is commercially available from Jackson Immuno Research) within the αCD19-CAR were also used in this experiment as first agent that provides a primary activation signal to the jurkat cells. The reversibly immobilization to the soluble oligomeric streptavidin mutein was provided by the streptavidin peptide SAWSHPQFEK (GGGS)$_2$GGSAWSHPQFEK (SEQ ID NO: 07) that was fused to the C-terminus of the ECD of CD19 or by the biotinylated (Fab)$_2$ fragment of the αIgG (since the streptavidin mutein "m2" binds biotin with reduced affinity, this binding is reversible and can for example be displaced by addition of an excess of free biotin). In the control experiment of FIG. 22A 300.000 CD3+ Jurkat responder cells (Jresp) were stimulated with varying amounts of a mixture of preparations of oligomeric Streptactin (1 mg/ml) that was functionalized with the αCD3 Fab and the αCD28 Fab ("×1" corresponds to 3 µg multimerized Streptactin functionalized with 0.5 µg αCD3- and 0.5 µg aCD28 Fab-polyclonal Streptamer multimer). In the experiment of FIG. 22B 3 µl of a preparation of the oligomeric Streptactin was functionalized with 0.5 µg (×1) or 1 µg (×2) of the extracellular domain (ECD) of CD19 or with 3 µl of a preparation of the oligomeric Streptactin loaded with 0.5 µg (×1) or 1 µg (×2) αIgG that recognizes the IgG4 spacer (which are both CAR-specific Streptamer® multimers). Jresp stimulated with Dynabeads (beads on which αCD3 and αCD28 monoclonal antibodies are irreversible immobilized) or PMA and ionomycin served as positive controls. Jresp cells were seeded in 1.5 ml Eppendorf tubes in 200 µl cell culture medium supplemented with 30 U/ml IL-2. Cells were incubated at 37° C. and put on ice and lysed after 0 min to 20 min of stimulation.

FIG. 23 shows the expansion of purified CD3$^+$ T responder cells stimulated in vitro with αCD3/αCD28 Fab fragments that were reversibly immobilized on the soluble oligomeric Strep-tactin® of Example 5 that served a soluble multimerization reagent. In one experiment, in addition to αCD3/αCD28 Fab fragments, also an αCD8 Fab fragment commercially available from IBA GmbH, Göttingen, Germany (catalogue number 6-8000-203) was immobilized on the soluble oligomer of the streptavidin mutein in order to test whether it is possible to preferentially stimulate in vitro the CD8$^+$ T cell subpopulation within the bulk CD3$^+$ culture with a multimerization reagent of the invention having reversibly immobilized thereon also an αCD8 Fab fragment. In more detail, 500.000 purified CD3$^+$ responder T cells (Tresp) were stimulated with 3 µl of a preparation of oligomeric Streptavidin (1 mg/ml) loaded with a combination of 0.5 µg of the αCD3 and 0.5 µg of the αCD28 Fab. As an alternative approach, 4.5 µl of the Streptactin oligomer were loaded with 0.5 µg αCD3, 0.5 µg αCD8 Fab and 0.5 µg αCD28 Fab described above. Unstimulated Tresp cells served as negative control and Tresp stimulated with Dynabeads (beads on which αCD3 and αCD28 monoclonal antibodies are irreversible immobilized) served as positive control.

Figure 24:
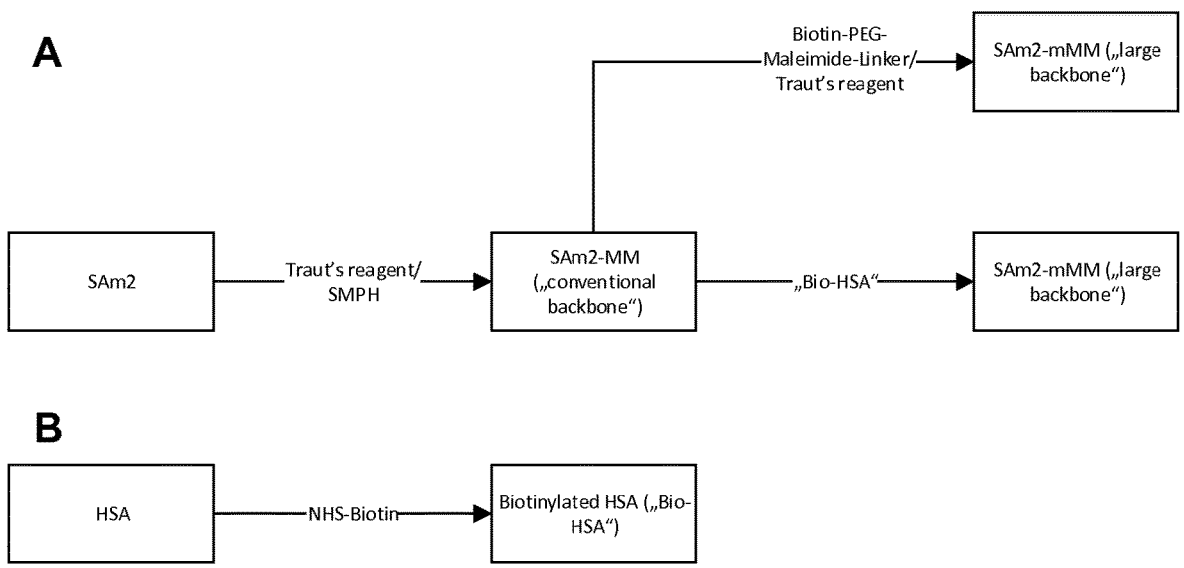

FIG. 24 depicts exemplary strategies for the generation of oligomeric streptavidin muteins that can be used as soluble multimerization reagent of the invention. FIG. 24A shows that in a first step, the streptavidin mutein "m2" (SAm2) that comprises the amino acid sequence Ile$^{44}$-Gly$^{45}$-Ala$^{46}$-Arg$^{47}$ (SEQ ID NO: 03) at sequence positions 44 to 47 of wild type streptavidin is used for generation of oligomeric streptavidin muteins having a "conventional backbone". In a second step, oligomeric soluble streptavidin muteins having a "large backbone" can be generated by either by coupling of streptavidin mutein with biotinylated carrier protein such as human serum albumin (HSA) or by coupling the streptavidin muteins with synthetic carriers such as PEG. FIG. 24B: Biotinylation of human serum albumin (HSA).

DETAILED DESCRIPTION OF THE INVENTION

The present invention provides methods, kits and an apparatus for expanding a population of cells or for inducing a population of T cells to proliferate.

The term "population of cells" as used herein encompasses all cells which can be expanded by binding to a cell surface receptor a first agent that provides a primary activation signal to the cells. It is also possible that for expansion of the population of cells, binding of second agent to a second cell surface receptor (accessory molecule) might be needed to produce a co-stimulatory signal required for expansion of the cells. In some embodiments the cell population may be a population of lymphocytes including, but not limited a population of B cells, a population of T cells or a population of natural killer cells. Illustrative examples of cell populations are B cells carrying CD40 or CD137 (both cell population can be proliferated upon binding of only a first agent that provides an activation signal, for example 4-1BB ligand; or an αCD40 antibody molecule or an αCD137 antibody molecule (see for example Zhang et al., 2010, J Immunol, 184:787-795)). Other illustrative examples for agents (either first or second) that may be used for the expansion of B cells are agents that bind to IgG, CD19, CD28 or CD14, for example αCD19, αIgG, αCD28, or αCD14 antibody molecules. It is also envisioned that first or second agents for the expansion of B cell may comprise ligands for toll like receptors or interleukins, such as IL-21 (see for example Dienz O, et al. 2009. J. Exp. Med. 206:69). It is noted that lipopolysaccharide dependent activation of B cells is also encompassed in the present invention, as a lipopolysaccharide can also be used as first agent and can be equipped with a binding partner C1 as used herein. Other illustrative examples of suitable cell populations include T cell population that expand after being activated by binding of a first agent to TCR/CD3 and binding of a second agent to an accessory molecule on the T cell such as CD28. In this case, the first agent stimulates a TCR/CD3 complex-associated signal in the T cells and the second agent provides a secondary stimulus by binding CD28 as accessory molecule. Agents that can be used for the expansion of T cells may also include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T-cells are CD62L$^+$CD8$^+$ specific central memory T cells) or regulatory T cells (an illustrative example of Treg are CD4$^+$CD25$^+$CD45RA+ Treg cells). The term "T cell (population)" as used herein also includes T cells that comprise a chimeric antigen receptor (CAR) that is also known as artificial T cell receptors or chimeric T cell receptors. Thus, a T cell population that comprises a chimeric antigen receptor can also be expanded using the methods, reagents and devices of the present invention. See in this respect also Example 15 in which Jurkat cells that express a chimeric CD19 specific antigen receptor (CAR) were stimulated using a soluble multimerization reagent of the present invention. Another illustrative example of a suitable cell population includes natural killer cells (NK cells), which may for example be expanded with agents that bind to CD16 or CD56, such as for example αCD16 or αCD56 antibodies. In illustrative example for such an αCD16 antibody is the antibody 3G8 with a VH sequence set forth in SEQ ID NO: 25 and a VL sequence set forth in SEQ ID NO: 26 (see for example Hoshino et al, Blood. 1991 Dec. 15; 78(12):3232-40.). Another agent that may be used for expansion of NK cells may be IL-15 (see for example Vitale et al. 2002. The Anatomical Record. 266:87-92). Yet another illustrative example of a suitable cell population includes monocytes, which may for instance be expanded using an agent that binds to CD14, such as an αCD14 antibody molecule. The cell population can be of any mammalian origin, including but not limited to human, rabbit, guinea pig, squirrel, hamster, cat, dog, lemur, goat, pig, horse, rhesus monkey, macaque, or a chimpanzee.

Thus, in line with the above, this invention pertains to methods for selectively inducing ex vivo expansion of a population of cells such as B cells, T cells or natural killer cells in the absence of exogenous growth factors, such as lymphokines, and accessory cells. In addition, the proliferation of these cells such as B cells or T cells can be induced without the need for antigen, thus providing an expanded cell population such as a T cell population which is polyclonal with respect to antigen reactivity. The methods disclosed herein may provide for sustained proliferation of a selected population of T cells such as CD4+ or CD8+ T cells over an extended period of time to yield a multi-fold increase in the number of these cells relative to the original T cell population. In general, in case of a (clonal) expansion of a lymphocyte population as described herein, all progeny may share the same antigen specificity as the cell population that was selected for expansion.

Also in line with the above, provided by this invention are methods for expanding a population of antigen specific T cells. To produce a population of antigen specific T cells, T cells are contacted with an antigen in a form suitable to trigger a primary activation signal in the T cell, i.e., the antigen is presented to the T cell such that a signal is triggered in the T cell through the TCR/CD3 complex. For example, the antigen can be presented to the T cell by an antigen presenting cell in conjunction with an MHC molecule. An antigen presenting cell, such as a B cell, macrophage, monocyte, dendritic cell, Langerhans cell, or other cell which can present antigen to a T cell, can be incubated with the T cell in the presence of the antigen (e.g., a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, e.g., a virus, which presents antigens of the pathogen can be incubated with a T cell. Following antigen specific activation of a population of T cells, the cells can be expanded in accordance with the methods of the invention. For example, after antigen specificity has been established, T cells can be expanded by culture with an anti-CD3 antibody (used as first agent) and an anti-CD28 antibody (used as second agent) according to the methods described herein. In another embodiment, the first agent can be an MHC I: peptide complex, which binds to an antigen specific T cell population. In such an embodiment, any antigen specific peptide that is known and that can be complexed with the respective MHC I molecule can be used. See in this respect Examples 11 and 12 in which selective Antigen-specific expansion of Tcm responder cells out of bulk CD3+ central memory T cells was exemplified for four different antigen-specific cells. Alternatively, it is also possible to use as first agent the natural ligand of a receptor that triggers of cell expansion. See in this respect Example 15 in which the extracellular domain of CD19 caused the activation of intracellular signaling cascades of transduced Jurkat cells that were modified to express chimeric CD19 binding antigen receptor (CAR).

The sample of the cell population can be from any suitable source, typically all sample of a body tissue or a body fluid such as blood. In the latter case, the sample might for example, be a population of peripheral blood mononucleated cells (PBMC) that can be obtained by standard isolation methods such a ficoll gradient of blood cells. The cell population to be expanded can however also be in purified form and might have been isolated using an reversible cell staining/isolation technology as described patent in U.S. Pat. Nos. 7,776,562, 8,298,782, International Patent application WO02/054065 or International Patent Application WO2013/011011. Alternatively, the population of cells can also be obtained by cell sorting via negative magnetic immunoadherence as described in U.S. Pat. No. 6,352,694 B1 or European Patent EP 0 700 430 B1. If an isolation method described here is used in basic research, the sample might be cells of in vitro cell culture experiments. The sample will typically have been prepared in form of a fluid, such as a solution or dispersion.

In line with the above, in one embodiment the invention provides an in vitro-method of expanding a population of cells, comprising contacting a sample comprising a population of cells with a multimerization reagent. The multimerization reagent has reversibly immobilized thereon (bound thereto) a first agent that provides a primary activation signal to the cells, wherein the multimerisation reagent comprising at least one binding site Z1 for the reversible binding of the first agent. The first agent comprises at least one binding partner C1, wherein the binding partner C1 is able of reversibly binding to the binding site Z1 of the multimerization reagent, wherein the first agent is bound to the multimerization reagent via the reversible bond formed between the binding partner C1 and the binding site Z1. The first agent binds to a receptor molecule on the surface of the cells, thereby providing a primary activation signal to the cells and thereby activating the cells.

In another embodiment, the invention provides a method, wherein the multimerization agent has reversibly immobilized thereon (bound thereto) a second agent that stimulates an accessory molecule on the surface of the cells. The second agent comprises a binding partner C2, wherein the binding partner C2 is able of being reversibly bound to a binding site Z2 of the multimerization reagent, wherein the second agent is bound to the multimerization reagent via the reversible bond formed between the binding partner C2 and the binding site Z2. The second agent binds to the accessory molecule on the surface on the surface of the cells, thereby stimulating the activated cells. In this embodiment the first agent may stimulate a TCR/CD3 complex-associated signal in the T cells and may be a binding agent that specifically binds CD3. In this embodiment the accessory molecule on the T cell may be CD28 and the second agent that binds the accessory molecule is a binding reagent that specifically binds CD28. In this case, the first agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. Also the second agent that specifically binds CD28 may be selected from the group consisting of an anti-CD28-antibody, a divalent antibody fragment of an anti-CD28 antibody, a monovalent antibody fragment of an anti-CD28-antibody, and a proteinaceous CD28 binding molecule with antibody-like binding properties. The divalent antibody fragment may be an (Fab)$_2$'-fragment, or a divalent single-chain Fv fragment while the monovalent antibody fragment may be selected from the group consisting of a Fab fragment, a Fv fragment, and a single-chain Fv fragment (scFv). A proteinaceous CD3 or CD28 binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In general the first and the second agent that is used in the present invention may, for instance be, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). In some embodiments one or more binding sites of the first or second agent may be a bivalent proteinaceous artificial binding molecule such as a dimeric lipocalin mutein that is also known as "duocalin". In some embodiments the receptor binding reagent may have a single second binding site, i.e., it may be monovalent. Examples of monovalent first or second agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

As mentioned above, an example of a proteinaceous binding molecule with antibody-like functions is a mutein based on a polypeptide of the lipocalin family (see for example, WO 03/029462, Beste et al., *Proc. Natl. Acad. Sci. U.S.A.* (1999) 96, 1898-1903). Lipocalins, such as the bilin binding protein, the human neutrophil gelatinase-associated lipocalin, human Apolipoprotein D or human tear lipocalin possess natural ligand-binding sites that can be modified so that they bind a given target. Further examples of a proteinaceous binding molecule with antibody-like binding properties that can be used as a receptor binding reagent that specifically binds to the receptor molecule include, but are not limited to, the so-called glubodies (see e.g. international patent application WO 96/23879), proteins based on the ankyrin scaffold (Mosavi, L. K., et al., *Protein Science* (2004) 13, 6, 1435-1448) or crystalline scaffold (e.g. international patent application WO 01/04144) the proteins described in Skerra, *J. Mol. Recognit.* (2000) 13, 167-187, AdNectins, tetranectins and avimers. Avimers, including multivalent avimer proteins evolved by exon shuffling of a family of human receptor domains, contain so called A-domains that occur as strings of multiple domains in several cell surface receptors (Silverman, J., et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Yet further examples of suitable proteinaceous binding molecules are an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994) 13, 5303-5309), a diabody (cf. Holliger et al., PNAS USA (1993)90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

Turning now the multimerization reagent, the binding sites Z1 and Z2 of the multimerization agent can be identical (see also the Example of FIG. 3). In this case, a single multimerization agent may be used.

In the embodiment that a reversibly bond first and, optionally second agent is used, the multimerization reagent may be immobilized on a solid surface. Any solid surface (support) can be used for the immobilization of the multimerization reagent. Illustrative examples of solid surfaces on which the multimerization reagent can be immobilized include a magnetic bead, a polymeric bead, a cell culture plate, a microtiter plate, a membrane, or a hollow fiber. Hollow fibers are, for example, used as bioreactor in the Quantum® Cell Expansion System, available from TerumoBCT Inc. (Lakewood, Colo., USA). The multimerization reagent is usually covalently attached to the solid support, however, non-covalent interactions can also be used for immobilization, for example on plastic substrates, if wanted.

As also explained in more detail below, the multimerization reagent can, for example, be a streptavidin or avidin mutein that reversibly binds a streptavidin binding peptide. Such streptavidin muteins can be covalently attached to any surface, for example, resin (beads) used for chromatography purification and are commercially available in such form from IBA GmbH, Göttingen, for example, as Strep-Tactin® Sepharose, Strep-Tactin® Superflow®, Strep-Tactin® Superflow® high capacity or Strep-Tactin® MacroPrep®. Other illustrative examples multimerization reagents that are readily commercially available are immobilized metal affinity chromatography (IMAC) resins such as the TALON® resins (Westburg, Leusden, The Netherlands) that can be used for the reversible immobilization of oligo-histidine tagged (his-tagged) proteins in general, meaning here, for the reversible binding of a first or a second agent that carries as first binding partner C1 or second binding partner C2 an oligohistidine tag such as an penta- or hexa-histidine tag. Other examples of multimerzation reagents are calmodulin sepharose available from GE Life Sciences which can be used together with a first or second agent that comprises a calmodulin binding peptide as binding partner C1 or C2 or sepharose, to which glutathion is coupled. In the case, the binding partner C1 or C2 is glutathion-S-transferase.

In other embodiments of the method of the invention the multimerization reagent can be in a soluble form. In principle, the same multimerization agents can be used as in the case of a multimerization reagent that is immobilized on a solid support. The multimerization reagent is soluble form, can for example, be a streptavidin mutein oligomer, a calmodulin oligomer, a compound (oligomer) that provides least two chelating groups K, wherein the at least two chelating groups are capable of binding to a transition metal ion, thereby rendering moiety A capable of binding to an oligohistidine affinity tag, multimeric glutathione-S-transferase, or a biotinylated carrier protein.

As explained above, the first and second agent has, in addition to the binding site that is able to bind the respective cell surface receptor molecule, a binding partner C1 or C2 (which will be referred to as "binding partner C" in the following for the ease of reference).

This binding partner C is able to bind to a binding site Z of the multimerization reagent (Z means either binding site Z1 or binding site Z2 of the multimerization reagent) C. The non-covalent bond that is formed between the binding partner C that is included in the first or second agent and the binding site(s) Z of the multimerization reagent may be of any desired strength and affinity, as long as it is disruptable or reversible under the conditions under which the method of the invention is performed. The dissociation constant ($K_D$) of the binding between the binding partner C that is included in the receptor binding reagent and the binding site Z of the multimerization reagent may have a value in the range from about $10^{-2}$ M to about $10^{-13}$ M. Thus, this reversible bond can, for example, have a $K_D$ from about $10^{-2}$ M to about $10^{-13}$ M, or from about $10^{-3}$ M to about $10^{-12}$ M or from about $10^{-4}$ M to about $10^{-11}$ M, or from about $10^{-5}$ M to about $10^{-10}$ M. The $K_D$ of this bond as well as the $K_D$, $k_{off}$ and $k_{on}$ rate of the bond formed between the binding site B of the receptor binding reagent and the receptor molecule can be determined by any suitable means, for example, by fluorescence titration, equilibrium dialysis or surface plasmon resonance. The receptor molecule binding reagent may include at least one, including two, three or more, second binding partners C and the affinity reagent may include at least two, such as three, four, five, six, seven, eight or more binding sites for the binding partner that is included in the receptor molecule binding reagent. As described in U.S. Pat. Nos. 7,776,562, 8,298,782 or International Patent application WO 2002/054065 any combination of a binding partner C and an affinity agent with one or more corresponding binding sites Z can be chosen, as long as the binding partner C and the binding site Z of the affinity agent are able to reversibly bind or multimerize in a (multivalent) complex, which typically goes along with an avidity effect.

The binding partner included in the first or second agent may be an oligopeptide, a polypeptide, a protein, a nucleic acid, a lipid, a saccharide, an oligosaccharide, or a polysaccharide. Such a binding partner has a higher affinity to the binding site of the multimerization reagent than to other matter. Examples of a respective binding partner include, but are not limited to, an immunoglobulin molecule, a fragment thereof and a proteinaceous binding molecule with antibody-like functions.

In some embodiments the binding partner C that is included in the first or second agent includes biotin and the affinity reagent includes a streptavidin analogue or an avidin analogue that reversibly binds to biotin.

In some embodiments the binding partner C that is included in the first or second agent includes a biotin analogue that reversibly binds to streptavidin or avidin, and the affinity reagent includes streptavidin, avidin, a streptavidin analogue or an avidin analogue that reversibly binds to the respective biotin analogue.

In some further embodiments the binding partner C that is included in the first or second agent includes a streptavidin or avidin binding peptide and the affinity reagent includes streptavidin, avidin, a streptavidin analogue or an avidin analogue that reversibly binds to the respective streptavidin or avidin binding peptide.

In some embodiments the binding partner that is included in the first or second agent may include a streptavidin-binding peptide Trp-Ser-His-Pro-Gln-Phe-Glu-Lys (SEQ ID NO: 01) and the affinity reagent may include a streptavidin mutein (analogue) that comprise the amino acid sequence $Val^{44}$-$Thr^{45}$-$Ala^{46}$-$Arg^{47}$ (SEQ ID NO: 02) at sequence positions 44 to 47 of wild type streptavidin or the streptavidin mutein (analogue) that comprises the amino acid sequence $Ile^{44}$-Gly45-$Ala^{46}$-$Arg^{47}$ (SEQ ID NO: 03) at sequence positons 44 to 47 of wild type streptavidin, both of which are described in U.S. Pat. No. 6,103,493, for example, and are commercially available under the trademark Strep-Tactin®. The streptavidin binding peptides might, for example, be single peptides such as the "Strep-tag®" described in U.S. Pat. No. 5,506,121, for example, or streptavidin binding peptides having a sequential arrangement of two or more individual binding modules as described in International Patent Publication WO 02/077018 or U.S. Pat. No. 7,981,632.

In some embodiment the binding partner C of the first or second agent includes a moiety known to the skilled artisan as an affinity tag. In such an embodiment the affinity reagent includes a corresponding binding partner, for example, an antibody or an antibody fragment, known to bind to the affinity tag. As a few illustrative examples of known affinity tags, the binding partner that is included in the first or second agent may include an oligohistidine, an immunoglobulin domain, maltose-binding protein, glutathione-S-transferase (GST), chitin binding protein (CBP) or thioredoxin, calmodulin binding peptide (CBP), FLAG'-peptide, the HA-tag (sequence: Tyr-Pro-Tyr-Asp-Val-Pro-Asp-Tyr-Ala, (SEQ ID NO: 11)), the VSV-G-tag (sequence: Tyr-Thr-Asp-Ile-Glu-Met-Asn-Arg-Leu-Gly-Lys, (SEQ ID NO: 12)), the HSV-tag (sequence: Gln-Pro-Glu-Leu-Ala-Pro-Glu-Asp-Pro-Glu- Asp, (SEQ ID NO: 13)), the T7 epitope (Ala-Ser-Met-Thr-Gly-Gly-Gln-Gln-Met-Gly, (SEQ ID NO: 14)), maltose binding protein (MBP), the HSV epitope of the sequence Gln-Pro-Glu-Leu-Ala-Pro-Glu-Asp-Pro-Glu-Asp (SEQ ID NO: 13) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 15), the V5-tag (sequence: Gly-Lys-Pro-Ile-Pro-Asn-Pro-Leu-Leu-Gly-Leu-Asp-Ser-Thr, SEQ ID NO: 16), or glutathione-S-transferase (GST). In such an embodiment the complex formed between the one or more binding sites of the multimerisation reagent, in this case an antibody or antibody fragment, and the antigen can be disrupted competitively by adding the free antigen, i.e. the free peptide (epitope tag) or the free protein (such as MBP or CBP). The affinity tag might also be an oligonucleotide tag. Such an oligonucleotide tag may, for instance, be used to hybridize to an oligonucleotide with a complementary sequence, linked to or included in the affinity reagent.

In some embodiments the binding between the binding partner C that is included in the first or second agent and one or more binding sites of the multimerization reagent occurs in the presence of a divalent, a trivalent or a tetravalent cation. In this regard in some embodiments the multimerization reagent includes a divalent, a trivalent or a tetravalent cation, typically held, e.g. complexed, by means of a suitable chelator. The binding partner that is included in the receptor binding reagent may in such an embodiment include a moiety that includes, e.g. complexes, a divalent, a trivalent or a tetravalent cation. Examples of a respective metal chelator, include, but are not limited to, ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), or 1,2-bis(o-aminophenoxy)ethane-N,N,N',N'-tetraacetic acid (BAPTA). As an example, EDTA forms a complex with most monovalent, divalent, trivalent and tetravalent metal ions, such as e.g. calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments the binding partner C that is included in the first or second agent includes a calmodulin binding peptide and the affinity reagent includes multimeric calmodulin as described in U.S. Pat. No. 5,985,658 or as described herein with reference to FIG. 2, for example. In some embodiments the binding partner C that is included in the first or second agent includes a FLAG peptide and the affinity reagent includes an antibody that binds to the FLAG peptide, e.g. the FLAG peptide, which binds to the monoclonal antibody 4E11 as described in U.S. Pat. No. 4,851, 341. In one embodiment the binding partner C that is included in the first or second agent includes an oligohistidine tag and the affinity reagent includes an antibody or a transition metal ion binding the oligohistidine tag. The disruption of all these binding complexes may be accomplished by metal ion chelation, e.g. calcium chelation, for instance by adding EDTA or EGTA (supra). Calmodulin, antibodies such as 4E11 or chelated metal ions or free chelators may be multimerized by conventional methods, e.g. by biotinylation and complexation with streptavidin or avidin or multimers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In such embodiments the binding between the binding partner C that is included in the first or second agent and the one or more binding sites Z of the multimerization reagent can be disrupted by metal ion chelation. The metal chelation may, for example, be accomplished by addition of EGTA or EDTA.

In some embodiments, in particular, if the multimerization reagent is in soluble form and is based on streptavidin or avidin, it is an oligomer or a polymer of streptavidin or avidin or of any mutein (analogue) of streptavidin or avidin. The binding site Z is the natural biotin binding of avidin or streptavidin. The respective oligomer or polymer may be crosslinked by a polysaccharide. In one embodiment oligomers or polymers of streptavidin or of avidin or of muteins (analogs) of streptavidin or of avidin are prepared by the introduction of carboxyl residues into a polysaccharide, e. g. dextran, essentially as described in Noguchi, A, et al., Bioconjugate Chemistry (1992) 3,132-137 in a first step. Then streptavidin or avidin or analogues thereof may be linked via primary amino groups of internal lysine residue and/or the free N-terminus to the carboxyl groups in the dextran backbone using conventional carbodiimide chemistry in a second step. In addition, cross-linked oligomers or polymers of streptavidin or avidin or of any mutein (analogue) of streptavidin or avidin may also be obtained by crosslinking individual streptavidin or avidin molecules (the tetrameric homodimer of streptavidin or avidin is referred herein as an "individual molecule" or smallest building block of a respective oligomer or polymer) via bifunctional molecules, serving as a linker, such as glutardialdehyde or by other methods described in the art. It is, for example, possible to generate oligomers of streptavidin muteins by introducing, in a first step, thiol groups into the streptavidin mutein (this can, for example, be done by reaction the streptavidin mutein 2-iminothiolan (Trauts reagent) and by activating, in a separate reaction amino groups available in the streptavidin mutein. This activation of amino groups can be achieved by reaction of the streptavidin mutein with a commercially available heterobifunctional crosslinkers such as sulfo succinimidyl 4-(N-maleimidomethyl)cyclo hexane-1-carboxylate (sulfo SMCC) or Succinimidyl-6-[(β-maleimidopropionamido)hexanoate (SMPH). In a second step, the two reaction products so obtained are mixed together, leading to the reaction of the thiol groups contained in the one batch of modified streptavidin mutein with the activated (by maleimid functions) amino acids of the other batch of modified streptavidin mutein. By this reaction, multimers/oligomers of the streptavidin mutein are formed. These oligomers can have any suitable number of "individual molecule" or streptavidin building block" higher than 3 and the oligomerization degree can be varied according to the reaction condition (see FIG. 24). After reacting these two batches of the modified streptavidin mutein, the oligmeric soluble multimerization reagent is typically isolated via size exclusion chromatography and any desired fraction can be used as multimerization reagent. Typically, the oligomers do not have (and do not need to have) a single molecular weight but they usually observe a statistical weight distribution such as Gaussian distribution. Any oligomer with more than three streptavidin homotetramers (building blocks; (n≥3)) can be used as soluble multimerization reagent. The oligomers might have, for example from 3 to 25 steptavidin mutein homotetramers. With a molecular weight of about 50 kDa for streptavidin muteins such as the mutein "m1" or "m2" described in more detail below, these soluble oligomers have a molecular weight from about 150 kDa to about 1250 kDa. Since each streptavidin molecule/mutein has four biotin binding sites such a multimerization reagent provides 12 to 100 binding sites Z1 (and Z2) as described herein.

In accordance with the above disclosure, in addition to such oligomeric multimerization reagents that only contain cross-linked streptavidin homotetramers, it is possible to react tetrameric streptavidin muteins to a carrier to obtain multimerization reagents that are used in the present invention. In addition to the above described reaction with a polysaccharide, it is also possible to use physiologically or pharmaceutically acceptable proteins such as serum albumin (for example human serum albumin (HSA) or bovine serum albumin (BSA) as carrier protein. In such a case, the streptavidin mutein (either as individual homo-tetramer or also in the form of oligomers with n≥3) can be coupled to the carrier protein via non-covalent interaction. For this purpose, biotinylated BSA (which is commercially available from various suppliers such as ThermoFisher Scientific, Sigma Aldrich or Vectorlabs, to name only a few) can be reacted with the streptavidin mutein. When so doing, some of the streptavidin oligomers will non-covalently bind via one or more biotin binding sites (Z1, Z2) to the biotinylated carrier protein, leaving the majority of the binding sites (Z1, Z2) of the oligomer available for binding the agents such as the first agent and optionally the second agent and any further agent as described herein. Thus, by such an approach a soluble multimerization reagent with a multitude of binding sites Z1 can be conveniently prepared (see FIG. 24). Alternatively, a streptavidin mutein (either as individual homo-tetramer or also in the form of oligomers with n≥3) can be covalently coupled to a synthetic carrier such as a polyethylene glycol (PEG) molecule. Any suitable PEG molecule can be used for this purpose, as long as the PEG molecule and the respective multimerization reagent is soluble. Typically, PEG molecule up to a molecular weight of 1000 Da are all soluble in water or culture media that may be used in the present invention. Such PEG based multimerization reagent can be easily prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA) with amino groups of the streptavidin mutein.

Under streptavidin or wild-type streptavidin (wt-streptavidin), the amino acid sequence disclosed by Argarana et al., Nucleic Acids Res. 14 (1986) 1871-1882 is referred to. Streptavidin muteins are polypeptides which are distinguished from the sequence of wild-type streptavidin by one or more amino acid substitutions, deletions or additions and which retain the binding properties of wt-streptavidin. Streptavidin-like polypeptides and streptavidin muteins are polypeptides which essentially are immunologically equivalent to wild-type streptavidin and are in particular capable of binding biotin, biotin derivative or biotin analogues with the same or different affinity as wt-streptavidin. Streptavidin-like polypeptides or streptavidin muteins may contain amino acids which are not part of wild-type streptavidin or they may include only a part of wild-type streptavidin. Streptavidin-like polypeptides are also polypeptides which are not identical to wild-type streptavidin, since the host does not have the enzymes which are required in order to transform the host-produced polypeptide into the structure of wild-type streptavidin. The term "streptavidin" also includes streptavidin tetramers and streptavidin dimers, in particular streptavidin homotetramers, streptavidin homodimers, streptavidin heterotetramers and strepavidin heterodimers. Each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In a preferred embodiment, streptavidin muteins that are used as multimerization reagent are those streptavidin muteins which are described in U.S. Pat. No. 6,103,493 and also in DE 196 41 876.3. These streptavidin muteins have at least one mutation within the region of amino acid positions 44 to 53, based on the amino acid sequence of wild-type streptavidin. Preference is given to muteins of a minimal streptavidin, which start N-terminally in the region of amino acids 10 to 16 of wild-type streptavidin and end C-terminally in the region of amino acids 133 to 142 of wild-type streptavidin. Examples of such preferred streptavidin muteins have a hydrophobic aliphatic amino acid instead of Glu at position 44, any amino acid at position 45, a hydrophobic aliphatic amino acid at position 46 or/and a basic amino acid instead of Val at position 47. The streptavidin mutein may be a mutein that comprises the amino acid sequence $Val^{44}$-$Thr^{45}$-$Ala^{46}$-$Arg^{47}$ (SEQ ID NO: 02) at sequence positions 44 to 47 r the streptavidin mutein (analog) that comprises the amino acid sequence $Ile^{44}$-$Gly^{45}$-$Ala^{46}$-$Arg^{47}$ (SEQ ID NO: 03) at sequence positions 44 to 47 of wild type streptavidin. Such muteins are described in U.S. Pat. No. 6,103,493, for example, and are commercially available from IBA GmbH in the form of mutein "m1" and mutein "m2" under the trademark Strep-Tactin®.

A method according to the present invention may in some embodiments be used to deplete a sample of reagents that have previously been used in cell expansion. The first or second agent and the respective free partner (the competition agent) may, for instance, be present included in the eluate of an expansion method as described above. Using a method according to the invention such reagents may be at least essentially, including entirely removed from a sample, e.g. from a cell population. As an illustrative example, a first or second agent as defined above may be depleted from a sample to levels that are below the detection limit of e.g. FACS or Western Blot. A competition reagent (free first or second binding partner or analogue thereof) may have been used in order to terminate and control the expansion and release the cell population form the multimerization agent. This competition reagent may have a binding site that is capable of specifically binding to the binding site Z of the affinity reagent in a "removal cartridge" of WO 2013/124474. In such an embodiment the respective method of the invention may also serve in depleting the first and second agent and the competition reagent, including removing the same.

A method according to the present invention may be carried out at any temperature at which the viability of the cell population is at least essentially uncompromised. When reference is made herein to conditions that are at least essentially not harmful, not detrimental or at least essentially not compromising viability, conditions are referred to, under which the percentage of the population of cells that are to be expanded with full viability, is at least 70%, including at least 75%, at least 80%, at least 85%, at least 90%, at least 92%, at least 95%, at least 97%, at least 98%, at least 99% or at least 99.5%. In some embodiments a method according to the invention is carried out at a temperature of about 20° C. or higher. Depending on the cell population to be expanded a suitable temperature range may for instance be from about 20° C. to about 45° C., including from about 25° C. to about 40° C., or from about 32° C. to 37° C. In some embodiments a method according to the invention is carried out at a constant temperature value, or at a selected temperature value ± about 5° C., ± about 4° C., ± about 3° C., ± about 2° C., ± about 1° C. or ± about 0.5° C. The person skilled in the art is able to empirically determine a suitable temperature, taking into account the nature of the cells and the expansion conditions. Typically human cells are expanded at a temperature such as 37° C.

In a further embodiment, the invention provides an in vitro-method of expanding a population of cells, comprising contacting a sample comprising a population of cells with a multimerization reagent, wherein the multimerization reagent is in a soluble form and has immobilized thereon (bound thereto) a first agent that provides a primary activation signal to the cells. The multimerization reagent comprises at least one binding site Z1 for the binding of the first agent, wherein the first agent comprises at least one binding partner C1, wherein the binding partner C1 is able of binding to the binding site Z1 of the multimerization reagent. The first agent is bound to the multimerization reagent via the bond formed between the binding partner C1 and the binding site Z1, and the first agent binds to a receptor molecule on the surface of the cells, thereby providing a primary activation signal to the cells and thereby activating the cells. It is expressly noted here that when a soluble multimerization agent is used, the bond between the binding part C1 and the binding site Z1 does not need to be reversible.

In an embodiment of this second the multimerization agent has immobilized thereon (bound thereto) a second agent that stimulates an accessory molecule on the surface of the cells, wherein the second agent comprises a binding partner C2, wherein the binding partner C2 is able of being bound to a binding site Z2 of the multimerization reagent. The second agent is bound to the multimerization reagent via the bond formed between the binding partner C2 and the binding site Z2, wherein the second agent binds to the accessory molecule on the surface on the surface of the cells, thereby stimulating the activated cells.

In one embodiment of this second method, the bond formed between the binding partner C1 and the binding site Z1 may be irreversible and/or also the bond formed between the binding partner C2 and the binding site Z2 may be irreversible.

In a different embodiment of this second method, the bond formed between the binding partner C1 and the binding site Z1 may be reversible. Also the bond formed between the binding partner C2 and the binding site Z2 may be reversible. In this case, the dissociation constant ($K_d$) for the reversible binding between said binding site Z1 and said binding partner C1 and/or for the reversible binding between said binding site Z2 and said binding partner C2 may be in the range of $10^{-2}$ M to $10^{-13}$ M.

In this second method that is based on a soluble multimerization reagent, the first and second reagent as well as the multimerization reagent and all other reagents and cell populations can otherwise be used in the same manner as disclosed above for the method that makes use of reversible between the first or second agent and the multimerization reagent.

The invention further provides a reagent kit for expanding a population of cells, the kit comprising
(i) a multimerization reagent, wherein the multimerization reagent comprises at least one binding site Z for the reversible binding of a first agent,
(ii) a first agent that binds to a receptor molecule on the surface of the cells, thereby providing a primary activation signal to the cells and thereby activating the cells, wherein the first agent comprises at least one binding partner C1, wherein the binding partner C1 is able of reversibly binding to a binding site Z1 of the multimerization reagent, wherein the first agent is bound to the multimerization reagent via the reversible bond formed between the binding partner C1 and the binding site Z1, and
(iii) a second agent that stimulates an accessory molecule on the surface of the cells, wherein the second agent comprises a binding partner C2, wherein the binding partner C2 is able of reversibly binding to a binding site Z2 of the multimerization reagent, wherein the second agent is bound to the multimerization reagent via the bond formed between the binding partner C2 and the binding site Z2, wherein the second agent binds to the accessory molecule on the surface on the surface of the cells, thereby stimulating the activated cells.

The invention also provides a reagent kit for expanding a population of cells, the kit comprising
(i) a multimerization reagent, wherein the multimerization reagent is in soluble form and comprises at least one binding site Z for the reversible binding of a first agent,
(ii) a first agent that binds to a receptor molecule on the surface of the cells, thereby providing a primary activation signal to the cells and thereby activating the cells, wherein the first agent comprises at least one binding partner C1, wherein the binding partner C1 is able of binding to a binding site Z1 of the multimerization reagent, wherein the first agent is bound to the multimerization reagent via the reversible bond formed between the binding partner C1 and the binding site Z1.

This second reagent kit may further comprises (iii) a second agent that stimulates an accessory molecule on the surface of the cells, wherein the second agent comprises a binding partner C2, wherein the binding partner C2 is able of binding to a binding site Z2 of the multimerization reagent, wherein the second agent is bound to the multimerization reagent via the bond formed between the binding partner C2 and the binding site Z2.

A kit as disclosed herein is in particular used when the population of cells is a lymphocyte population.

In accordance with the disclosure above, the invention also provides novel multimerization reagents and novel composition comprising multimerization reagents that care capable of expanding a population of cells. Such a multimerization reagent that is capable of expanding a population of cells is a multimerisation reagent that is in soluble form and comprises at least one binding site Z1 for the reversible binding of a first agent that provides a primary activation signal to the cells, wherein the multimerization reagent has reversibly immobilized thereon (bound thereto) said first agent that provides a primary activation signal to the cells; wherein the first agent comprises at least one binding partner C1, wherein the binding partner C1 is able of reversibly binding to the at least one binding site Z1 of the multimerization reagent, wherein the first agent is bound to the multimerization reagent via the reversible bond formed between the binding partner C1 and the binding site Z1. It should be noted here that such a multimerization agent can have immobilized thereon any of the first agent that are described herein.

A multimerization reagent of the invention may further comprise at least one binding site Z2 for the reversible binding of a second agent that stimulates an accessory molecule on the surface of the cells, wherein the multimerization reagent has reversibly immobilized thereon (bound thereto) the second agent that stimulates an accessory molecule on the surface of the cells, wherein the second agent comprises a binding partner C2, wherein the binding partner C2 is able of binding to the at least one binding site Z2 of the multimerization reagent. In this embodiment the second agent is bound to the multimerization reagent via the bond formed between the binding partner C2 and the binding site Z2.

Also in line with the disclosure given above, such a multimerization reagent is capable of expanding a lymphocyte population or a subpopulation contained in the lympocyte population. The lymphocyte population to be expanded may any suitable population, for example, a B cell population, a T cell population, or a natural killer cell population. The T-cell population may be an antigen-specific T cell population, a T helper cell population, a cytotoxic T cell, a memory T cell, a regulatory T cell, or a natural killer T cell population. Accordingly, in such embodiments of the multimerization reagent the first agent is able to stimulate a TCR/CD3 complex-associated signal in the T cells. The first agent present in the multimerization reagent may thus be binding reagent that specifically binds CD3, while the second agent that binds the accessory molecule may be a binding agent that specifically binds CD28 or CD137.

In embodiments of the multimerization reagent the first agent that specifically binds CD3 may be an anti-CD3-antibody, a divalent antibody fragment of an anti-CD3 antibody, a monovalent antibody fragment of an anti-CD3-antibody, and/or a proteinaceous CD3 binding molecule with antibody-like binding properties. In these embodiments, the second agent that specifically binds CD28 or CD137 may be an anti-CD28-antibody, a divalent antibody fragment of an anti-CD28 antibody, a monovalent antibody fragment of an anti-CD28-antibody, a proteinaceous CD28 binding molecule with antibody-like binding properties, an anti-CD137-antibody, a divalent antibody fragment of an anti-CD137 antibody, a monovalent antibody fragment of an anti-CD137-antibody, a proteinaceous CD137 binding molecule with antibody-like binding properties, 4-1BB ligand, and any mixture thereof. Thus, a multimerization reagent of the invention can generally have immobilized thereon one kind of first agent and a mixture of second agents, for example, an anti-CD3 antibody as first agent and for example, an anti-CD28 antibody and 4-1BB ligand as (joint) second agents.

If the multimerization reagent is to be used for the expansion of B cells, the first agent immobilized on the multimerization reagent may be a binding reagent that specifically binds CD40 or CD137. In accordance with the disclosure given herein, in such embodiments the first binding reagent that specifically binds CD40 or CD137 may be selected from an anti-CD40-antibody, a divalent antibody fragment of an anti-CD40 antibody, a monovalent antibody fragment of an anti-CD40-antibody, and a proteinaceous CD40 binding molecule with antibody-like binding properties or an anti-CD137-antibody, a divalent antibody fragment of an anti-CD137 antibody, a monovalent antibody fragment of an anti-CD137-antibody, a proteinaceous CD137 binding molecule with antibody-like binding properties, and CD40 ligand (CD154).

Also in accordance with the general disclosure of the present invention, in the multimerization reagent as described herein the binding sites Z1 and Z2 of the multimerization reagent can be identical. As described above, such a multimerization reagent may comprises an oligomer or a polymer of streptavidin, an oligomer or a polymer of avidin, an oligomer or a polymer of an analog of streptavidin that reversibly binds biotin, an oligomer or a polymer of an analog avidin that reversibly bind biotin, a reagent that comprises at least two chelating groups K, wherein the at least two chelating groups are capable of binding to a transition metal ion, thereby rendering the reagent capable of binding to an oligohistidine affinity tag, multimeric glutathione-S-transferase, multimeric calmodulin and a biotinylated carrier protein.

A novel composition provided herein that is capable of expanding a population of cells may comprise
  (i) a first multimerization reagent, wherein the first multimerisation reagent is in soluble form and comprises at least one binding site Z1 for the reversible binding of a first agent that provides a primary activation signal to the cells, wherein the first multimerization reagent has reversibly immobilized thereon (bound thereto) said first agent that provides a primary activation signal to the cells, wherein the first agent comprises at least one binding partner C1, wherein the binding partner C1 is able of reversibly binding to the at least one binding site Z1 of the multimerization reagent, wherein the first agent is bound to the multimerization reagent via the reversible bond formed between the binding partner C1 and the binding site Z1, and
  (ii) a second multimerization reagent, wherein the second multimerization reagent is in soluble form and comprises at least one binding site Z2 for the reversible binding of a second agent that stimulates an accessory molecule on the surface of the cells, wherein the multimerization reagent has reversibly immobilized thereon (bound thereto) said second agent that stimulates an accessory molecule on the surface of the cells, wherein the second agent comprises a binding partner C2, wherein the binding partner C2 is able of binding to the at least one binding site Z2 of the multimerization reagent, wherein the second agent is bound to the multimerization reagent via the bond formed between the binding partner C2 and the binding site Z2.

Such a novel composition is, for example, the reaction mixture used in Example 13, in which two separate multimerization reagents were functionalized either with an αCD3 Fab fragment alone or an αCD28 Fab fragment alone. It is noted in this context, that such a composition was shown in Example 13 to have the same expansion efficiency as a single multimerization reagent on which both the first agent and the second agent are jointly immobilized. Thus, the combined use of two or more multimerization reagents being functionalized individually with only one type of reagent (for example, one first or one second agent) is functionally equivalent to using for the expansion one joint multimerization reagent which has immobilized thereon both a first agent and a second agent. In this context, it is also noted that a multimerization reagent of the present invention be functionalized with as many agents (for example, one, two, three, four or even more agents) that are intended to be used for the expansion of a selected cell population. A third or fourth agent may, for example, for example provide a stimulus for the expansion of a desired subpopulation of cells. See in this context, for instance, Example 13 in which a soluble multimerization reagents was reversibly functionalized with three reagents, namely a αCD3 Fab fragment as first reagent, a αCD28 Fab fragment as second reagent and a αCD8 Fab fragment as third reagent to enrich the subpopulation of CD8+ T cells in a sample of a population of CD3+ T cells (lymphocyte). By using such a combinations of agents that can all be reversibly immobilized on the same multimerization reagent, the present invention allows for the possibility to preferentially expand or selectively enrich any desired cell (sub)population from an sample that, for example, comprises a variety of different subpopulations. In this context, it is noted that it however also possible to use for this purpose use three different multimerization reagents, for example, a first multimerization reagent that is functionalized with only a αCD3 Fab fragment, a second multimerisation reagent that is functionalized with a αCD28 Fab fragment and a third multimerization reagent that is functionalized with a αCD8 Fab fragment. Likewise, it is possible to use only two different multimerization reagents, a first multimerization reagent that is functionalized with only a αCD3 Fab fragment and a second multimerisation reagent that is functionalized with both a αCD28 Fab fragment and a αCD8 Fab fragment. Accordingly, the present invention allows to design any kind of wanted expansion reagent in a modular fashion.

The invention also provides an in vitro-method of serially expanding a population of lymphocytes, wherein the population of lymphocytes comprises T cells. This method comprises
contacting a sample comprising the T cell comprising population of lymphocytes with a multimerization reagent,
wherein the multimerization reagent is in a soluble form and has reversibly immobilized thereon (i) a first agent that provides a primary activation signal to the T cells and (ii) a second agent which stimulates an accessory molecule on the surface of the T cells,
wherein the multimerization reagent comprises at least one binding site Z1 for the reversible binding of the first agent,
wherein the first agent comprises at least one binding partner C1, wherein the binding partner C1 is able of reversibly binding to the binding site Z1 of the multimerization reagent, wherein the first agent is bound to the multimerization reagent via the reversible bond formed between the binding partner C1 and the binding site Z1,
wherein the multimerization reagent comprises at least one binding site Z2 for the reversible binding of the second agent,
wherein the second agent comprises at least one binding partner C2, wherein the binding partner C2 is able of reversibly binding to the binding site Z2 of the multimerization reagent, wherein the first agent is bound to the multimerization reagent via the reversible bond formed between the binding partner C2 and the binding site Z2,
wherein the first agent binds to a receptor molecule on the surface of the T cells, thereby providing a primary activation signal to the cells and thereby activating the T cells,
wherein the second agent binds to the accessory molecule on the surface of the T cells, thereby stimulating the activated cells, the first agent and the second agent thereby together inducing the T cells to expand.

In this method contacting the sample that contains the population of lymphocytes that in turn contains the T cell population with the soluble multimerization reagent that has immobilized thereon the first and second agent results in specific binding of T cells to the multimerization reagent.

The contacting of the sample comprising the T cell comprising population of lymphocytes with the multimerization reagent can be carried out in a bioreactor such as a hollow-fiber bioreactor (e.g. hollow fiber bioreactor of the Quantum® cell expansion system) or a plastic bag bioreactor (e.g. Cellbag® used in Xuri Cell Expansion System W25 from GE Healthcare).

This method further comprises contacting the population of lymphocytes (reaction mixture containing the T cells bound to the multimerization reagent via the first agent and the second agent) with (i) a free first binding partner C1 or an analogue thereof capable of disrupting the bond between the first binding partner C1 and the binding site Z1 and (ii) a free second binding partner C2 or an analogue thereof, capable of disrupting the bond between the second binding partner C2 and the binding site Z2. By so doing the reversible bond between said binding partner C1 of the first agent and said binding sites Z1 as well as the reversible bond between said binding partner C2 of the second agent and said binding site Z2 of said multimerization reagent is disrupted, thereby releasing in an eluate the T cells bound to the multimerization reagent via the first agent and the second agent and stopping the expansion of the T cells.

In this method the eluate (the reaction mixture in which the expansion reaction has been terminated by addition of the free first partner(s) or analogue(s) thereof) that contains the expanded T cell population may be exposed to chromatography on a suitable (first) stationary phase. The (first) stationary phase may be a gel filtration matrix and/or an affinity chromatography matrix as described in International patent application WO 2013/124474. This gel filtration and/or affinity chromatography matrix comprises an affinity reagent, wherein the affinity reagent comprises a binding site Z1 and/or Z2 specifically binding to the binding partner C1 and/or C2 comprised in the first agent or the second agent. By so doing the first agent, the second agent, the first binding partner C1 and/or the free second binding partner C2 are immobilized on the stationary phase. In this method, the first stationary phase is fluidly connected to the bioreactor.

In one of the embodiments of this serial expansion the binding sites Z1 and Z2 of the multimerization agent are identical. In addition, a single multimerization agent may be used. When a soluble multimerization agent is used, the T cell population (or the expanded cell population in general) is separated from the soluble multimerization reagent. The separation/removal might be carried out using a second stationary phase. For this purpose, a mixture comprising the T cells and the soluble multimerization reagent are exposed, before or after being applied onto the first stationary phase described above, to chromatography on a suitable second stationary phase. This secondary stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z1 and/or binding site Z2, if present, of the multimerization reagent, thereby immobilizing the multimerization reagent on the stationary phase. If a streptavidin based multimerization agent is used and both first and second agents have a streptavidin binding peptide as binding partner C1 or C2, the binding partner D that is comprised in the affinity reagent of this second stationary phase can be biotin. The soluble oligomer of streptavidin or of a streptavidin mutein that is used as multimerization reagent then binds to the biotin that is usually covalently coupled to a chromatography matrix such as biotin-Sepharose™ that is commercially available.

In this method of serial expansion the first agent may stimulates a TCR/CD3 complex-associated signal in the T cells and the first agent may thus be a binding reagent that specifically binds CD3. In addition, the accessory molecule on the T cell may be CD28. In this case the second agent that binds the accessory molecule is a binding reagent that specifically binds CD28.

In this method of serial expansion, the T cells may be transfected either during or after expansion e.g. with a T cell receptor (TCR) or a chimeric antigen receptor (CAR, also known as artificial T cell receptor). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via the de novo introduced receptor). This second type of stimulus may comprise an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). Cf. in this respect, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In this method, the population of lymphocytes that comprises T cells can be a population of peripheral blood mononucleated cells (PBMC) or a population of enriched or purified T cells. The population of lymphocytes may, for example, be derived from whole blood, or from a non-mobilized apheresis product or a frozen tissue preparation.

In this method of serial expansion that is based on a soluble multimerization reagent, the first and second reagent as well as the multimerization reagent and all other reagents and cell populations can otherwise be used in the same manner as disclosed above for the method that makes use of reversible between the first or second agent and the multimerization reagent.

The invention is further directed to an arrangement of a bioreactor and a first stationary phase for chromatography. The bioreactor is suitable for the expansion of cells, and the stationary phase is suitable for cell separation and removal of reagents. The first stationary phase is a gel filtration matrix and/or affinity chromatography matrix, wherein the gel filtration and/or affinity chromatography matrix comprises an affinity reagent, wherein the affinity reagent comprises a binding site Z1 specifically binding to a binding partner C1 comprised in a first agent and/or the affinity reagent comprises a binding site Z2 specifically binding to a binding partner C2 comprised in a second agent. The first stationary phase is thereby being suitable of immobilizing thereon the first agent and/or the second agent, the first binding partner C1 and/or the free second binding partner C2. In addition the bioreactor and the stationary phase are fluidly connected. This arrangement can be used in the serial expansion as explained above and can be integrated into known cell expansion systems such as the Quantum® cell expansion system) or the Xuri Cell Expansion System W25.

In this arrangement the first stationary phase is either comprised in a chromatography column or is a planar stationary phase. The arrangement may further comprises a second stationary phase which is fluidly connected to the first stationary phase. The secondary stationary phase may be a gel filtration matrix and/or affinity chromatography matrix, wherein the gel filtration and/or affinity chromatography matrix comprises an affinity reagent. This affinity reagent may comprise a binding partner D that (specifically) binds to the binding site Z1 of the multimerization reagent, thereby being suitable of immobilizing the multimerization reagent on the stationary phase.

The invention is further directed to an apparatus for purification and expansion of a population of cells, the apparatus comprising at least one arrangement of a bioreactor and a first stationary phase or a second stationary phase for chromatography as defined above.

The apparatus may further comprise a plurality of arrangements of a bioreactor and a stationary phase being fluidly connected in series.

The apparatus may comprise a sample inlet being fluidly connected to the bioreactor of the arrangement of a bioreactor and the stationary phase for chromatography. The apparatus may also comprise a sample outlet for purified and expanded target cells, the sample outlet being fluidly connected to the stationary phase of the last of the at least one arrangement of a bioreactor and the stationary phase for chromatography.

Finally, the apparatus may be designed as a functionally closed system.

As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXPERIMENTAL EXAMPLES

Example 1

Stimulation/Expansion of CD3+ T Responder Cells with αCD3/αCD28 Fab Fragments that were Reversibly Immobilized on Beads Coated with the Streptavidin Mutein Strep-Tactin®

300.000 CD3+CD62L-responder T cells (Tresp, isolated by serial magnetic enrichment from a non-mobilized donor apheresis product) were labeled with 3 µM CFSE and stimulated with 5 µl of a 15 µl preparation of Streptactin® beads (10 mg magnetic particles/ml, loaded with 35 µg Streptactin®/mg beads) either loaded with 0.5 µg αCD3 Fab fragment alone, 0.5 µg αCD28 Fab fragment alone or a mixture of 0.5 µg αCD3 Fab fragment and 0.5 µg αCD28 Fab.

The αCD3 Fab fragment used was derived from the CD3 binding monoclonal antibody produced by the hybridoma cell line OKT3. The hybridoma cell line OKT3 and the OKT3 antibody are described in U.S. Pat. No. 4,361,549, the cell line has been deposited under accession number ATCC® CRL-8001™). The CD28 Fab used was derived from the monoclonal anti-human CD28 antibody CD28.3 (Vanhove et al, BLOOD, 15 Jul. 2003, Vol. 102, No. 2, pages 564-570). The nucleotide sequence of the variable domains of this antibody CD28.3 has been deposited in GenBank in the form of a synthetic single chain Fv construct anti-human CD28 antibody scFv28.3 under GenBank accession number AF451974.1).

Both Fab fragments were recombinantly produced in *E. coli* as described in International patent applications WO2013/011011 and WO 2013/124474 carrying as constant domains (CH1 and Ckappa) an IgG1 consensus sequence. The heavy chain of both Fab fragments was carboxy-terminally fused with a sequential arrangement of two streptavidin binding modules (SAWSHPQFEK(GGGS)$_2$GGSAWSHPQFEK, (SEQ ID NO: 07)), that is commercially available as "Twin-Strep-tag® from IBA GmbH, Göttingen, Germany). The αCD3 Fab fragment was used as first agent with the streptavidin binding peptide serving as binding partner C1 and the αCD28 Fab fragment was used as second agent with the treptavidin binding peptide serving as binding partner C2. The (tetrameric) streptavidin mutein "Strep-tactin®" serves as multimerization reagent on which both Fab fragments were reversibly immobilized.

In the expansion experiment, Tresp cells stimulated with blank beads (no Fab) served as negative control. Tresp cells were seeded in triplets in 48-well plates along with 300.000 CD3 cells autologous feeder cells (irradiated with 30 Gy) in 3 ml complete cell culture medium (RPMI (Gibco) supplemented with 10% (v/v) fetal calf serum, L-glutamine, b-mercapto ethanol, HEPES, penicillin, streptomycine and gentamycine) supplemented with 10 U/ml interleukin 2 (IL-2). The cells were incubated at 37° C. without media exchange and analyzed after 4 days by FACS analysis. FACS staining and analysis was done after 10 min incubation with 100 μM D-biotin. One representative plot for each condition is shown in FIG. 4. Plots show live CD3+ cells that were stained with propidium iodide (PI) for live/dead discrimination. FIG. 4a is a histogram showing size-distribution (forward scatter) of stimulated cells. FIG. 4a shows that a specific cell population of Tresp cells was stimulated and expanded (increase in size/number compared to the unstimulated "beads only" control) when incubated in the presence of beads on which a mixture of 0.5 μg αCD3 Fab fragment and 0.5 μg αCD28 Fab was immobilized, after being stimulated in vitro with αCD3/αCD28 Fab fragments that were reversibly immobilized on beads coated with the streptavidin mutein Strep-tactin®. FIG. 4B depicts histograms of the dilution of the proliferation dye CFSE representing the degree of proliferation according to the number of cells per cell division (indicated on top of FIG. 4B, 0 represents undivided cells; 5 represents cells that have gone through at least 5 divisions). It can be seen from FIG. 4B that the population of T cells stimulated with the beads on which a mixture of 0.5 μg αCD3 Fab fragment and 0.5 μg αCD28 Fab was immobilized have mostly gone through three cell divisions and represent a more uniform proliferation pattern than with a single stimulus alone (small number of cells within the undivided peak "0"). The increased absolute amount of proliferation (more cells have proliferated uniformly after 4 d stimulation with αCD3 and αCD28 functionalized beads) is also represented by a more intense consumption of media as depicted by a indicator color change to yellow in FIG. 4C.

Example 2

Analysis of the Differential Intracellular Calcium Mobilization in Jurkat Cells

Real-time low-cytometric analysis of the differential intracellular calcium mobilization induced in Jurkat cells that are either labeled with the αCD3 antibody clone OKT3 or with Fab fragments of OKT3 being multimerized with Strep-tactin® was examined here.

For this purpose, Jurkat cells were loaded with the calcium-sensitive dye Indo-1-AM and calcium release was triggered by injection of either αCD3 monoclonal antibody OKT3 (produced by the hybridoma cell line OKT3, see above, black squares) or αCD3 Fab fragments (derived from the parental cell line OKT3) that were multimerized by reversible binding of its streptavidin binding peptide to soluble Strep-Tactin fluorescently conjugated with phycoerythrin. In the case of the intact multimeric OKT3 Fab-Strep-Tactin complexes, the calcium release was triggered over an identical time period as with the parental antibody clone (dark grey triangles). Activation of cells could be completely avoided by injection of D-biotin treated, pre-dissociated Fab-Strep-Tactin complexes (light grey circles) identical to injection of the PBS negative control (inverted white triangles). Application of ionomycine served as positive control for calcium influx. Time-resolved changes in intracellular $Ca^{2-}$ concentration were monitored by flow-cytometry based on the change in FL6/FL7 ratio. It can be seen from FIG. 5A that both the parental antibody OKT3 as well as the multimerized monovalent Fab fragment of OKT3 effected calcium release, meaning that the multimerized monovalent Fab fragment of OKT3 is essentially as functional as the parental antibody. Notably, the multimeric OKT3 Fab fragment was not able to trigger calcium release if biotin was added to Strep-tactin on which the OKT3 Fab fragment was immobilized prior to the addition of the Streptactin-OKT3 Fab fragment. In this case, the biotin disrupted the reversible bond formed between Strep-tactin as multimerization agent and the OKT3 Fab fragment. The monovalent Fab fragment was therefore displaced from the multimerisation agent and after dissociation was not able to trigger calcium release by binding to CD3 of the Jurkat cells.

In the experiments shown in FIG. 5B indo-1-AM-labeled Jurkat cells were activated by OKT3 derived αCD3 Fab-Strep-Tactin-complexes as described in FIG. 5a. Injection of intact (upper graph) or pre-dissociated complexes (lower graph) served as positive or negative controls respectively. In addition, stimulation of cells with intact Fab-Strep Tactin-complexes followed by subsequent injection of D-biotin (near the peak activation at t=140 s) resulted in abrupt disruption of αCD3 Fab-multimer signaling (middle graph). Injection of ionomycine into the pre-dissociated Fab complex group served as positive control. Data are representative of three different experiments. Importantly, FIG. 5B shows that the addition of D-biotin to the sample rapidly displaces the Fab fragment from the Strep-tactin multimerization agent, thereby effectively terminating the calcium release even under ongoing calcium stimulation and demonstrating that the dissociated OKT3 Fab fragment is not any longer biologically active. Likewise, the multimeric OKT3 Fab fragment was also not able to trigger calcium release when biotin was added to the Strep-tactin-OKT3 Fab fragment multimer prior to the addition of the Streptactin-OKT3 Fab sample to the Jurkat cells.

Example 3

Reversible Staining of Cells by CD3 Fab-Multimers

This Example examines the reversible staining of cells by CD3 Fab-multimers. Freshly isolated PBMCs were stained with either the αCD3 monoclonal antibody clone OKT3 (left dot plot, parental clone for the Fab-multimers) or cognate phycoerythrine (PE)-labeled OKT3 Fab-multimers and analyzed either before (second left column) or after treatment with D-biotin (middle column). Remaining Fab monomers were then detected after subsequent washing steps using fresh PE-labeled Strep-Tactin® (second right column). Secondary Fab-multimer staining of reversibly stained cells served as control (right column). Only live CD3 cells which are negative in staining with propidium iodide (PI) for live/dead discrimination are shown in FIG. 6. Numbers in dot plots indicate the percentage of cells within gates. This experiment shows that the staining of CD3+ P BMCs with an anti-CD3 Fab fragment multimerized with Streptactin as multerization reagent is fully reversible by addition of D-biotin and that the monovalent Fab fragment alone does not bind to the CD3 molecule present on PBMCs.

Example 4

Reversible Isolation of Cells by CD28 Fab-Multimers

This Example shows the isolation of cells by reversible binding of anti-CD28 Fab fragments multimerized with Strep-Tactin® magnetic particles (the magnetic particles are available from IBA GmbH Göttingen, Germany). The Fab fragments derived from the antibody CD28.3 described in Example 1 above were used for this purpose. CD28+ cells were selected/isolation by Fab-multimer magnetic cell selection from freshly isolated PMBCs as essentially described in International Patent Application WO2013/011011. Before selection cells were control stained with either the cognate fluorescent αCD28-multimers (left dot plot) or with an antibody directed against the immunoglobulin kappa light chain (second left dot plot, α-Ig kappa mAb) as a control staining. After selection, CD28+ cells were treated with D-biotin and subsequently washed to remove magnetic beads and Fab-monomers. Liberated CD28+ cells were subsequently (re-) stained either with CD28 Fab-multimers (second right dot plot) or with the α-Igkappa mAb (right dot plot) to detect potentially remaining Fab-monomers. Only live (PI$^{negative}$) CD3+ cells are shown. Numbers in dot plots indicate the percentage of cells within gates. FIG. 7 shows that CD28+ cells can be isolated from PMBC using such multimerized anti-CD28 Fab fragment and that all isolation reagents including the anti CD28 Fab-monomers can be removed after selection.

Example 5

Stimulation/Expansion of CD3+ T Responder Cells with αCD3/αCD28 Fab Fragments that were Reversibly Immobilized on Soluble Strep-Tactin In this example CD3+ T responder cells (isolated by magnetic selection from a sample of fresh PBMCs obtained from a Ficoll gradient) were expanded after in vitro stimulation with αCD3/αCD28 Fab fragments that were reversibly immobilized on soluble oligomeric Strep-tactin® acting as a soluble multimerization reagent. The oligomeric Strep-tactin® was obtained by polymerizing Strep-tactin® with sulfo SMCC (sulfosuccinimidyl 4-(N-maleimidomethyl)cyclohexane-1-carboxylate, product #22122 Thermo Scientific) and iminothiolan (product #26101 Thermo Scientific) according to the protocol of the manufacturer (Thermo Scientific). The oligomeric streptavidin were separated from monomeric (unreacted) and dimeric streptavidin mutein by size exclusion chromatography and the so obtained fraction of the oligomeric streptavidin mutein (n≥3) was used as soluble multimerization reagent.

For the in vitro expansion, 300.000 CD3+ responder T cells (Tresp) were labeled with 2 μM Carboxyfluorescein succinimidyl ester (CFSE) and stimulated with varying amounts of a preparation of soluble Strep-tactin® oligomers on which a combination of the above described αCD3 OKT3 Fab fragment and the αCD28 Fab fragment of the antibody 28.3 (both carrying the above-mentioned Twin-Strep-tag® as streptavidin binding peptide at the heavy chain) were immobilized. ("1×" corresponds to 3 μg multimerized Streptactin functionalized with 0.5 μg of the αCD3- and 0.5 μg αCD28 monomeric Fab fragment, the numbers "0.5×", "2×" and "5×" indicate the respective n-fold amount of "1×"). Tresp cells either left unstimulated or were stimulated with blank Strep-tactin multimers (no Fab) served as negative controls. Tresp cells were seeded in duplicates in 48-well plates along with 300.000 CD3 negative autologous feeder cells (irradiated with 30 Gy) in 1 ml cell culture medium supplemented with 20 U/ml IL-2. Cells were incubated at 37° C. without media exchange and proliferation was analyzed according to CFSE dilution after 5 days by FACS analysis. FIG. 8A shows the increase in the size distribution of proliferating cells after 5 days in culture compared to the negative controls. FIG. 8B shows that CD3+ Tresp cells were properly stimulated and proliferated vigorously when incubated with soluble oligomeric Strep-tactin® (as compared to solid Streptactin magnetic particles in FIG. 4) on which a mixture of αCD3 Fab and αCD28 Fab fragments were immobilized. The results in FIGS. 8a and 8b indicate that under these in vitro conditions most of the CD3+ T responder cells divided (2 to 5 cell divisions) after engagement of the surface CD28 and TCR/CD3 complex with the αCD3 and αCD28 Fab fragments that were reversibly immobilized on soluble Strep-tactin® oligomers. After in vitro expansion the soluble Fab-Strep-Tactin stimulation reagents were dissociated and removed after D-biotin treatment. The dissociation and removal of monomeric Fab fragments was flow-cytometrically analyzed by restaining cells with phycoerythrine label Strep-Tactin®) (ST-PE). A representative histogram (dark grey histogram) is shown compared to the appropriate ST-PE only negative control (light gray histogram). It can be seen from FIG. 8C that both Fab fragments had completely dissociated and were entirely removed from the expanded cells. FIG. 8D shows the absolute number of live (trypan blue negative) cells after 5 days. The number was counted using a Neubauer counting chamber and plotted against the respective stimulation condition. Median cell numbers are shown in FIG. 8D; error bars indicate standard deviation (SD). FIG. 8D shows that all which mixtures of αCD3 Fab fragments and αCD28 Fab fragments that were immobilized on a soluble Strep-tactin multimerization reagent were equally effective in expanding the CD3+ cells and resulted in an approx. 4-fold increase of absolute cell numbers.

Example 6

Kinetics of Proliferation of Purified CD4+ and CD8+ T Responder Cells Stimulated In Vitro with Reversible aCD3/aCD28 Fab-Streptamer Multimers Without Medium Exchange In this example the expansion kinetics of proliferation of purified CD4+ and CD8+ T responder cells (Tresp) that were stimulated in vitro with αCD3/αCD28 Fab fragments that were reversibly immobilized soluble oligomeric streptavidin muteins were examined. For this purpose, soluble oligomeric Strep-tactin® mutein of two different sizes served as soluble multimerization reagent. The first kind of oligomeric Strep-tactin® was the fraction of the oligomeric streptavidin mutein (n≥3) obtained in Example 5 (also referred herein as "conventional Streptactin® backbone", illustrated by the triangle symbol with the tip on top in FIG. 13). The second kind of this oligomeric streptavidin mutein used as soluble multimerization reagent was an oligomeric streptavidin mutein (n≥3) that was reacted with biotinylated human serum albumin (also referred herein as "large Streptactin® backbone").

In this example 500.000 purified CD4+ or CD8+ responder T cells (Tresp) were separately stimulated with these two different Streptamer multimers as explained above, i.e. with either the Streptactin backbone of Example 5 (using a solution with a concentration of 1 mg oligomeric streptavidin mutein/ml)) or with the large Streptactin backbones (0.1 mg/ml). 3 μl of the both different backbones were either loaded with a combination of 0.5 μg of the αCD3 and 0.5 μg αCD28 Fab used in the earlier Examples that carried a streptavidin binding peptide SAWSHPQFEK(GGGS)$_2$GGSAWSHPQFEK (SEQ ID NO: 07) at the C-terminus of the heavy chain of the Fab fragment. In addition, 4.5 μl of the conventional Streptactin backbone was loaded with 0.5 μg αCD3 Fab fragment, 0.5 μg αCD8 Fab fragment (IBA GmbH Göttingen, that also carries at the C-terminus of the Fab fragment the streptavidin binding peptide SAWSHPQFEK(GGGS)$_2$GGSAWSHPQFEK (SEQ ID NO: 07) and 0.5 μg αCD28 Fab fragment. Untreated (unstimulated) Tresp cells served as negative control and Tresp cells stimulated with commercially available Dynabeads (beads on which αCD3 and αCD28 monoclonal antibodies are irreversible immobilized) as positive control. Tresp cells were seeded in duplicates in 48-well plates in 1 ml cell culture medium (RPMI 1640 (Gibco) supplemented with 10% (v/v fetal calf serum, 0.025% (w/v) L-glutamine, 0.025% (w/v) L-arginine, 0.1% (w/v) HEPES, 0.001% (w/v) gentamycine, 0.002% (w/v) streptomycine, 0.002% (w/v) peniciline) supplemented with 30 U/ml IL-2. Cells were incubated at 37° C. without media exchange and cell count was analyzed after 1, 3 and 6 days. In the experiments of FIG. 13 the expansion was carried out without medium exchange. The results for the CD4+ T responder cells are shown in FIG. 13A, the results for the CD8+ T responder cells are shown in FIG. 13B, with the graphs representing degree of proliferation according to the number of cells harvested per time point for CD4+ Tresp (FIG. 13A) and for CD8+ Tresp in FIG. 13B.

As can be seen from FIG. 13A the "smaller" soluble multimerization reagent on which αCD3 and αCD28 Fab fragments were reversibly immobilized provided for the same amount of expansion of CD4+ T cells as Dynabeads (which are so far the standard reagent for the expansion of T cells), while the "larger" oligomeric soluble streptactin provided for even better expansion compared to Dynabead. This improvement might be caused by the soluble "larger oligomeric multimerization reagent" being able to bind to more T cells at the same time than the "smaller" soluble oligomer, thereby being able to stimulate more CD4+ T cells than the "smaller" oligomer.

As evident from FIG. 13B, using the soluble multimerization reagents of the present invention CD8+ T cells could be expanded within the first 3 days at least as efficiently as with Dynabeads. Notably, in this time period, the expansion experiment that used a soluble multimerization reagent that in addition to αCD3 and αCD28 Fab fragments (as first and second agent) carried reversibly immobilized thereon αCD8 Fab fragment, showed the best degree of expansion under these culturing conditions. This indicates that it is possible by using a stimulus that is specific for a particular sub-population of cells (here the αCD8 Fab fragment) to increase or modulate the selectivity of the expansion, thereby being able to obtain larger amounts of a desired cell (sub)-population.

Thus, summarizing the above, Example 6 shows that the functionality of the soluble multimerization reagent used in the present invention in terms of triggering expansion of T cells is comparable to the current standard methodology of using Dynabeads for this purpose. However, since the stimulation can be controlled (and terminated, if wanted) by adding a competitor such as biotin in the case of a streptavidin based reversible interaction between the first and second agent and the multimerization reagent, the present invention provides a significant advantage over the Dynabeads technology since the expansion conditions can be optimized (it would for example be possible to stop the stimulation in the experiment of FIG. 13B after 3 days). In addition, since the soluble multimerization reagent can be easily removed from the reaction (for example, by immobilizing the reagent on a biotinylated column after the expansion reaction), the expansion method of the invention can be carried out and automated in closed systems that are, for example, needed for GMP production of cells for therapeutic purposes, without having to deal with the removal of beads such as Dynabeads.

Example 7

Kinetics of Proliferation of Purified CD4+ and CD8+ T Responder Cells Stimulated In Vitro with Reversible aCD3/aCD28 Fab-Streptamer Multimers with Medium Exchange Also in this example the expansion kinetics of proliferation of purified CD4+ and CD8+ T responder cells (Tresp) that were stimulated in vitro with αCD3/αCD28 Fab fragments that were reversibly immobilized on soluble oligomeric streptavidin muteins were examined. For this purpose, soluble oligomeric Strep-tactin® mutein of two different sizes served as soluble multimerization reagent. The first kind of oligomeric Strep-tactin® was the fraction of the oligomeric streptavidin mutein (n≥3) obtained in Example 5 (also referred herein as "conventional Streptactin® backbone", illustrated by the triangle symbol with the tip down in FIG. 13). The second kind of this oligomeric streptavidin mutein used as soluble multimerization reagent was obtained by reacting the oligomeric Strep-tactin (n≥3) obtained in Example 5 with biotinylated human serum albumin. This soluble oligomeric multimerization reagent is also referred herein as "large Streptactin® backbone.

In this example, 400.000 purified CD4+ or CD8+ responder T cells (Tresp) were separately stimulated with these two different Streptamer multimers as explained above, i.e. with either the Streptactin backbone of Example 5 (1.0 mg/ml) or with the large Streptactin backbones (0.1 mg/ml). 3 μl of both the different backbones were either loaded with a combination of 0.5 μg αCD3 and 0.5 μg αCD28 Fab fragments described above. In addition, 4.5 μl of the Streptactin backbone of Example 5 was loaded with 0.5 μg αCD3, 0.5 μg αCD8 Fab and 0.5 μg αCD28 Fab fragment as described above. Untreated (unstimulated) Tresp cells served as negative control and Tresp cells stimulated with Dynabeads (on which αCD3 and αCD28 monoclonal antibodies are irreversible immobilized) as positive control. Tresp cells were seeded in duplicates in 48-well plates in 1 ml cell culture medium supplemented with 30 U/ml IL-2. Cells were incubated at 37° C. with media exchange on day 3 and cell count was analyzed after 1, 3 and 6 days. The results for the CD4+ T responder cells are shown in FIG. 14A, the results for the CD8+ T responder cells are shown in FIG. 14B, with the graphs representing degree of proliferation according to the number of cells harvested per time point for CD4+ Tresp (FIG. 14A) and for CD8+ Tresp in FIG. 14B.

As can be seen from FIG. 14A the soluble multimerization reagents of the present invention on which αCD3 and αCD28 Fab fragments were reversibly immobilized provided for better expansion of CD4+ T cells than Dynabeads.

As evident from FIG. 14B, using the soluble multimerization reagents of the present invention CD8+ T cells could be expanded within the first 6 days at least as efficiently as with Dynabeads. Notably, in this time period, the expansion experiment that used the larger soluble multimerization reagent that carried αCD3 and αCD28 Fab fragments (as first and second agent) showed the best degree of expansion under these culturing conditions. This might again be caused by the soluble "larger oligomeric multimerization reagent" being able to bind to more T cells at the same time than the "smaller" soluble oligomer, thereby being able to stimulate more CD4+ T cells than the "smaller" oligomer.

Example 8

Expansion Kinetics of Purified CD4+ and CD8+ T Cell Cultures with or without Medium Exchange In this Example the combined data from Examples 6 and 7 were normalized on input cell number for the "smaller" soluble multimerization reagent and positive and negative control. No normalization data was obtained on the "larger" multimerization reagent. As explained in Examples 6 and 7, 400.000 to 500.000 CD4+ or CD8+ responder T cells (Tresp) were stimulated with 3 µl of a preparation of Streptactin multimers (1 mg/ml; on which 0.5 µg αCD3 Fab fragment and 0.5 µg αCD28 Fab fragment were immobilized. Untreated (unstimulated) Tresp cells served as negative control and Tresp cells stimulated with Dynabeads as positive control. Tresp cells were seeded in duplicates in 48-well plates in 1 ml cell culture medium supplemented with 30 U/ml IL-2. Tresp cells were seeded in duplicates in 48-well plates in 1 ml cell culture medium supplemented with 30 U/ml IL-2. Cells were incubated at 37° C. with media exchange (straight lines in FIG. 15) or without media exchange (dashed lines in FIG. 15) on day 3 and cell count was analyzed after 1, 3 and 6 days. As evident from the normalized data of FIG. 15A, the "smaller" soluble multimerization reagent on which αCD3 and αCD28 Fab fragments were reversibly immobilized yielded an about 2.5 fold expansion of CD4+ T cells, while the expansion using Dynabeads yielded an about 1.8 fold expansion rate. Thus, the use of a soluble multimerization reagent of the invention even provides for an improvement in the expansion of CD4+ T cells over Dynabeads. Similarly, FIG. 15B, confirms that using the soluble multimerization reagents of the present invention CD8+ T cells could be expanded within the first 3 days at least as efficiently as with Dynabeads.

Example 9

Early Cluster Formation after Activation of Purified CD4+ and CD8+ T Responder Cells Stimulated In Vitro with Reversible aCD3/aCD28 Fab-Streptamer Multimers In this Example, 400.000 CD4+ or CD8+ responder T cells (Tresp) were stimulated with 3 µl of a preparation of oligomeric Streptactin multimerization reagent (1 mg/ml) loaded with a combination of 0.5 µg αCD3- and 0.5 µg αCD28 Fab. Untreated (unstimulated) Tresp cells served as negative control and Tresp cells stimulated with Dynabeads as positive control. Tresp cells were seeded in duplicates in 48-well plates in 1 ml cell culture medium supplemented with 30 U/ml IL-2. Cells were incubated at 37° C. and microscopically analyzed after 1 and 2 days. Stimulation of CD4+ Tresp (FIG. 16A) and CD8+ Tresp (FIG. 16B) are shown for Dynabeads (middle row) and Streptamer multimers (lower row) respectively. The photographs represent degree of cluster formation: For better visibility exemplary clusters are indicated by circles for the stimulation with soluble streptavidin mutein oligomers in FIG. 16A and FIG. 16B. Clusters within the Dynabead stimulation are readily visibly by accumulation of dark stimulatory particles. As evident, both for CD4+ and CD8+ T cells early clusters formed when using the expansion method of the invention that employs a soluble oligomeric multimerization reagent.

Example 10

Expansion Kinetics & Phenotype of Polyclonal Activated/Expanded Bulk CD3+ Central Memory T Cells (Tcm)

In this Example, 500.000 CD3+CD62L+CD45RA-responder Tcm cells (Tresp) were stimulated with 3 µl of a preparation of the soluble oligomeric Streptactin of Example 5 (1 mg/ml) that was either loaded with a combination of 0.5 µg αCD3 and 0.5 µg αCD28 Fab. Furthermore, 4.5 µl of a preparation of Streptactin multimers loaded with 0.5 µg αCD3, 0.5 µg αCD8 Fab and 0.5 µg αCD28 Fab was used as an additional stimulation condition. Untreated (unstimulated) Tresp cells served as negative control and Tresp cells stimulated with Dynabeads (on which αCD3 and αCD28 monoclonal antibodies are irreversible immobilized) as positive control. Tresp cells were seeded in 48-well plates in 1 ml cell culture medium supplemented with 30 U/ml IL-2 only or 30 U/ml IL-2 and 5 ng/ml IL-15. Cells were incubated at 37° C. with media exchange every 3 days and cell count was analyzed after 7 and 14 days. Graphs represent degree of proliferation according to the number of cells harvested per time point, in FIG. 17A only IL-2 supplemented media and in FIG. 17B IL-2 and IL-15 supplemented media. As can be seen from both FIG. 17A and FIG. 17B, the soluble multimerization reagent that has reversibly bound thereon CD3 Fab fragment and αCD28 Fab fragment yields better cell expansion than the Dynabeads. As further shown by the flow-cytometric analysis of CD62L and CD127 surface expression after 14 days of culture in variable cytokine milieus of FIG. 17C, the experimental approaches using soluble multimerization reagents of the present invention retain, under both conditions chosen here, a higher content of CD127-expressing long-lived memory T cells than expansion with Dynabeads. This illustrates a further advantage of the methods of the present invention.

Example 11

Selective Antigen-Specific Expansion of Tcm Responder Cells Out of Bulk CD3+ Central Memory T Cells (Kinetics & Phenotype)

In this Example, the kinetics and the phenotype of selective Antigen specific (Ag-specific) expansion out of purified CD3+CD62L+CD45RA-Tcm responder cells was examined.

In more detail, CD3+CD62L+CD45RA-Tcm responder cells were stimulated in vitro with both a peptide:MHC molecule complex (that acts as first agent that provides a primary activation signal to the cells) and an αCD28 Fab fragment (that acts as second reagent that stimulates an accessory molecule on the surface of the cells). Both the complex of antigen specific peptide with the MHC molecule and the αCD28 Fab fragment were reversibly immobilized on the soluble oligomeric streptavidin mutein (with n≥3) described in Example 5. The peptide that was used for the antigen specific expansion was the peptide CRVLCCYVL (SEQ ID NO: 06), amino acids 309-317 of the immediate-early 1 protein (described in Ameres et al, PLOS Pathogens, May 2013, vol. 9, issue 5, e1003383) representing an HLA-C7/IE-1 epitope that is specific for cytomegalovirus (CMV). The MHC I molecule that presents the peptide carries at the C-terminus of the α chain (heavy chain) the streptavidin binding peptide (SAWSHPQFEK(GGGS)$_2$GG-SAWSHPQFEK, (SEQ ID NO: 07) that is commercially available as "Twin-Strep-tag®" from IBA GmbH, Göttingen, Germany).

For this purpose, 500.000 CD3+CD62L+CD45RA-responder Tcm cells (Tresp) were stimulated Ag-specifically using 3 µl of a preparation of soluble oligomeric Streptactin multimerization reagent functionalized with 0.5 µg of the peptide:MHC class I complexes equipped with the streptavidin binding peptide and with 0.5 µg of the αCD28 Fab described above. As an alternative, 4.5 µl of a of preparation of the Streptactin multimerization reagent were loaded with 0.5 µg of these peptide:MHC class I complexes, 0.5 µg CD8 αFab and 0.5 µg αCD28 Fab. For comparison, polyclonal stimulation was performed, using 3 µl of a preparation of Streptactin multimerization reagent (1 mg/ml) either loaded with a combination of 0.5 µg αCD3 Fab and 0.5 µg αCD28 Fab. Again as the alternative stimulation condition described above, 4.5 µl of a preparation of Streptactin multimerization reagent reversibly loaded with 0.5 µg αCD3 Fab, 0.5 µg αCD8 Fab and 0.5 µg αCD28 Fab was used. Untreated (unstimulated) Tresp cells served as negative control and Tresp cells stimulated polyclonal with Dynabeads (beads on which αCD3 and αCD28 monoclonal antibodies are irreversible immobilized) as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The exemplary flow-cytometric analysis for the fraction of Ag-specific cells that was stimulated/expanded via the soluble strept-tactin oligomer on which the peptide:MHC-I complex for an HLA-C7/IE-1 epitope (for CMV) was immobilized (FIG. 18A) show that these antigen-specific T cells were specifically expanded. The graphs of FIG. 18B to FIG. 18E (that represent the degree of expansion of distinct Ag-specificities according to the number of peptide:MHCI multimer-positive cells harvested per time point in analogy to the expansion experiment shown in FIG. 18A) show that, the multerimerization reagent that uses the respective complex of the Ag-specific peptide and MHC 1 molecule provided for the highest number of expanded cells (ranging from an twentyfold increase in the number of cells for the Ag-specific cells that recognize the pp65 epitope of CMV (amino acids 341-350 (QYDPVAALF, (SEQ ID NO: 08)) restricted by HLA-A2402) (see FIG. 18B) to an 98 fold increase in the number of Ag-specific cells that recognize the HLA-B7/IE-1$_{309\text{-}317}$ epitope (CRVLCCYVL (SEQ ID NO: 06)) of CMV (see FIG. 18E), thereby showing that the expansion method of the present invention is fully applicable to the expansion of Ag-specific cells. Finally, the exemplary flow-cytometric analysis of CD62L and CD127 surface expression after 14 days of culture for HLA-B7/Hexon5 epitope (for adenovirus) shown in FIG. 18F further confirms that experimental approaches using the soluble multimerization reagents of the present invention retain a higher content of CD127-expressing long-lived memory T cells in polyclonal and Ag-specific stimulatory conditions.

Example 12

Selective Ag-Specific Expansion Kinetics & Phenotype of Bulk Central Memory T Cells This Example examines the kinetics of selective Ag-specific expansion out of purified CD3+CD62L+CD45RA-Tcm responder cells that were stimulated in vitro with a) antigen specific peptide MHC I complexes and b) αCD28 Fab fragments that were reversibly immobilized as first and second agent on soluble oligomeric streptavidin muteins.

For this purpose 500.000 CD3+CD62L+CD45RA-responder Tcm cells (Tresp) were stimulated Ag-specifically using 3 µl of a preparation of Streptactin multimerization reagent functionalized with 0.5 µg peptide:MHC class I complexes equipped with a streptavidin binding peptide (the specific peptide represents amino acids 114-124 (CPYSGTAYNSL, SEQ ID NO: 10) of the Hexon 5 protein of adenovirus) restricted by HLA-B07) and 0.5 µg αCD28 Fab. As an alternative, 4.5 µl of a preparation of Streptactin multimerization reagent loaded with 0.5 µg this peptide: MHC class I complex, 0.5 µg αCD8 Fab and 0.5 µg αCD28 Fab. For comparison, polyclonal stimulation was performed, using 3 µl of a preparation of Streptactin multimerization reagent (1 mg/ml) either loaded with a combination of 0.5 µg αCD3 Fab and 0.5 µg αCD28 Fab. Again as the alternative stimulation condition described above, 4.5 µl of a preparation of Streptactin multimers loaded with 0.5 µg αCD3 Fab, 0.5 µg αCD8 Fab and 0.5 µg αCD28 Fab was used. Untreated (unstimulated) Tresp cells served as negative control and Tresp cells stimulated polyclonal with Dynabeads as positive control. Tresp cells were seeded in 48-well plates in 1 ml cell culture medium supplemented with 30 U/ml IL-2 and 5 ng/ml IL-15. Cells were incubated at 37° C. with media exchange every 3 days and cell count was analyzed after 7 and 14 days. The pictures shown in FIG. 19 represent degree of cluster formation on day 5, exemplary Ag-specific stimulation is illustrated for the HLA-B7/Hexon 5 epitope of adenovirus. As can be seen from FIG. 19, such adenovirus antigen specific cells could be specifically expanded from the original CD3+CD62L+CD45RA-Tcm responder population.

Example 13

Yield and Phenotype of Expanded CD8+ T Cells—Size Variation of Soluble Multimerization Reagent and Addition of αCD8-Fab Addition for Stimulation In this Example, the expansion of purified CD8+ T responder cells stimulated in vitro with αCD3/αCD28 Fab fragments that were reversibly immobilized soluble oligomeric streptavidin muteins were examined. In addition, the effect of adding αCD8-Fab to the multimerization reagent for increasing the specificity of the expansion for CD8+ T cells was examined.

For this purpose, 300.000 purified CD8+ responder T cells (Tresp) were separately stimulated with two different Streptactin based multimerization reagents, namely either the small oligomeric Streptactin multimerization reagent of Example 5 (1 mg/ml) or the larger Streptactin oligomers described above (0.1 mg/ml). 3 µl of both different multimerization reagent (backbones) were either loaded with a combination of the 0.5 µg αCD3 and 0.5 µg αCD28 Fab fragments described above. In addition, 4.5 µl of the smaller Streptactin multimerization reagent (backbone) was loaded with 0.5 µg αCD3, 0.5 µg αCD8 Fab and 0.5 µg αCD28 Fab fragments described above. Furthermore 3 µl of the "smaller" Streptactin multimerization reagent (backbone) only functionalized with 0.5 µg αCD3 Fab fragment alone or 0.5 µg αCD28 Fab fragment alone was used. Unstimulated Tresp cells served as negative control and Tresp stimulated with Dynabeads served as positive control. Tresp cells were seeded in duplicates in 48-well plates in 1 ml cell culture medium supplemented with 30 U/ml IL-2. Cells were incubated at 37° C. with media exchange after 3 days and analyzed after 6 days. FIG. 20A depicts the degree of proliferation according to the number of cells harvested at day 6 compared to the negative controls and normalized to the positive control. FIG. 20A shows that the expansion of the CD8+ T cells using the soluble multimerization reagents of the invention result in higher yields of the CD8+ T cells than expansion using dynabeads. The FACS analysis of CD8 surface expression (FIG. 20B) and CD45RO surface expression (FIG. 20C) after cell culture shows that the same phenotype of CD8+ T cells were expanded by either the multimerization reagents of the invention or Dynabeads (the various stimulating conditions were compared using one-way ANOVA and no significant difference (n.s.) was detected). The improved yield of the CD8+ cells using the inventive expansion methods compared to the Dynabeads might be due to the fact that the soluble multimerization reagent can access their target receptors on the cell surface better than the antibodies that are immobilized on the Dynabeads. This improved yield might become very advantageous when expanding rare population of cells from an initial sample.

In addition, comparing the yield of expansion achieved with the multimerization agent on which both the 0.5 µg αCD3 and 0.5 µg αCD28 Fab fragments were jointly immobilized (second column from the left in FIG. 20B) to the yield using two multimerisation reagents which were functionalized only with the αCD3 Fab fragment alone or the αCD28 Fab fragment alone (third column from the left in FIG. 20B), it can be seen that both experiments had the same expansion efficiency. Thus, these experiments show that using one multimerization reagent on which both the first agent and the second agent are jointly immobilized is functionally equivalent to using for the expansion two separate multimerization reagents which are loaded with only the first agent and the second agent, respectively.

Example 14

Yield & Phenotype of Expanded CD8+ T Cells—Titration of Separate Soluble Multimerization Reagents with Different Ratios of αCD3- and αCD28 Fab Fragment Immobilized Thereon In this Example the yield and the phenotype of expanded CD8+ T responder cells (Tresp) that were stimulated in vitro with αCD3/αCD28 Fab fragments that were reversibly immobilized in different amounts on soluble oligomeric streptavidin muteins were examined.

For this purpose 300.000 CD8+ responder T cells (Tresp) were stimulated with varying amounts of a mixture of preparations of the "small" oligomeric Streptactin multimerization reagent (1 mg/ml) functionalized with αCD3 Fab alone and αCD28 Fab alone ("1×" corresponds to 1.5 µg Streptactin multimerization reagent functionalized with 0.5 µg αCD3 alone and 1.5 µg multimerized Streptactin functionalized with 0.5 µg αCD28 Fab fragment alone), or 3 µl of a preparation of the Streptactin multimerization reagent loaded with 0.5 µg αCD3 and α0.5 µg CD28 Fab, or 4.5 µl of a preparation of the Streptactin multimerization reagent loaded with 0.5 µg αCD3, 0.5 µg strep-tagged αCD8 and 0.5 µg αCD28 Fab. Untreated Tresp cells served as negative control and Tresp stimulated with Dynabeads as positive control. Tresp cells were seeded in 48-well plates in 1 ml cell culture medium supplemented with 30 U/ml IL-2. Cells were incubated at 37° C. without media exchange and analyzed after 5 days. FIG. 21A depicts the degree of proliferation according to the number of cells harvested at day 5 compared to the negative controls and normalized to the positive control. FIG. 21A shows that the expansion of the CD8+ T cells using the various soluble multimerization reagents of the invention result in higher yields of the CD8+ T cells than expansion using dynabeads (especially the cumulative total reagent amount of the 5× condition resulted in an optimal expansion of cells especially over time/ increase in total cells by beginning cell division). The FACS analysis of CD8 surface expression (FIG. 21B) and CD45RO surface expression (FIG. 21C) after cell culture shows that the same phenotype of CD8+ T cells were expanded by either the various multimerization reagents of the invention or by the commercially available Dynabeads.

Example 15

Activation of Intracellular Signaling Cascades after Streptamer Multimers Stimulation of aCD19-CAR Transduced Jurkat Cells In this Example the activation of intracellular signaling cascades of transduced Jurkat cells that have been modified to express a tumor-specific chimeric antigen receptor (CAR), namely here CD19 and that were stimulated using the oligomeric Strep-tactin® of Example 5 as soluble multimerization reagent was examined.

For this purpose, 300.000 Jurkat responder cells (Jresp) were stimulated with (A) varying amounts of a mixture of preparations of Streptactin multimerization reagent (1 mg/ml) functionalized with αCD3 Fab and αCD28 Fab fragments described here ("×1" corresponds to 3 µg Streptactin multerization reagent functionalized with 0.5 µg αCD3- and 0.5 µg αCD28 Fab—this provides a "polyclonal Streptactin based multimerization reagent"), or (B) 3 µl of a preparation of Streptactin multimerization reagent functionalized with 0.5 µg (×1) or 1 µg (×2) of the extracellular domain (ECD) of CD19 (the natural ligand for the αCD19-CAR—this provides a "CAR-specific Streptactin based multimerization reagent"), or 3 µl of a preparation of Streptactin multimerization reagent loaded with 0.5 µg (×1) or 1 µg (×2) αIgG recognizing the IgG4 spacer within the αCD19-CAR—this also provides a "CAR-specific Streptavidin mutein based multimerization reagent). ECD of CD19 equipped with a hexahistidine tag was obtained from Sino Biological/Life technologies (SEQ ID NO: 27) and was functionalized for binding to the streptavidin based multimerization reagent by mixing the ECD of CD19 with the adapter molecule His-STREPPER (IBA GmbH, Germany, Order number 2-0920-005) at a molecular ratio of 1:1 and incubating for 15 min at room temperature. The His-STREPPER adapter molecule contains a chelating portion that binds to the hexahistidine tag and a streptavidin binding peptide, thereby temporarily providing the target molecule, here the ECD of CD19 with a streptavidin binding peptide that can reversibly bind to a streptavidin mutein based multimerization reagent. Jresp stimulated with Dynabeads (beads having irreversibly immobilized thereon αCD3- and αCD28-monoclonal antibodies) or PMA and Ionomycin served as positive controls. Jresp cells were seeded in 1.5 ml Eppendorf tubes in 200 µl cell culture medium supplemented with 30 U/ml IL-2. Cells were incubated at 37° C. and put on ice and lysed after 0 min to 20 min of stimulation. Detection of phosphorylated ERK indicates active MAPK signaling, staining of the housekeeper β-Actin indicates loading of equal amounts of total protein per condition and time point. As can be seen from the comparison of FIG. 22A showing activation of the Jurkat cells via the "polyclonal Streptactin multimerization reagent" and FIG. 22B showing activation of the Jurkat cells via the two "CAR-specific Streptactin based multimerization reagents", the Jurkat cells can be activated/expanded via the binding of the CD19 extracellular domain to the CD19 specific chimeric antigen receptor. Since genetic down-stream processing of T cells is almost exclusively performed on pre-selected cell populations, a generic activation via cross-linking of introduced CARs via the IgG4 spacer domain (this is conserved within various CARs with different specificities) broadens the applicability for reversible cell stimulation/expansion in these in vitro cell-processing situations.

Thus, this experiment shows that in principle any cell population that is activated by binding of an agent (ligand) that provides a primary activation signal to the cell population can be expanded using a first agent reversibly immobilized on a multimerization reagent as described here.

Example 16

Yield and Subset Composition of Expanded CD3+ T Cells with Addition of αCD8-Fab for Stimulation The experiment shows the expansion of purified CD3⁺ T responder cells stimulated in vitro with αCD3/αCD28 Fab fragments that were reversibly immobilized on the soluble oligomeric Strep-tactin® of Example 5 that served a soluble multimerization reagent. In one experiment, in addition to αCD3/αCD28 Fab fragments, also a αCD8 Fab fragment commercially available from IBA GmbH, Göttingen, Germany (catalogue number 6-8000-203) was immobilized on the soluble oligomer of the streptavidin mutein in order to test whether it is possible to preferentially stimulate a specific T cell subpopulation in vitro with the reversible aCD3/aCD28 Fab-Streptamer multimers. In more detail, 500.000 purified CD3⁺ responder T cells (Tresp) were stimulated with 3 µl of a preparation of oligomeric Streptavidin (1 mg/ml) loaded with a combination of 0.5 µg of the αCD3 and 0.5 µg of the αCD28 Fab. As an alternative approach, 4.5 µl of the Streptactin oligomer were loaded with 0.5 µg αCD3, 0.5 µg strep-tagged αCD8 Fab and 0.5 µg strep-tagged αCD28 Fab. Unstimulated Tresp cells served as negative control and Tresp stimulated with Dynabeads (beads on which αCD3 and αCD28 monoclonal antibodies are irreversible immobilized) served as positive control. As can be seen from FIG. 23A, the multimerization reagent that is reversibly loaded with the αCD3 Fab fragment, the αCD28 Fab fragment and also the αCD8 Fab fragment provided the highest number of expanded CD3+ T cells. With 1×1×10⁶ the number of expanded cells the yield was about 30% higher than for expansion of these T cells using commercially available Dynabeads. In addition and more important, as shown in FIG. 23B with this multimerization reagent that caries the αCD3 Fab fragment, the αCD28 Fab fragment and the αCD8 Fab fragment, the amount of CD8+ T cells were the highest, compared to both the expansion with Dynabeads or a soluble multimerization reagent of the invention that caries only the αCD3 Fab fragment and the αCD28 Fab fragment as first and second agent as described herein. Thus, also this experiment shows the advantage of the present invention that in addition to a first agent that provides a primary activation signal to the desired cell population and optionally a second agent that provide a co-stimulatory signal, a further agent that is specific for the activation of the desired cell population can be immobilized on the multimerization reagent. Thus, by so doing, the present invention provides for the possibility to preferentially expand or selectively enrich any desired cell (sub)population from an sample that, for example, comprises a variety of different subpopulations.

Example 17

Parallel Antigen-Specific Expansion of Tcm Responder Cells Out of a Single Pool

In this Example, the kinetics of parallel Antigen specific (Ag-specific) expansion out of a single pool of T responder cells stimulated in vitro with multiple reversible peptide: MHC/αCH28 Fab-Streptamer multimers is examined.

500.000 CD3+CD62L+CD45RA-responder Tcm cells (Tresp) are simultaneously stimulated for multiple Ag-specificities using for each specificity, 3 µl of Streptactin multimers functionalized with 0.5 µg of the respective peptide: MHC class I complexes that carries a streptavidin binding peptide and 0.5 µg αCD28 Fab that also carries a streptavidin binding peptide. As an alternative approach, 4.5 µl of Streptactin based multimerization reagent functionalized with 0.5 µg peptide:MHC class I complexes carrying a streptavidin binding peptide, 0.5 µg αCD8 Fab and 0.5 µg αCD28 Fab as described here are used for each specificity. For comparison, polyclonal stimulation is performed, using 3 µl of a preparation of Streptactin based multimerization reagent (1 mg/ml) either reversibly loaded with a combination of 0.5 µg αCD3 Fab and 0.5 µg αCD28 Fab. Again as the alternative stimulation condition described above, 4.5 µl of a preparation of the Streptactin based multimerization reagent reversibly loaded with 0.5 µg αCD3 Fab, 0.5 µg αCD8 Fab and 0.5 µg αCD28 Fab (each of them carrying a streptavidin binding peptide can be used. Untreated (unstimulated) Tresp cells serve as negative control and Tresp cells stimulated polyclonal with Dynabeads (αCD3- and αCD28-mAb coated beads) as positive control. Tresp cells are seeded in 48-well plates in 1 ml cell culture medium supplemented with 30 U/ml IL-2 and 5 ng/ml IL-15. Cells are incubated at 37° C. with media exchange every 3 days and cell count are analyzed after 7 and 14 days.

Example 18

Preferential Proliferation of CD8+ T Cells Among CD3+ T Responder Cells Stimulated In Vitro with Streptavidin Based Multimerization Reagents Reversibly Functionalized with αCD3/αCD8/αCD28 Fab Fragments 300.000 CD3+ responder T cells (Tresp) are stimulated with 3 µl of a preparation of Streptactin multimerization (1 mg/ml) or a preparation of a multimerization reagent using the large Streptactin backbone (0.1 mg/ml) either loaded with a combination of 0.5 µg αCD3 and 0.5 µg αCD28 Fab, or 4.5 µl of a preparation of Streptactin based multimerization reagent loaded with 0.5 µg αCD3, 0.5 µg αCD8 Fab and 0.5 µg αCD28 Fab, or 3 µl of a mixture of preparations of Streptactin based multimerization reagent with 0.5 µg αCD3 Fab alone and 0.5 µg αCD28 Fab alone (each Fab fragment again carries a streptavidin binding peptide). Untreated Tresp cells serve as negative control and Tresp stimulated with Dynabeads (αCD3- and αCD28-mAb coated beads) as positive control. Tresp cells are seeded in duplicates in 48-well plates in 1 ml cell culture medium supplemented with 30 U/ml IL-2. Cells are incubated at 37° C. with media exchange after 3 days and analyzed after 6 days.

Example 19

Preferential Proliferation of CD8+ T Cells Among CD3+ T Responder Cells Stimulated In Vitro with Streptavidin Based Multimerization Reagents Reversibly Functionalized with αCD3 and αCD28 Fab Fragments 300.000 CD3+ responder T cells (Tresp) are stimulated with varying amounts of a mixture of preparations of Streptactin based multimerization reagent (1 mg/ml) functionalized with αCD3 Fab fragment alone and αCD28 Fab fragment alone (1.5 µg Streptactin based multimerization reagent functionalized with 0.5 µg αCD3 Fab fragment alone and 1.5 µg Streptactin based multimerization reagent functionalized with 0.5 µg αCD28 Fab fragment alone), or varying amounts of a mixture of preparations of Streptactin based multimerization reagent functionalized with αCD3 Fab fragment and αCD28 Fab fragment with or without αCD8 Fab fragment (each Fab fragment again carries a streptavidin binding peptide) (3 µg Streptactin based multimerization reagent functionalized with 0.5 µg αCD3- and 0.5 µg αCD28 Fab fragment—without αCD8 Fab fragment, or 4.5 µl of a preparation of Streptactin multimerization reagent loaded with 0.5 µg αCD3 Fab fragment, 0.5 µg αCD8 Fab fragment and 0.5 µg αCD28 Fab fragment, wherein Fab fragment again carries a streptavidin binding peptide). Untreated Tresp cells serve as negative control and Tresp stimulated with Dynabeads (αCD3- and αCD28-mAb coated beads) as positive control. Tresp cells are seeded in 48-well plates in 1 ml cell culture medium supplemented with 30 U/ml IL-2. Cells are incubated at 37° C. with media exchange after 3 days and analyzed after 6 days.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A multimerization reagent, wherein the multimerization reagent is soluble and comprises an oligomer of three or more cross-linked tetramers of a streptavidin mutein, wherein the streptavidin mutein tetramers of the oligomer are crosslinked by a heterobifunctional crosslinker, wherein:
the amino acid sequence of the streptavidin mutein comprises mutations compared to a wild type streptavidin amino acid sequence wherein positions 44 to 47 with reference to the wildtype streptavidin amino acid sequence comprise amino acids Val$^{44}$-Thr$^{45}$-Ala$^{46}$-Arg$^{47}$ (SEQ ID NO:2) or amino acids Ile$^{44}$-Gly$^{45}$-Ala$^{46}$-Arg$^{47}$ (SEQ ID NO:3); and
the streptavidin mutein is reversibly bound to:
(a) a first agent that is a monovalent antibody fragment of an anti-CD3 antibody and comprises a streptavidin-binding peptide C1 able to reversibly bind to at least one binding site Z1 of the streptavidin mutein to form a reversible bond between the streptavidin-binding peptide C1 and the binding site Z1, wherein the first agent is capable of binding to CD3 on the surface of a T cell to stimulate a signal in the T cell; and
(b) a second agent that is a monovalent antibody fragment of an anti-CD28 antibody and comprises a streptavidin-binding peptide C2 that is able to reversibly bind to at least one binding site Z2 of the streptavidin mutein to form a reversible bond between the streptavidin-binding peptide C2 and the binding site Z2, wherein the second agent is capable of binding to CD28 on the surface of the T cell to stimulate an accessory signal to the T cell,
wherein:
the streptavidin-binding peptides C1 and C2 each comprise the sequence Trp-Ser-His-Pro-Gln-Phe-Glu-Lys (SEQ ID NO: 1);
the multimerization reagent is able to stimulate the T cell; and
the reversible bond between said streptavidin-binding peptide C1 of the first agent and said binding site Z1 and the reversible bond between said streptavidin-binding peptide C2 of the second agent and said binding site Z2 can be disrupted in the presence of biotin or a biotin analog.

2. The multimerization reagent of claim 1, wherein individual subunits of the oligomer are crosslinked by a polysaccharide or via a bifunctional linker.

3. The multimerization reagent of claim 1, wherein the monovalent antibody fragment of the first agent is selected from the group consisting of a Fab fragment, a Fv fragment, and a single-chain Fv fragment (scFv).

4. The multimerization reagent of claim 1, wherein the monovalent antibody fragment of the second agent is a Fab fragment, a Fv fragment, or a single-chain Fv fragment (scFv).

5. The multimerization reagent of claim 1, wherein the first agent is a monovalent antibody fragment of an anti-CD3 antibody that is a Fab and the second agent is a monovalent antibody fragment of an anti-CD28 antibody that is a Fab.

6. The multimerization reagent of claim 1, wherein the streptavidin-binding peptide C1 and/or the streptavidin-binding peptide C2 comprises the sequence SAWSHPQFEK (GGGS)$_2$GGSAWSHPQFEK (SEQ ID NO: 7).

7. The multimerization reagent of claim 1, wherein the streptavidin mutein comprises an N-terminal amino acid residue starting at an amino acid in the region of amino acids 10 to 16 of the wildtype streptavidin amino acid sequence and a C-terminal amino acid residue ending in the region of amino acids 133 to 142 of the wildtype streptavidin amino acid sequence.

8. The multimerization reagent of claim 1, wherein the streptavidin-binding peptide C1 and the streptavidin-binding peptide C2 are the same.

9. The multimerization reagent of claim 8, wherein the streptavidin-binding peptide C1 and the streptavidin-binding peptide C2 each comprise the sequence SAWSHPQFEK (GGGS)$_2$GGSAWSHPQFEK (SEQ ID NO: 7).

10. The multimerization reagent of claim 1, wherein the amino acid sequence of the streptavidin mutein comprises amino acids Val$^{44}$-Thr$^{45}$-Ala$^{46}$-Arg$^{47}$ (SEQ ID NO:2).

11. The multimerization reagent of claim 10, wherein the amino acid sequence of the streptavidin mutein comprises an N-terminal amino acid residue starting at an amino acid in the region of amino acids 10 to 16 of the wildtype streptavidin amino acid sequence and a C-terminal amino acid residue ending in the region of amino acids 133 to 142 of the wildtype streptavidin amino acid sequence.

12. A multimerization reagent, wherein the multimerization reagent is soluble and comprises an oligomer of three or more cross-linked tetramers of a streptavidin mutein, wherein streptavidin mutein tetramers of the oligomer are crosslinked by a heterobifunctional crosslinker, wherein:
the amino acid sequence of the streptavidin mutein comprises mutations compared to a wild type streptavidin amino acid sequence wherein positions 44 to 47 with reference to the wildtype streptavidin amino acid sequence comprise amino acids Val$^{44}$-Thr$^{45}$-Ala$^{46}$-Arg$^{47}$ (SEQ ID NO:2) or amino acids Ile$^{44}$-Gly$^{45}$-Ala$^{46}$-Arg$^{47}$ (SEQ ID NO:3); and
the streptavidin mutein is reversibly bound to:
a first agent that is an anti-CD3 Fab antibody fragment comprising a first streptavidin-binding peptide able to reversibly bind to a binding site of the streptavidin mutein to form a reversible bond between the first streptavidin-binding peptide and the binding site of the streptavidin mutein, wherein the first streptavidin-binding peptide is fused to the C-terminus of the heavy chain of the anti-CD3 Fab, and wherein the first agent is capable of specifically binding to CD3 on the surface of a T cell to stimulate a signal in the T cell; and
a second agent that is an anti-CD28 Fab antibody fragment comprising a second streptavidin-binding peptide able to reversibly bind to a binding site of the streptavidin mutein to form a reversible bond between the second streptavidin-binding peptide and the binding site of the streptavidin mutein, wherein the second streptavidin-binding peptide is fused to the C-terminus of the heavy chain of the anti-CD28 Fab, and wherein the second agent is capable of specifically binding to an accessory molecule on the surface of the T cell to stimulate an accessory signal to the T cell,
wherein:
the first and second streptavidin-binding peptides are the same and each comprise the sequence SAWSHPQFEK(GGGS)$_2$GGSAWSHPQFEK (SEQ ID NO: 7);
the reversible bond between each of the first and second streptavidin-binding peptide and the binding site of the streptavidin mutein has a dissociation constant ($K_D$) of between $10^{-5}$ M and $10^{-10}$ M;
the multimerization reagent is able to stimulate the T cell; and
the reversible bond between the first and/or second streptavidin binding-peptides and the binding site of the streptavidin mutein can be disrupted in the presence of biotin or a biotin analog.

13. The multimerization reagent of claim 3, wherein the monovalent antibody fragment is a Fab.

14. The multimerization reagent of claim 1, wherein the amino acid sequence of the streptavidin mutein comprises amino acids Ile$^{44}$-Gly$^{45}$-Ala$^{46}$-Arg$^{47}$(SEQ ID NO:3).

15. The multimerization reagent of claim 14, wherein the amino acid sequence of the streptavidin mutein comprises an N-terminal amino acid residue starting at an amino acid in the region of amino acids 10 to 16 of the wildtype streptavidin amino acid sequence and a C-terminal amino acid residue ending in the region of amino acids 133 to 142 of the wildtype streptavidin amino acid sequence.

16. The multimerization reagent of claim 5, wherein the first and/or second streptavidin-binding peptide comprises the sequence SAWSHPQFEK(GGGS)$_2$GGSAWSHPQFEK (SEQ ID NO: 7).

17. The multimerization reagent of claim 1, wherein the dissociation constant $K_D$ for the reversible binding between said binding site Z1 and said streptavidin-binding peptide C1 and/or the dissociation constant $K_D$ for the reversible binding between said binding site Z2 and said streptavidin-binding peptide C2 is in the range of $10^{-2}$ M to $10^{-13}$ M.

18. The multimerization reagent of claim 9, wherein the first agent is a monovalent antibody fragment of an anti-CD3 antibody that is a Fab and the second agent is a monovalent antibody fragment of an anti-CD28 antibody that is a Fab.

19. The multimerization reagent of claim 1, wherein the streptavidin-binding peptide C1 is fused to the C-terminus of the heavy chain of the first agent and the streptavidin-binding peptide C2 is fused to the C-terminus of the heavy chain of the second agent.

20. The multimerization reagent of claim 9, wherein the streptavidin-binding peptide C1 is fused to the C-terminus of the heavy chain of the first agent and the streptavidin-binding peptide C2 is fused to the C-terminus of the heavy chain of the second agent.

21. The multimerization reagent of claim 16, wherein the streptavidin-binding peptide C1 is fused to the C-terminus of the heavy chain of the first agent and the streptavidin-binding peptide C2 is fused to the C-terminus of the heavy chain of the second agent.

22. The multimerization reagent of claim 18, wherein the streptavidin-binding peptide C1 is fused to the C-terminus of the heavy chain of the first agent and the streptavidin-binding peptide C2 is fused to the C-terminus of the heavy chain of the second agent.

23. The multimerization reagent of claim 1, wherein the biotin analog is desthiobiotin.

24. The multimerization reagent of claim 9, wherein the biotin analog is desthiobioin.

25. The multimerization reagent of claim 16, wherein the biotin analog is desthiobiotin.

26. The multimerization reagent of claim 18, wherein the biotin analog is desthiobiotin.

27. The multimerization reagent of claim 1, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-2}$ M and $10^{-13}$ M.

28. The multimerization reagent of claim 9, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-2}$ M and $10^{-13}$ M.

29. The multimerization reagent of claim 16, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-2}$ M and $10^{-13}$ M.

30. The multimerization reagent of claim 18, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-2}$ M and $10^{-13}$ M.

31. The multimerization reagent of claim 1, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-5}$ M and $10^{-10}$ M.

32. The multimerization reagent of claim 9, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-5}$ M and $10^{-10}$ M.

33. The multimerization reagent of claim 16, wherein the reversible bond between the streptavidin-binding peptide C1 and the at least one binding site Z1 of the streptavidin mutein and the reversible bond between the streptavidin-binding peptide C2 and the at least one binding site Z2 of the streptavidin mutein each individually has a dissociation constant ($K_D$) of between $10^{-5}$ M and $10^{-10}$ M.

34. The multimerization reagent of claim 18, wherein the reversible bond between the streptavidin-binding peptide C1 and the at least one binding site Z1 of the streptavidin mutein and the reversible bond between the streptavidin-binding peptide C1 and the at least one binding site Z1 of the streptavidin mutein each individually has a dissociation constant ($K_D$) of between $10^{-5}$ M and $10^{-10}$ M.

35. The multimerization reagent of claim 1, wherein the streptavidin mutein tetramers of the oligomer are cross-linked by amine-to-thiol crosslinks.

36. The multimerization reagent of claim 9, wherein the streptavidin mutein tetramers of the oligomer are cross-linked by amine-to-thiol crosslinks.

37. The multimerization reagent of claim 16, wherein the streptavidin mutein tetramers of the oligomer are cross-linked by amine-to-thiol crosslinks.

38. The multimerization reagent of claim 18, wherein the streptavidin mutein tetramers of the oligomer are cross-linked by amine-to-thiol crosslinks.

* * * * *

UNITED STATES PATENT AND TRADEMARK OFFICE
CERTIFICATE OF CORRECTION

| | |
|---|---|
| PATENT NO. | : 11,274,278 B2 |
| APPLICATION NO. | : 15/304045 |
| DATED | : March 15, 2022 |
| INVENTOR(S) | : Lothar Germeroth and Christian Stemberger |

It is certified that error appears in the above-identified patent and that said Letters Patent is hereby corrected as shown below:

In the Claims

In Claim 24 at Column 78, Line 12, please delete "desthiobioin" and substitute therefor:
--desthiobiotin--.

Signed and Sealed this
Fifteenth Day of August, 2023

Katherine Kelly Vidal
Director of the United States Patent and Trademark Office